United States Patent
Karellas

(10) Patent No.: US 6,717,174 B2
(45) Date of Patent: Apr. 6, 2004

(54) SYSTEM FOR QUANTITATIVE RADIOGRAPHIC IMAGING

(75) Inventor: Andrew Karellas, Auburn, MA (US)

(73) Assignee: University of Massachusetts Medical Center, Worcester, MA (US)

(*) Notice: Subject to any disclaimer, the term of this patent is extended or adjusted under 35 U.S.C. 154(b) by 0 days.

(21) Appl. No.: 09/896,427

(22) Filed: Jun. 29, 2001

(65) Prior Publication Data

US 2002/0070365 A1 Jun. 13, 2002

Related U.S. Application Data

(63) Continuation of application No. 09/195,189, filed on Nov. 17, 1998, now abandoned, which is a continuation-in-part of application No. 08/748,384, filed on Nov. 13, 1996, now Pat. No. 5,864,146, which is a continuation-in-part of application No. PCT/US96/06838, filed on May 13, 1996, which is a continuation-in-part of application No. 08/469,895, filed on Jun. 6, 1995, now Pat. No. 6,031,892, which is a continuation-in-part of application No. 08/438,800, filed on May 11, 1995, which is a continuation-in-part of application No. 07/853,775, filed on Jun. 2, 1992, now Pat. No. 5,465,284, which is a continuation-in-part of application No. 07/446,472, filed on Dec. 5, 1989, now Pat. No. 5,150,394.

(51) Int. Cl.$^7$ ................................................ A61B 6/14
(52) U.S. Cl. ...................................... 250/582; 250/584
(58) Field of Search ................................ 250/582, 584, 250/586, 484.3, 484.4

(56) References Cited

U.S. PATENT DOCUMENTS

| | | | |
|---|---|---|---|
| 4,298,800 A | 11/1981 | Goldman | 250/445 |
| 4,365,269 A | 12/1982 | Haendle | 358/111 |
| 4,383,327 A | 5/1983 | Kruger | 378/19 |
| 4,593,400 A | 6/1986 | Mouyen | 378/99 |
| 4,686,695 A | 8/1987 | Macovski | 378/146 |
| 4,803,359 A | 2/1989 | Hosoi et al. | 250/327.2 |
| 4,843,241 A * | 6/1989 | Saotome et al. | 250/484.1 |
| 4,852,137 A | 7/1989 | Mackay | 378/62 |
| 4,933,558 A | 6/1990 | Carter et al. | 250/327.2 |
| 4,987,307 A | 1/1991 | Rizzo et al. | 250/368 |

(List continued on next page.)

FOREIGN PATENT DOCUMENTS

| | | |
|---|---|---|
| DE | 43 28 782 | 3/1995 |
| EP | 0 022 564 | 1/1981 |
| EP | 270 761 | 6/1988 |
| EP | 0 288 004 | 10/1988 |
| EP | 0 373 717 | 6/1990 |
| EP | 0 443 666 | 8/1991 |
| WO | WO 94/21174 | 9/1994 |

OTHER PUBLICATIONS

Hildebolt, C., et al., "PSP–Photostimulable Phosphor Dental Radiography", (1995).

Brandt, M., "The Design and Performance Characteristics of a Collector for High Efficiency Detection of Photostimulable Phosphor Emissions", Spie vol. 1896, *Physics of Medical Imaging* (1993).

(List continued on next page.)

Primary Examiner—Scott J. Sugarman
Assistant Examiner—Richard Hanig
(74) Attorney, Agent, or Firm—Bowditch & Dewey, LLP

(57) ABSTRACT

A system for imaging of bodily tissue in which an x-ray source, an optical storage element, a light source and a detector array are used to accurately image selected tissue. An x-ray source generates x-rays which pass through a region of a subject's body, forming an x-ray image which reaches the storage element. The storage element reradiates a spatial intensity pattern corresponding to the image, the pattern being detected by a sensor. The image is digitized by the sensor and processed by a controller before being stored as an electronic image. Each image is directed onto a CCD or amorphous silicon detector to generate individual electronic representations of separate images.

26 Claims, 42 Drawing Sheets

U.S. PATENT DOCUMENTS

| | | | | |
|---|---|---|---|---|
| 5,065,023 A | * | 11/1991 | Lindmayer | 250/484.1 |
| 5,115,336 A | * | 5/1992 | Schildkraut | 359/263 |
| 5,127,032 A | | 6/1992 | Lam et al. | 378/189 |
| 5,150,394 A | | 9/1992 | Karellas | 378/62 |
| 5,166,962 A | | 11/1992 | Murooka et al. | 378/34 |
| 5,262,649 A | | 11/1993 | Antonuk et al. | 250/370.09 |
| 5,307,396 A | | 4/1994 | Tsuchino | 378/146 |
| 5,347,139 A | * | 9/1994 | Barker et al. | 250/583 |
| 5,382,798 A | | 1/1995 | Mouyen | 250/370.11 |
| 5,400,379 A | | 3/1995 | Pfoh et al. | 378/19 |
| 5,434,418 A | | 7/1995 | Schick | 250/370.11 |
| 5,485,500 A | * | 1/1996 | Baba et al. | 378/98.2 |
| 5,510,623 A | | 4/1996 | Sayag et al. | 250/370.11 |
| 5,554,850 A | | 9/1996 | Hejazi | 250/367 |
| 5,576,552 A | | 11/1996 | Rantanen | 250/484.4 |
| 5,864,146 A | * | 1/1999 | Karellas | 250/581 |
| 6,031,892 A | | 2/2000 | Karellas | 378/98.3 |

OTHER PUBLICATIONS

Newell, J. "Digital Imaging In Diagnostic Radiology", *Churchill Livingstone*, New York, 1990.

Kashima et al., "Intraoral Computer Radiography Using the Fuji Computed Radiography Imaging Plate", *Oral Surgery*, vol. 78, No. 2 (Aug., 1994).

Karellas, et al., "Charge–Coupled Device Detector: Performance Considerations and Potential For Small–Field Mammographic Imaging Applications", (1991).

Karellas, et al., "Imaging of Radionuclide Emissions With a Low–Noise Charge–Coupled Device", *Nuclear Science*, Dec., 1992.

* cited by examiner

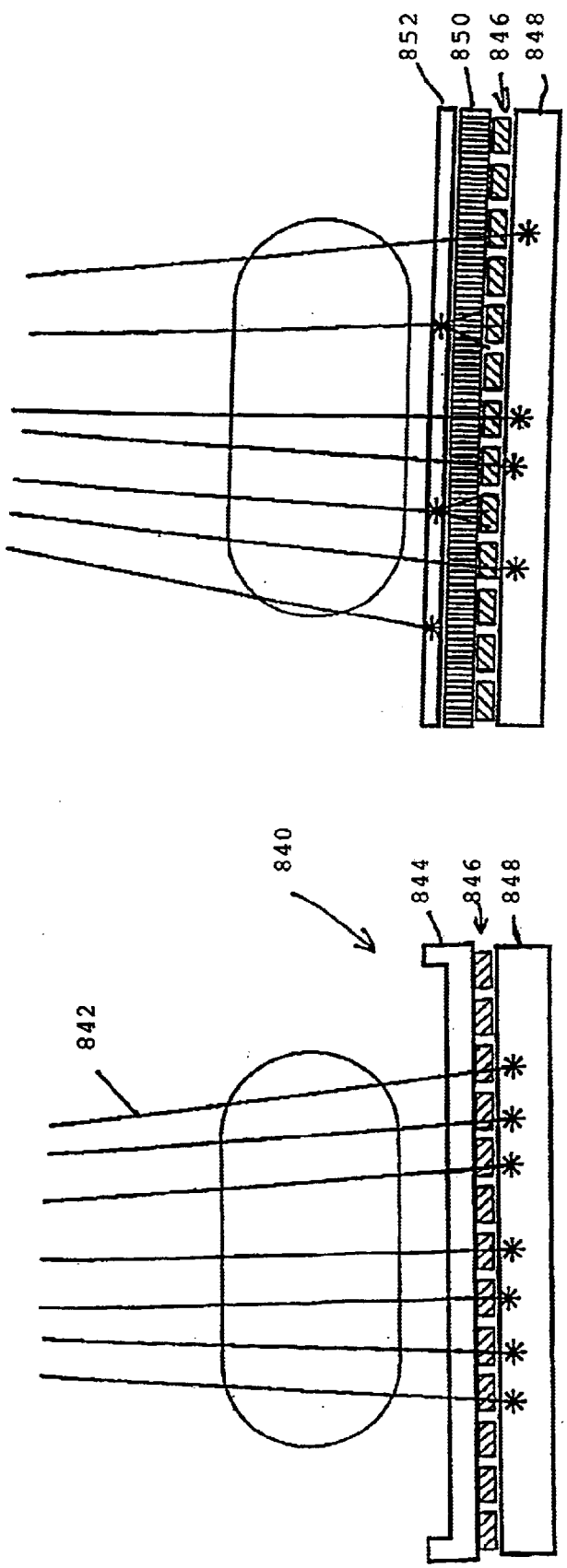

CCDs joined together on two sides

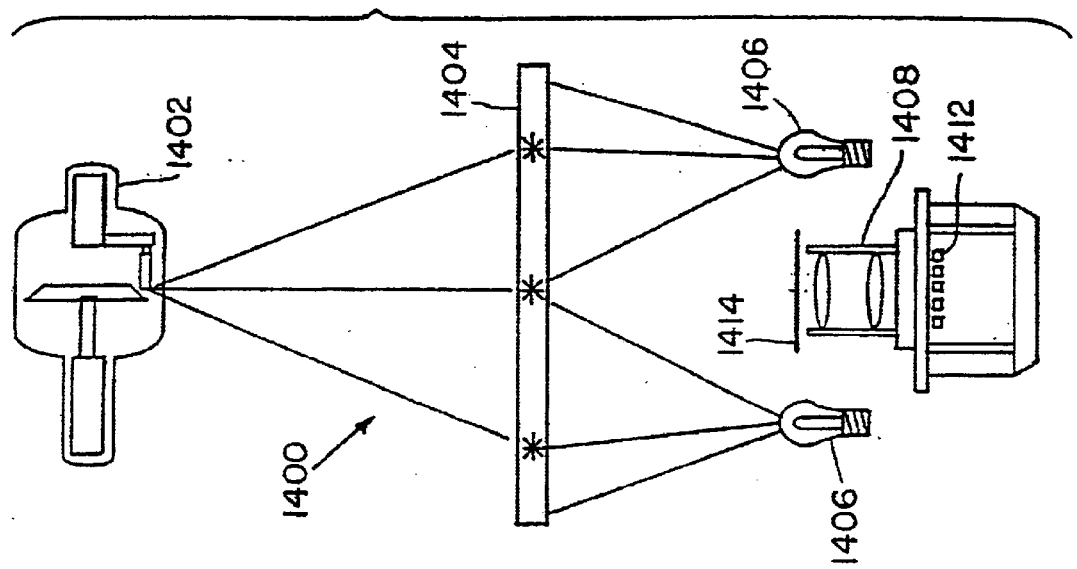
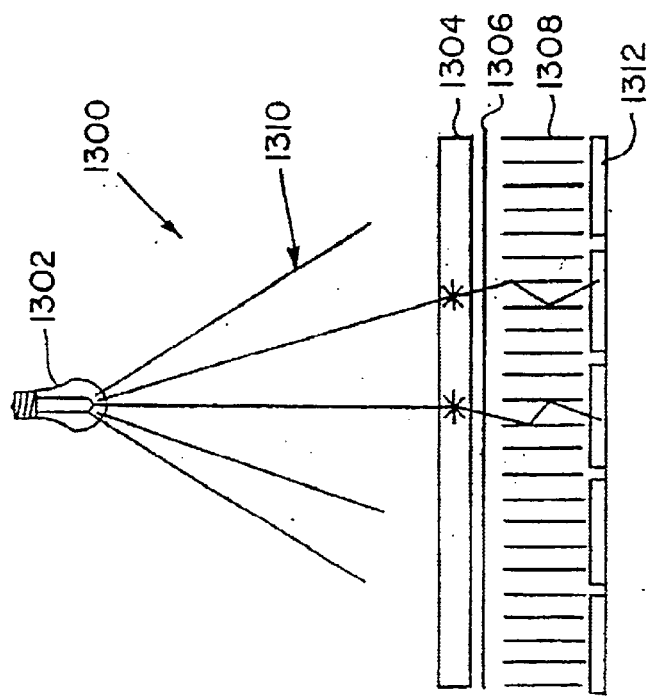
FIG. 38A
FIG. 37

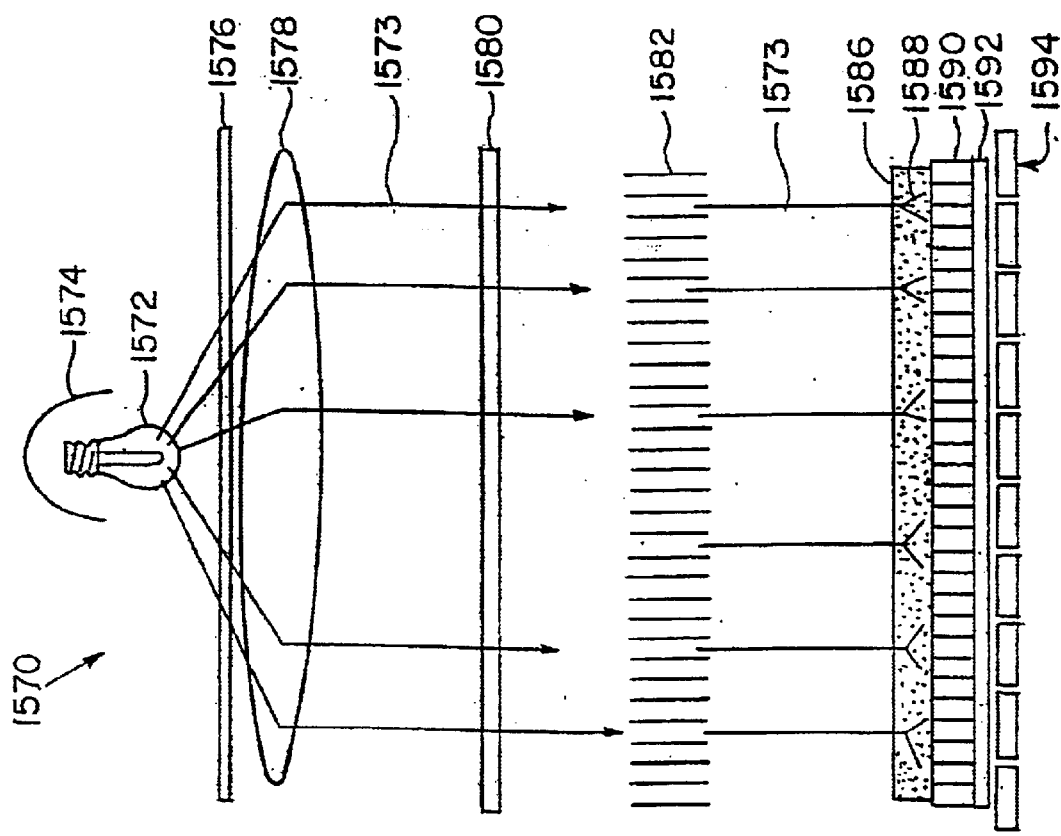
FIG. 40C
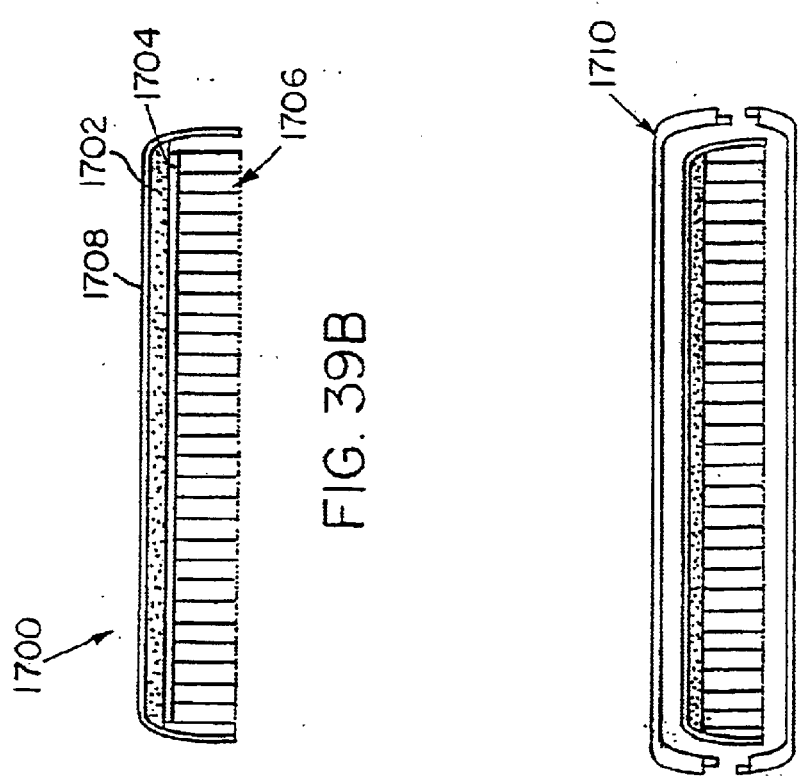
FIG. 39B
FIG. 39C

SYSTEM FOR QUANTITATIVE RADIOGRAPHIC IMAGING

RELATED APPLICATIONS

This application is a continuation of U.S. patent application Ser. No. 09/195,189 filed on Nov. 17, 1998 now abandoned which is a continuation-in-part of U.S. patent application Ser. No. 08/748,384 filed on Nov. 13, 1996, now U.S. Pat. No. 5,864,146, which is a continuation-in-part of International Application No. PCT/US96/06838 filed May 13, 1996, which is a continuation-in-part of U.S. application Ser. No. 08/469,895 filed on Jun. 6, 1995, now U.S. Pat. No. 6,031,892, which is a continuation-in-part of U.S. application Ser. No. 08/438,800 filed on May 11, 1995 which is a continuation-in-part of U.S. application Ser. No. 07/853,775 filed Jun. 2, 1992, now U.S. Pat. No. 5,465,284, which is a continuation-in-part of U.S. application Ser. No. 07/446,472 filed Dec. 5, 1989, now U.S. Pat. No. 5,150,394, the above applications being incorporated herein by reference in their entirety.

BACKGROUND OF THE INVENTION

In recent years the use of radiological examining equipment to make measurements of bone density in patients has continually increased. In particular, the use of such equipment in diagnosing and analyzing osteoporosis has become prevalent in the medical community. Osteoporosis is characterized by the gradual loss of bone mineral content or atrophy of skeletal tissue, resulting in a corresponding overall decrease in average bone density. Such a condition is common in elderly women and greatly increases the risk of fracture or similar bone related injury.

The presently available techniques for the radiological measurement of bone density utilize a rectilinear scanning approach. In such an approach, a radiation source, such as a radionuclide source or an x-ray tube, and a point detector are scanned over a patient in a raster fashion. This scan results in an image which has been derived from the point-by-point transmission of the radiation beam through the bone and soft tissue of a patient. The calculation of the bone-mineral concentration the ("bone density") is usually performed by a dual energy approach.

The rectilinear scanning approach is generally limited by its long scanning time and its lack of good spatial resolution. The poor spatial resolution results in an inability to provide an image displaying high anatomical detail and which will permit accurate determination of the area in the scan occupied by bone. Moreover, the output of the x-ray source and the response of the detector must be closely monitored in order to assure high accuracy and precision.

SUMMARY OF THE INVENTION

In accordance with the present invention, a bone densitometry apparatus is provided for examining a subject's body. A single or dual energy x-ray source directs a beam of x-ray radiation toward the subject's body. The radiation is applied to the entire region of the body being examined. A scintillation screen receives the x-ray radiation passing through the body of the subject, and emits radiation in the visible spectrum with a spatial intensity pattern proportional to the spatial intensity pattern of the received x-ray radiation.

A charge coupled device (CCD) then receives radiation from the scintillation screen. This CCD sensor generates a discrete electronic representation of the spatial intensity pattern of the radiation emitted from the scintillation screen. A focusing element between the screen and the CCD sensor focuses the scintillation screen radiation onto the CCD sensor. To prevent ambient radiation from reaching the CCD sensor, the present embodiment employs a shade or hood surrounding a region between the scintillation screen and the CCD sensor. A CCD controller then processes the electronic representation generated by the CCD sensor, and outputs corresponding image data.

A dual photon x-ray source is used to allow the examination to be performed with x-rays at two different energy levels. This source can be an x-ray tube, or a radionuclide source with a filter element to remove one of the energy levels when desired. Correlation of the image data retrieved using each of the two x-ray energy levels provides quantitative bone density information.

A focusing element between the scintillation screen and the CCD sensor can take the form of a lens or a fiber optic reducer. An image intensifier can be used in conjunction with the CCD sensor. The image intensifier can be a "proximity type" image diode or a microchannel based device. It can also be directly attached to the CCD. An image storage device used with the CCD controller allows manipulation of the CCD sensor output signals by a data processor. This includes the correlation of measurements utilizing x-ray beams of two different energy levels. The system can also be adapted to operate at higher shutter speeds enabling the counting of x-ray transmissions. This provides energy measurements of x-ray transmissions that are useful in certain applications.

In an alternative embodiment, a detector made of amorphous silicon is used to receive and detect the radiation from the scintillation screen to generate the electronic representation of the spatial intensity pattern of the received x-ray beams. The amorphous silicon detector can replace the CCD detector or it can be used to receive the x-rays directly.

In another preferred embodiment, the apparatus of the invention includes two scintillation screens, each of which is associated with its own respective CCD detector or amorphous silicon detector. One of the scintillators is reactive to high-energy x-rays and generates an optical image of the spatial intensity pattern of the high-energy x-ray pattern. Its associated detector detects the image and generates an electronic representation of the high-energy x-ray pattern. The other scintillator is reactive to low-energy x-rays to simultaneously generate an optical image of the low-energy pattern. Its associated detector generates an electronic representation of the low-energy x-ray pattern. The data processor performs the correlations of the measurements for the x-rays at two different energy levels.

An additional preferred embodiment is directed to systems and methods of imaging spectroscopy where a charge coupled device (CCD) is optically coupled to a scintillator and measures or counts the spatial intensity distribution of a radionuclide that has been introduced into bodily tissue, either in vivo or in vitro. CCD's of sufficient thickness can be used to measure gamma ray events without the use of a scintillator in certain applications. The CCD has sufficient resolution and sensitivity to measure such distributions accurately, usually in less than two minutes. Radiation sources that emit radiation having an energy in a range between 10 and 2,000 keV, and preferably in the range between 20 and 600 keV, are delivered to the cancerous tissue or any other suitable pathologic abnormality.

The CCD acquires "frames" of information by counting the number of gamma-ray events over a selected period of time. Each frame, or a sequence of frames that have been added or summed to provide an image, can be filtered using pulse height analysis techniques to substantially reduce or eliminate scattered radiation. Pulse height analysis can also be utilized to discriminate between signals having different energy levels that contain diagnostically significant information. The system's discrimination and energy measuring capabilities render it suitable for diverse applications.

An optical storage element such as photostimulable phosphor can be used with the imaging area detectors described herein to perform x-ray imaging and quantitative analysis. The optical storage system described herein uses an x-ray source to generate x-rays that are transmitted through the object to be imaged and/or scanned. The optical storage element collects the transmitted x-rays, where the spatial distribution of the collected information is correlated with the density distribution of the object. The storage element is then illuminated by a second light source, such as a laser or a high power broadband source, to induce the emission of the stored optical energy distribution. The emitted optical distribution is detected by an area detector to provide an image of the object. This has a variety of applications in both bone and soft tissue imaging and in particular for digital dental radiography.

Another preferred embodiment of the invention provides a method of fabricating a pixelated filter structure of dual energy imaging applications. This procedure uses microfabrication techniques to fabricate a thin film filter with an area detector to simultaneously collect two different energies in an x-ray imaging system. This is particularly well suited to flat panel detectors such as CCDs having small pixel sizes.

BRIEF DESCRIPTION OF THE DRAWINGS

FIG. 25B illustrates another preferred embodiment of an x-ray detection system utilizing a transmissive detector.

FIG. 25C illustrates a preferred embodiment utilizing two scintillators with a detector array.

FIG. 37 illustrates an optical stimulation system for detecting a stored x-ray image.

FIGS. 38A and 38B illustrate additional preferred embodiments for x-ray imaging using an optical storage element.

FIGS. 39B and 39C illustrate an alternate embodiment of an oral insert in the form of a cassette including the optical storage element and a removable cover.

DETAILED DESCRIPTION OF THE PREFERRED EMBODIMENTS

Figure 1:
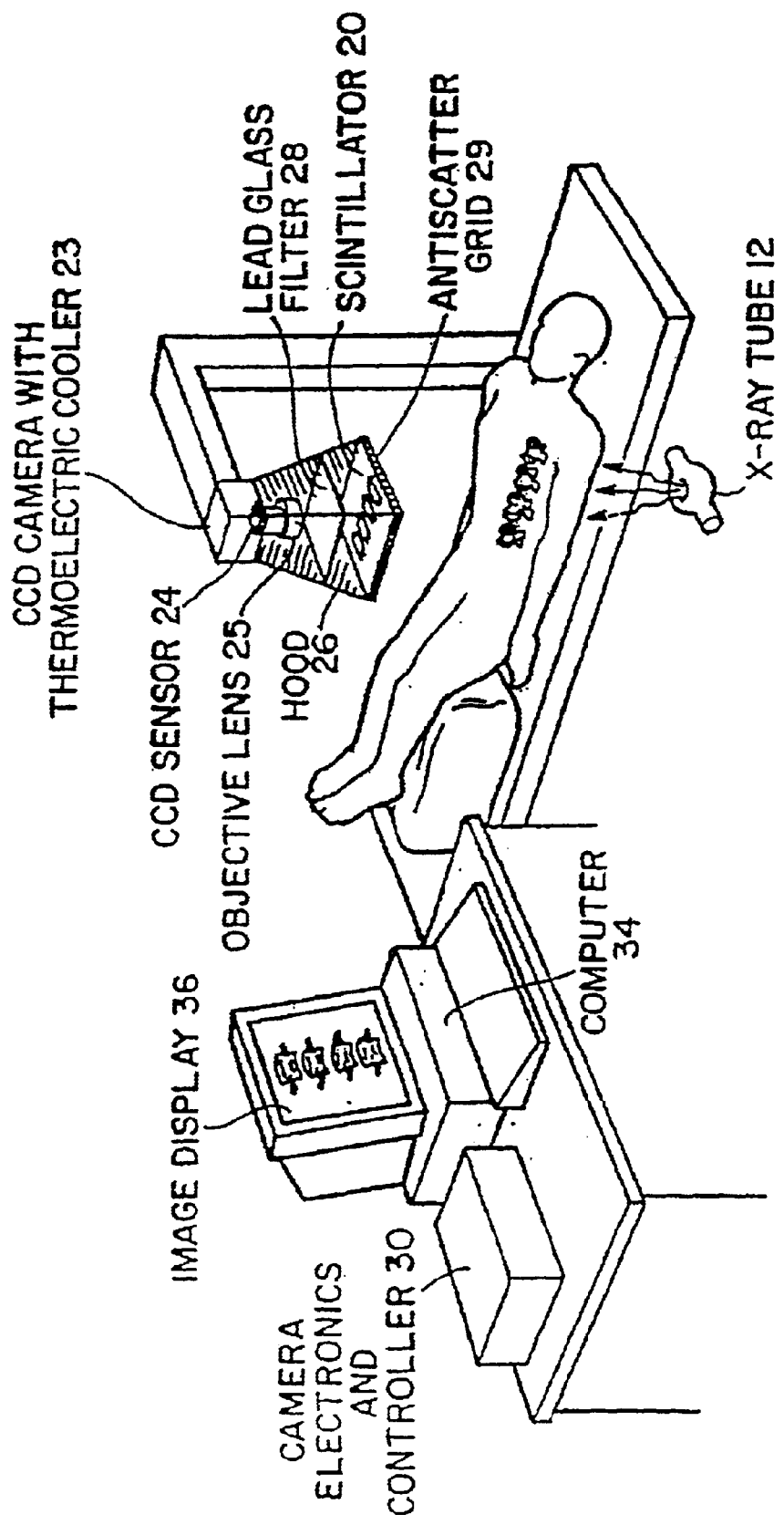
FIG. 1 is a perspective view of the imaging system of the present invention.

In FIG. 1 a preferred embodiment of the invention for performing bone densitometry studies uses a detector 10 and either an x-ray tube 12 or a radionuclide radiation source such as Gadolinium-153. The detector 10 comprises a scintillating plate 20 which is optically coupled to a two-dimensional charge-coupled device 24 (CCD). The CCD is a two dimensional array of detectors integrated into a single compact electronic chip. The optical coupling between the scintillating plate 20 and the CCD 24 is accomplished by an optical grade lens 25. Such a lens should have a low f-number (0.6–1.8) for adequate light collection from the screen. The collection efficiency (E) of light from the scintillating plate emitted in the direction of the CCD can be computed by the equation:

$$E = \frac{tm^2}{4f^2(m+1)^2}$$

where
t: Transmission factor of light through the lens
m: magnification from the Scintillating plate to the CCD
f: f-number of the lens In an alternate approach, the optical coupling between the scintillating plate and the CCD can be performed with a fiber optic reducer.

Figure 2:
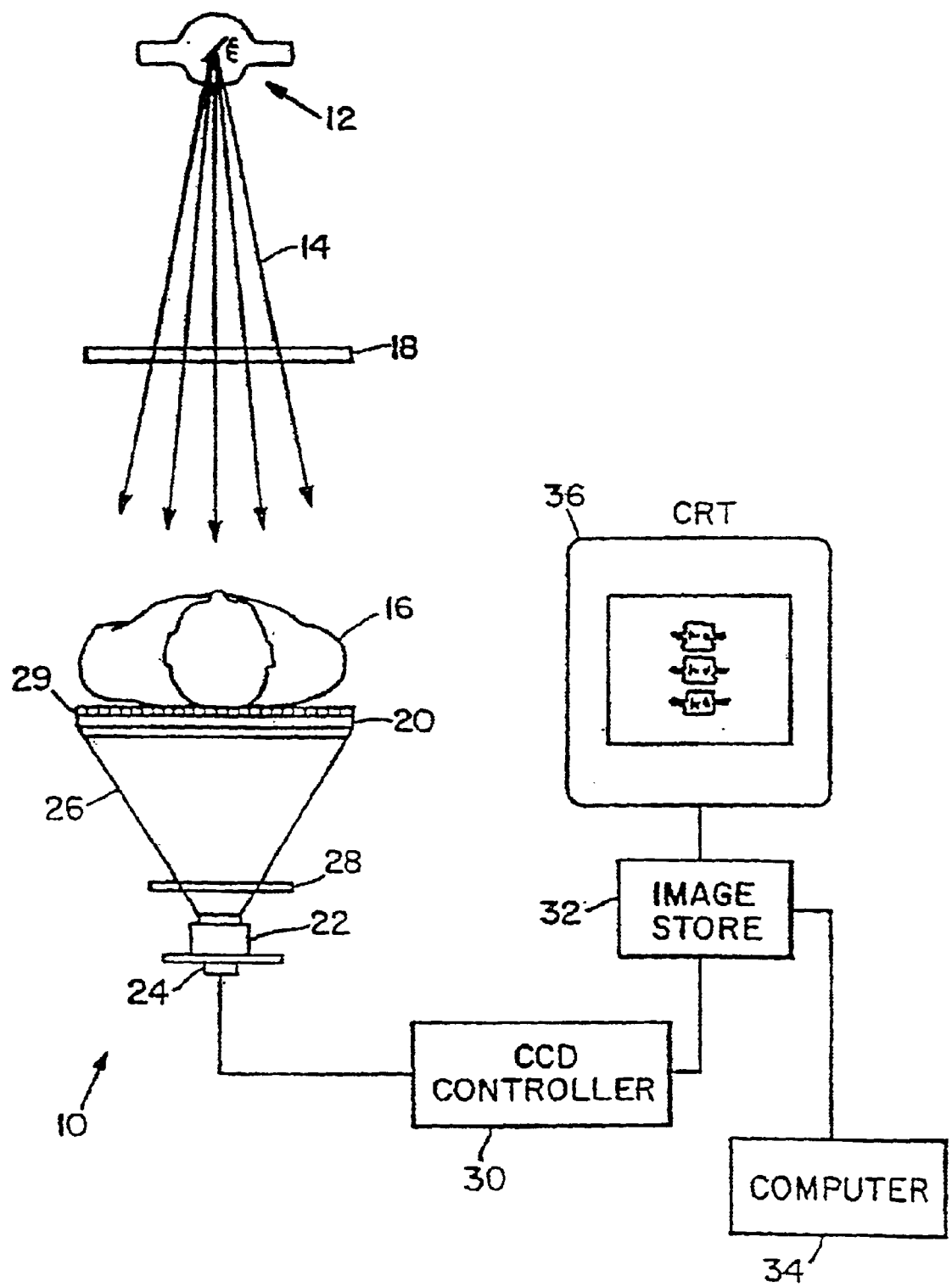
FIG. 2 illustrates in schematic view a bone density measuring apparatus using a lens to focus image data from a scintillator onto a CCD or other area sensor.

Referring to FIG. 2, a bone densitometry apparatus 10 has an x-ray tube 12 which delivers a beam of x-rays 14 towards the body of a subject 16 being examined. The x-ray tube is capable of emitting x-ray radiation at each of two distinct energy levels. The two energy levels are used to obtain two distinct x-ray images of the patient, as is discussed later. Note in comparison to FIG. 1, the source can be positioned above the patient and the detector below the table.

When the subject 16 is irradiated with the x-ray energy, a percentage of the x-rays reaching the subject 16 is absorbed by the subject's body, the amount of absorption depending on the density of bone or tissue upon which the x-rays are incident. Since x-rays generally travel in a straight line, the x-ray energy exiting the subject's body on the side of the body away from the source 12 is a spatial representation of absorption in the subject's body, and therefore of relative tissue and skeletal densities.

To receive the x-rays passing through the subject's body, a scintillation screen 20 is provided on the side of the patient away from the x-ray source 12. The scintillation screen 20 is a fluorescent material sensitive to x-rays, and when it receives x-ray energy it reradiates visible light. The spatial intensity patterns of the radiation emitted from the scintillation screen is proportional to the spatial intensity pattern of the x-ray radiation received by the screen 20. Thus the scintillation screen 20 provides an image in the visible spectrum, or alternating in the ultraviolet or near infrared, which is regionally proportional to the x-ray image reaching the scintillation screen 20.

A lens 22 is positioned between the scintillation screen 20 and a CCD sensor 24. The CCD sensor 24 is an array of photosensitive pixels using closely spaced MOS diodes which convert photons to electrons and thereby generate a discrete electronic representation of a received optical image. The lens 22 faces the scintillation screen and focuses the visible light emitted from the scintillation screen 20 through the lens 22 and onto the surface of the CCD sensor 24. In order to prevent ambient light from reaching the CCD sensor, a shade surrounding the region between the scintillation screen 20 and the lens 22 is provided in the form of a photographic bellows 26. The shading of bellows 26 serves to reduce the optical noise level of the image signal reaching the CCD sensor 24.

Although the scintillation screen 20 absorbs most of the x-rays incident upon it, some may still be transmitted through the screen 20 and interfere with the optical image signal of the scintillation screen 20. The direct interaction of x-rays with a CCD sensor produces very bright pixels resulting in a "snow" effect in an optical image detected by the sensor. In addition, prolonged direct x-ray irradiation of a CCD sensor can increase its dark current. For these reasons, an optical grade lead-glass or lead acrylic filter 28 is positioned between the scintillation screen 20 and the lens 22 or alternatively, between the lens and the CCD. The lead-glass filter 20 absorbs most of the stray x-rays and prevents them from reaching the CCD sensor 24. An anti-scatter grid 29 is used between the patient and scintillation screen for preventing scattered x-rays from reaching the screen.

During a typical examination, the subject 16 is placed between the x-ray source 12 and the scintillation screen 20.

The x-ray source is then activated for a short time interval, typically one to five seconds. As x-rays are differentially transmitted and absorbed through the body of the subject 16, they interact with the scintillation screen 20. Upon interaction, the screen 20 emits light in the visible part of the electromagnetic spectrum. In the present embodiment, the scintillation screen is a terbium-activated material and emits light in the region of 540 nm.

The light emitted from the scintillator is transported to the CCD sensor via the lens 22. Upon interaction with the CCD sensor 24, light energy is converted into electrons which are stored in each pixel of the CCD sensor 24. The CCD sensor 24 of the present embodiment consists of 512×512 pixels, but such sensors come in a number of different sizes. The CCD sensor "integrates" the image signal from the scintillation screen in that it senses the optical image and stores charge during the entire x-ray exposure interval. After termination of the x-ray exposure, the discrete representation in the CCD 24 is read out by CCD controller 30. The CCD controller 30 reads the image representation from the CCD sensor 24 pixel by pixel and organizes it into a digital array. The digital array, representing spatial position and x-ray intensity, is then output to a memory or image store 32. From the image store 32, the image can be accessed by a data processor 34 for performing image processing techniques. A cathode ray tube (CRT) 36 is also provided to allow the image to be displayed before or after processing by data processor 34.

Unlike other conventional detection schemes, such as film screen radiography, CCD-based imaging provides a linear quantitative relationship between the transmitted x-ray intensity and the charge generated in each pixel of the CCD. After the first high energy x-ray exposure is acquired, the resulting image is stored in image store 32 and a second exposure with a low energy x-ray beam is acquired with the subject 16 in the same position. During this exposure, a low energy x-ray beam is used which is typically at about 70 kVp with a tube. Current at about 1 mA. The tube is capable of accelerating electrons at 40 kVp and up to approximately 140 kVp. Note that the tube potential and current are controlled by the computer menu. The low energy x-ray image is then stored in image store 32 with the high energy exposure. Each image provides quantitative information about the relative transmission of x-rays through soft tissue and bone.

Once both images are obtained, comparative processing techniques of dual photon absorptiometry are applied to determine quantitative density measurements of those body regions scanned by the x-rays. The correlation of two images generated by x-rays of two different energy levels over a short time interval results in the substantial reduction in the likelihood of systematic pixel-by-pixel errors caused by instability of the x-ray tube output.

Because the present embodiment of the invention is concerned with an area detector as opposed to a scanning detector, the measurement time necessary for a densitometry examination is greatly reduced. Rather than scanning across the region to be examined in a rectilinear fashion, the entire region is irradiated simultaneously and the resulting image processed simultaneously. Typically, the entire procedure using the present dual photon technique lasts 30 to 60 seconds, depending on the power of the x-ray tube and processing speed of the supporting electronics.

Figure 3:
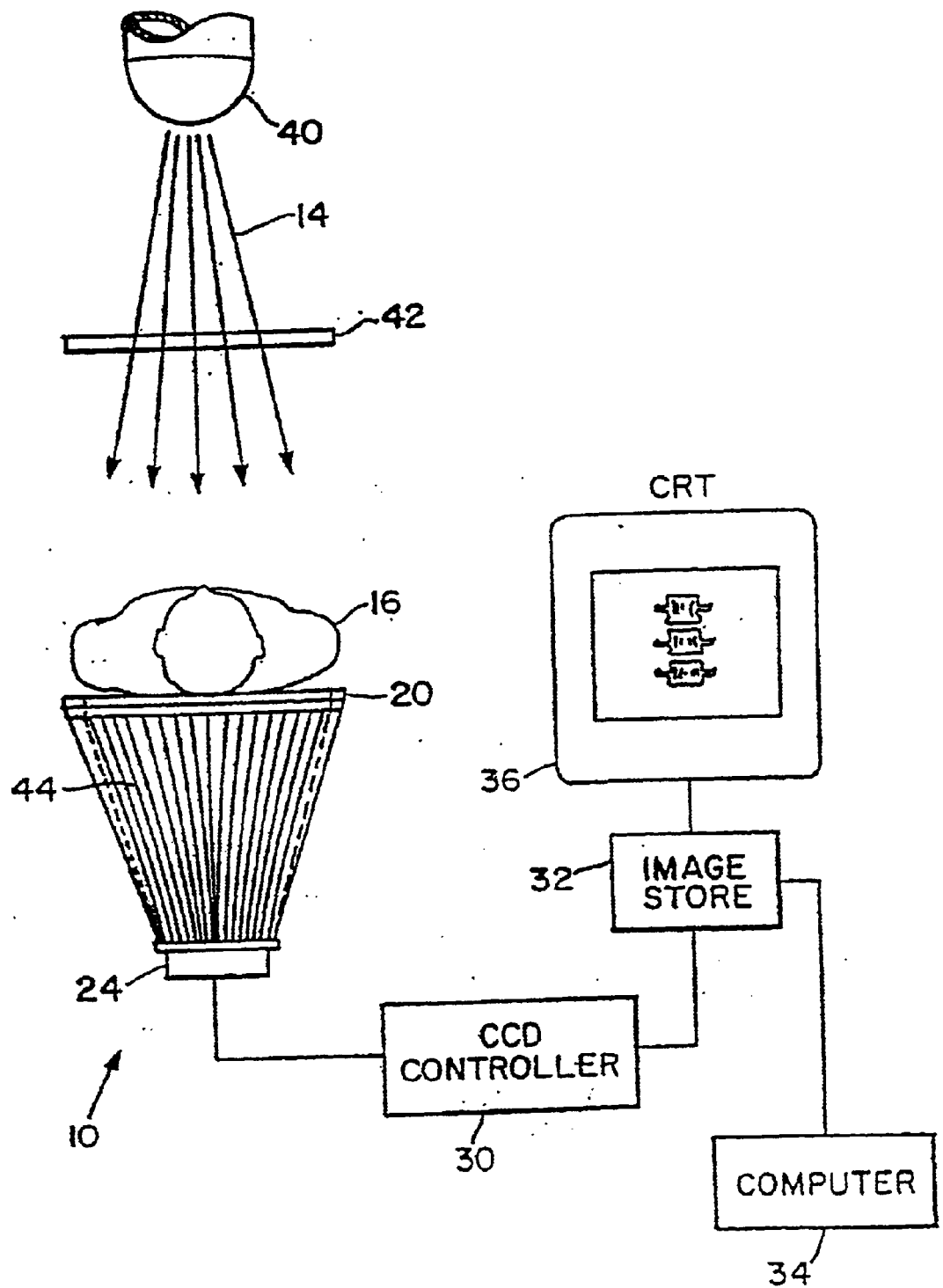
FIG. 3 illustrates in schematic view a bone density measuring apparatus using a fiber optic reducer to deliver an image from a scintillation screen to an area sensor.

FIG. 3 shows an alternative embodiment to that of FIG. 2. In this embodiment, the x-ray tube source 12 of FIG. 2 is replaced with radionuclide source 40. The radionuclide source is gadolinium-153. Gadolinium-153 emits photons simultaneously in two energy bands, a lower energy band of 44 keV and an upper energy band of 100 keV. Thus, the gadolinium source is a dual photon radiation source. In order to allow the images from the two different energy levels to be obtained separately, an x-ray filter 42 is placed between the source 40 and the subject 16. In the present embodiment, the filter 42 is copper or a K-edge filter, and eliminates nearly all of the low energy (44 keV) emission from the beam. Removal of the filter restores the beam to its dual energy nature. The filter 42 is implemented as an electromagnetic shutter which may be opened and closed in the line of the x-ray beam. A high energy image is acquired first with the filter shutter closed, after which an image is obtained using the dual energy beam with the shutter open.

Both electronic images are stored, and an image representative of the transmission of only the low energy photons is obtained by electronically subtracting the high energy image from the dual energy image with the data processor 34. Once both images are obtained, comparative dual photon processing techniques are used to make quantitative density calculations.

An additional feature of the embodiment of FIG. 3 is the replacement of the lens 22 of the FIG. 2 embodiment with a fiber optic reducer 44. The fiber optic reducer 44 is a focusing device consisting of a large array of optical fibers packed tightly together, and leading from the scintillating screen 20 to the CCD sensor 24. Near the CCD sensor 24, many of the fibers can be fused together, thus combining the signals present on individual fibers. The effect is a compression of the image from the input of the reducer 44 at the scintillation screen 20 to the reducer output at the CCD sensor 24. In this manner, the reducer 44 effectively focuses light from the scintillating screen 20 onto the CCD sensor 24 without the necessity of a lens for the focusing region.

Although they are shown together in FIG. 3, it is not necessary to use the fiber optic reducer 44 with the radionuclide source 40. Either element can be substituted into the configuration of FIG. 2 individually. The x-ray filter 42, however, should be used with the radionuclide source 40 to provide a dual photon discrimination capability. Note, however, that pulse height analysis can be performed in conjunction with the embodiment of FIGS. 10 & 11.

Figure 4:
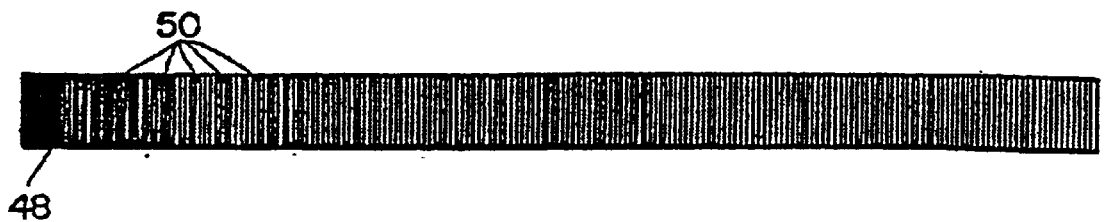
FIG. 4 illustrates another preferred embodiment for the scintillation screen employing a fiber optic plate.

FIG. 4 shows an alternative to the scintillation screen 20 of FIGS. 2 and 3. The screen 48 depicted by FIG. 3 is a scintillating fiber optic plate. The plate 48 is a fiber optic faceplate consisting of scintillating fibers 50 running through the plate. The fiber optic plate is optically interfaced to the CCD in essentially the same way as the scintillation screen 20 of FIG. 2, but the fiber optic plate 48 allows for greater quantum efficiency due to increased x-ray stopping capability.

Figure 5:
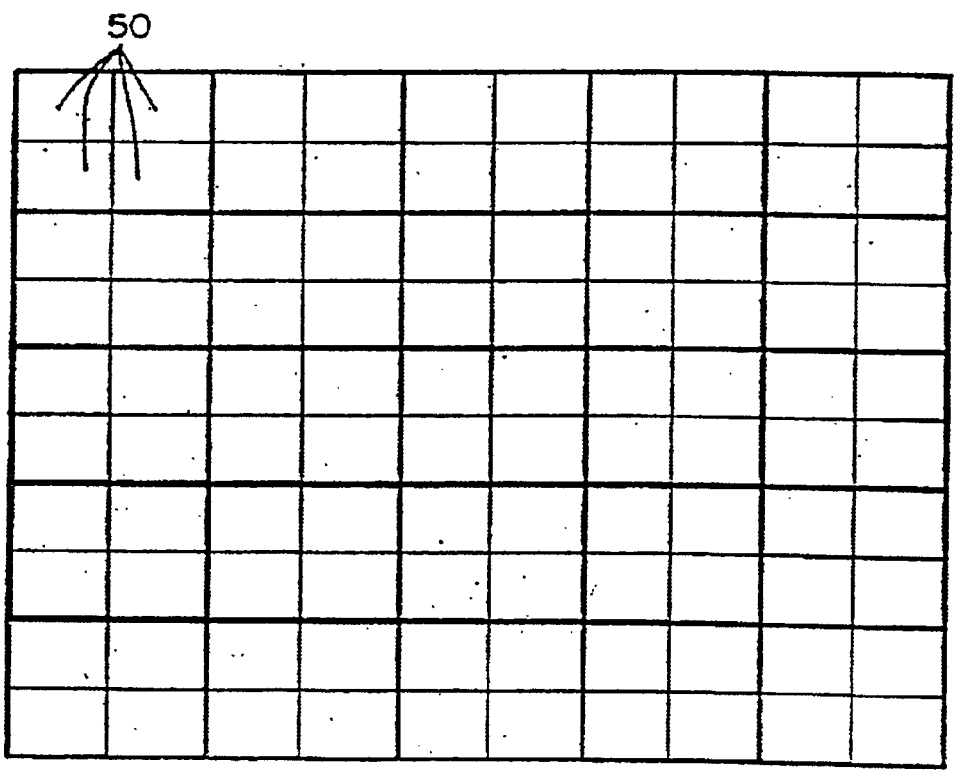
FIG. 5 is an illustration of the pixel array of a binnable area sensor.

Shown in FIG. 5 is a representation of the pixel array of the CCD sensor 24. The array shown in FIG. 5 is only 10×10 for illustrative purposes, and the actual array can be of different dimension. Each pixel in the array is an individual photosensitive element which contributes to the overall image detected by the array. A feature of the CCD sensor of the present embodiment is the capability of the pixels of the sensor 24 to be "binned" together. The binning of the pixel array refers to the ability of the sensor electronics to combine groups of pixels together to form "super pixels" which are then identified as single picture elements.

Charge is binned by combining charge packets contained in two or more adjacent potential wells into a single potential well during charge readout. Serial and parallel binning can be combined to perform two dimensional binning from any rectangular group of wells or detector elements.

The dark lines in the binnable array of FIG. 5 illustrate where individual pixels might be grouped together. For example, the four upper left hand corner pixels 50 can be binned together through control of the CCD sensor 24 to form a super pixel. The super pixel is then identified by the CCD electronics as a single pixel, the light intensity reaching each pixel 50 being averaged across the surface of the entire super pixel. In this manner, the dimension of the array can be electronically controlled. As can be seen in FIG. 5, if groups of four pixels are binned together across the 10×10 array, the overall array dimension becomes 5×5. Although the binning of the CCD sensor 24 reduces the resolution of the pixel array, the relative percentage of noise is also reduced, thus providing an improved signal to noise ratio.

The following x-ray data acquisition approach is an alternative to the one described above. In this approach, an image is acquired at high energy and the CCD is read in the normal non-binned mode. Due to the high penetration of the high energy beam through the body, the x-ray fluence exiting the body is high as compared to that of the low energy beam. Therefore, the resulting charge signal per CCD pixel is relatively strong. This image is stored as the high energy image. Also, this image is used in order to compute the area of the bone to be measured by manual selection of the region of interest or by automatic edge detection. Therefore, we take advantage of the high resolution image for greater accuracy in the measured bone area. Previously, the accuracy and precision of bone density measurements are limited to a great extent by suboptimal spatial resolution. The next image which is acquired with low energy is read out by the pixel binning approach, e.g., using a 2×2 pixel binning. The transmission of the low energy beam through the body is low as compared to the high energy beam. Therefore, in order to record a strong signal in each CCD pixel we must increase the radiation dose.

Alternatively, the binning technique can be used for the low energy in order to increase the signal to noise ratio and to a decrease the radiation dose. This dual mode acquisition procedure is a very powerful tool for improving the signal to noise ratio and lowering the radiation dose to the patient.

Figure 6:
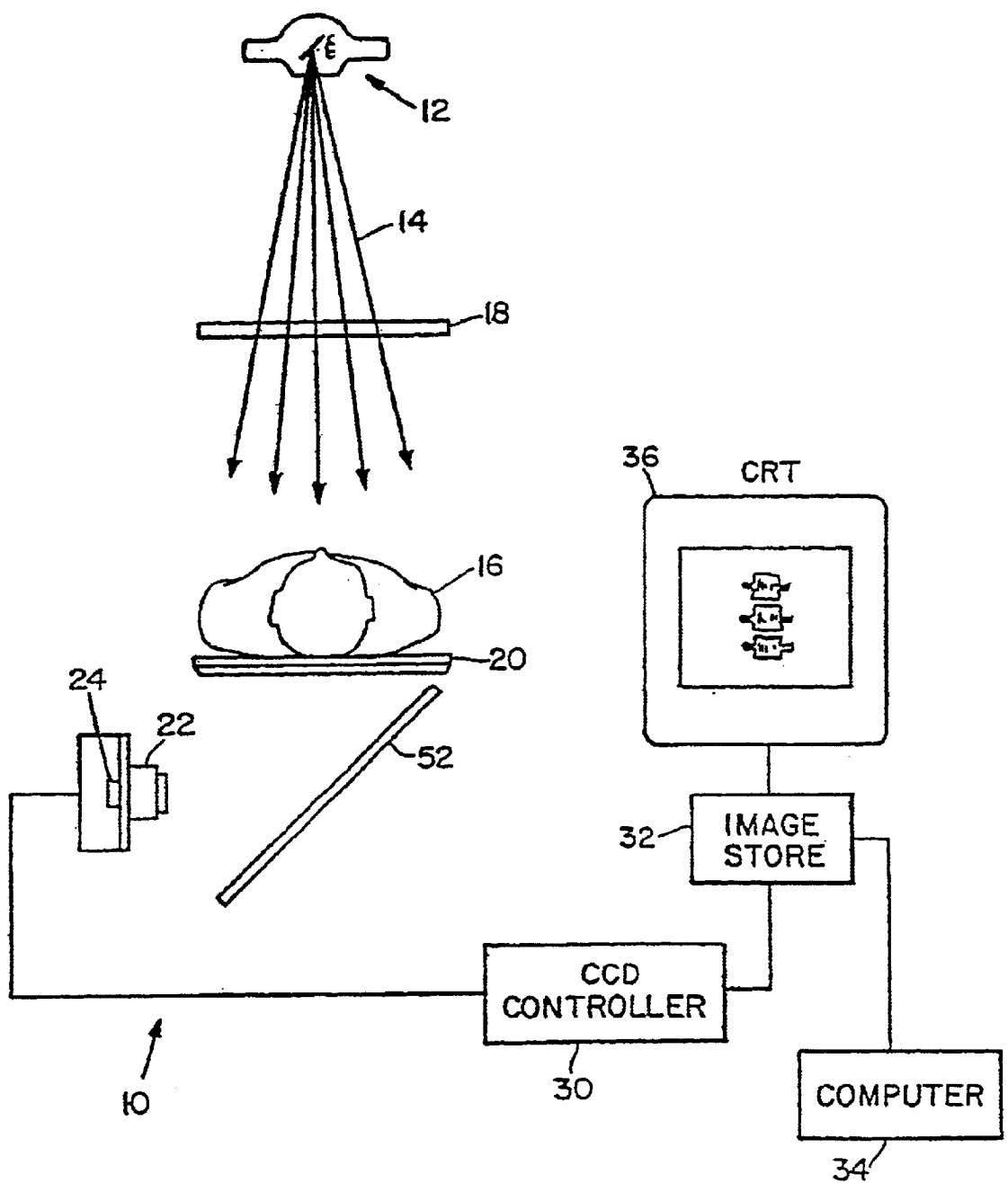
FIG. 6 is an alternative preferred embodiment to the bone density measuring apparatus of FIG. 2.

Although the arrangement of optical elements as shown in FIGS. 2 and 3 represent preferred embodiments, the functionality of the system is not dependent upon such an in-line type of optical transmission. FIG. 6 shows an alternative arrangement of optical elements where the CCD sensor 24 is set at an angle relative to scintillation screen 20, and mirror 52 is used to reflect the radiation given off by the scintillation screen toward the CCD sensor 24. Lens 22 is shown between CCD sensor 24 and mirror 52 and focuses the image onto the CCD sensor. However, the focusing of the scintillation screen image can take place before or after the image reaches mirror 52. In fact, the mirror itself may be shaped to provide focusing of the image from the scintillation screen 20.

Figure 7:
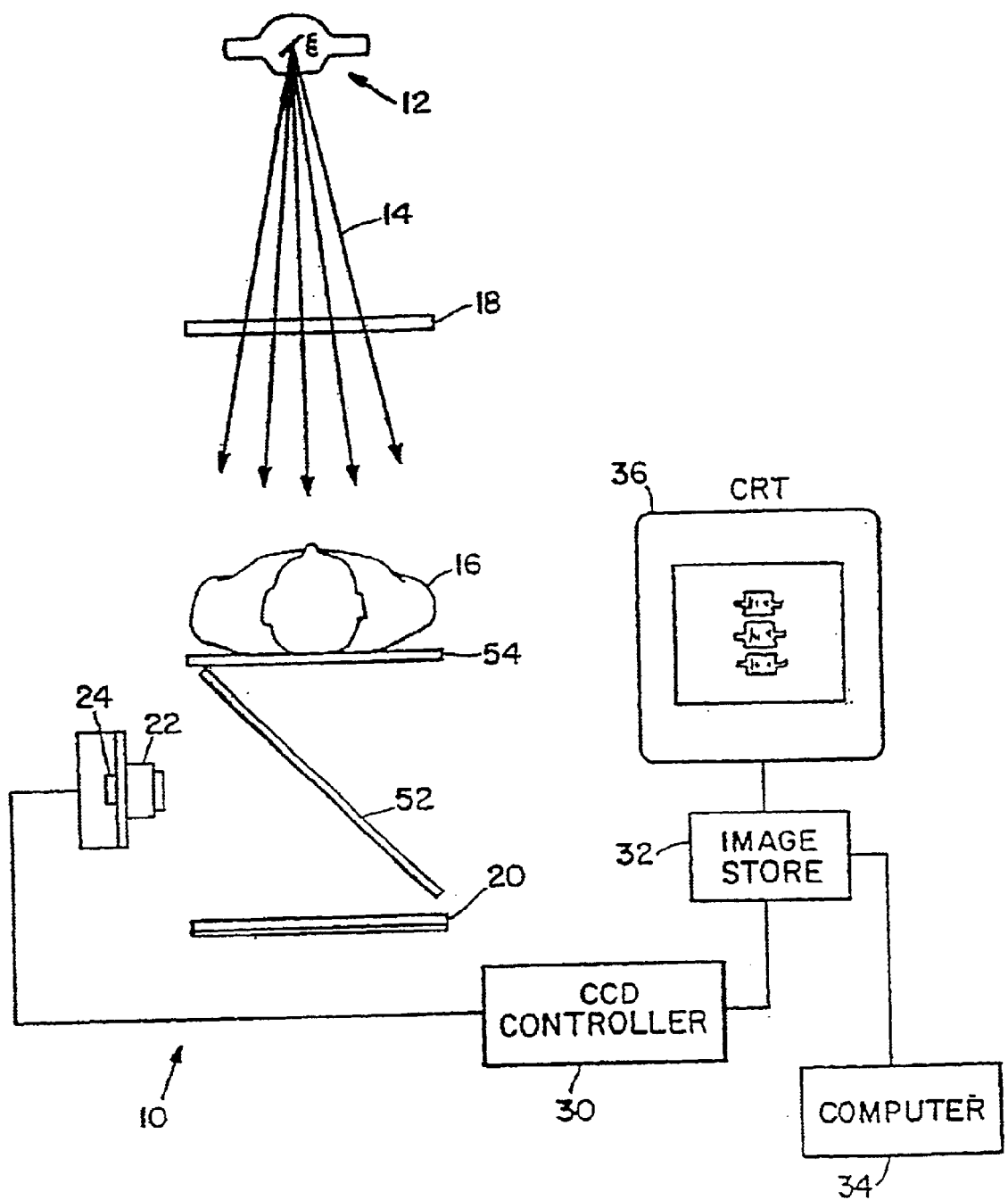
FIG. 7 is another alternative preferred embodiment to the bone density measuring apparatus of FIG. 2.

FIG. 7 shows another alternative arrangement of optical components. In FIG. 7 the subject 16 is suspended by a support 54 which is transparent to x-rays. The support 54 keeps the subject 16 elevated a distance above scintillation screen 20. As the x-rays reach scintillation screen 20, the screen 20 reradiates image data from the same surface upon which the x-ray radiation is incident. Mirror 52 is now aligned to reflect this image towards CCD sensor 24 which collects the image as focused through lens 22 to be processed by the CCD controller 30.

As with the arrangement of FIG. 6, the focusing of the image from the scintillation screen 20 may take place before or after it is reflected by the mirror 52, or may be focused by the mirror 52 itself. In addition, any of the optional elements previously discussed may be substituted into the arrangement of FIG. 5 or FIG. 7. This includes the x-ray absorbing screen 28, the anti-scatter grid, the fiber optic reducer 44, and the fiber optic faceplate 48.

A very effective, radiation dose-efficient approach for reducing x-ray scatter and increasing the dynamic range of electronically acquired x-ray images is the use of a slit-scan method. In this approach, a fan beam of x-rays is scanned over the patient and a linear array of detectors is used to detect the transmitted radiation. In typical applications the length of the detector restricts the width of the area that can be covered with one pass. Also, many small linear CCD or photodiode arrays are used to form a line of detection. This results in a rather complex detector assembly. If cooling of the detector assembly is required, it is difficult to accomplish for such an extended detector. Also, image intensification by using an electronic intensifier becomes difficult and very costly.

Figure 8:
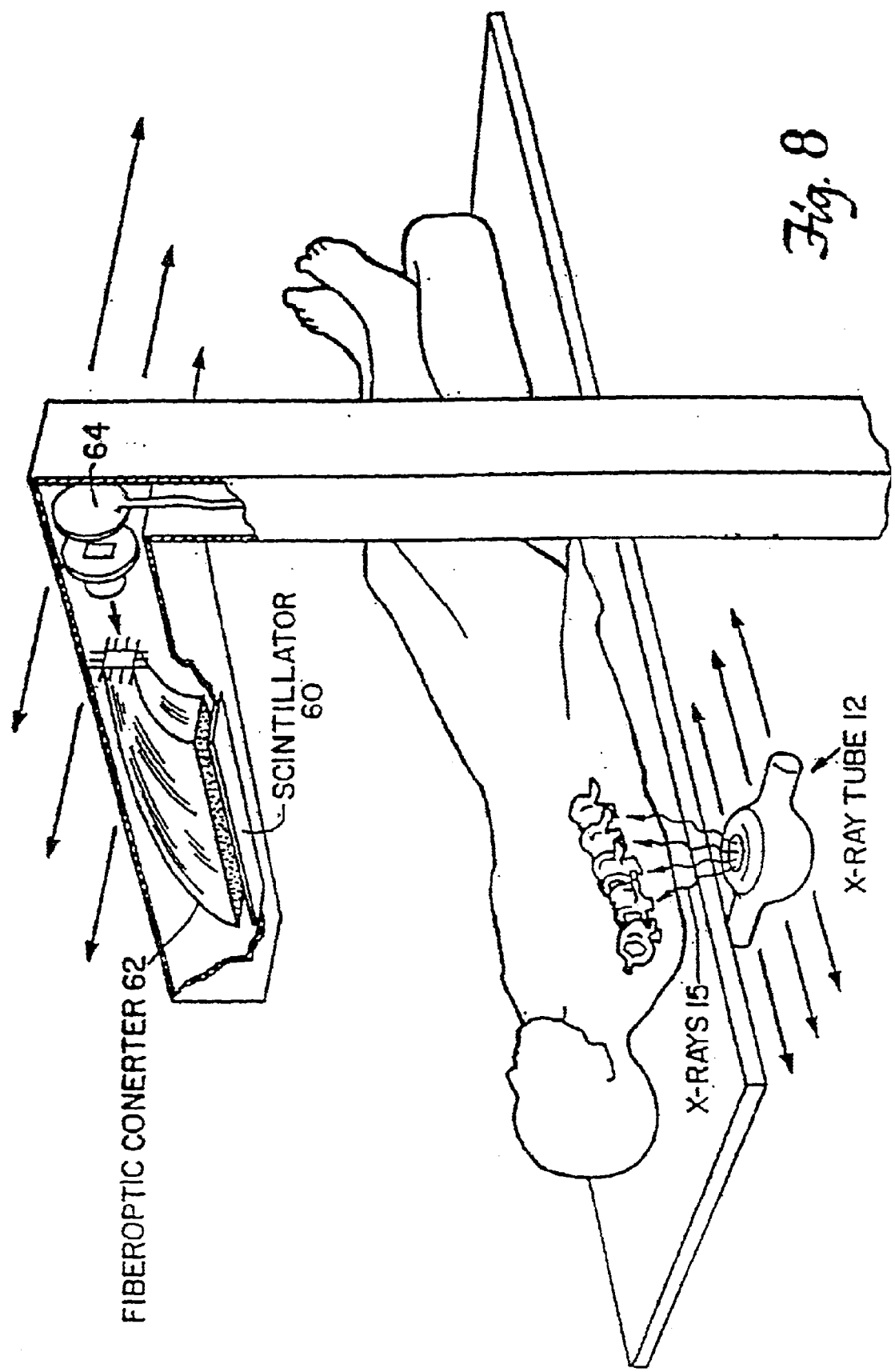
FIG. 8 is a perspective view of a scanning system of the present invention.

An alternative embodiment for dual energy bone densitometry takes advantage of the merits of slit-scan geometry without using a linear CCD or photodiode array. This approach is illustrated schematically in FIG. 8. An area CCD sensor 64 is used in conjunction with a line-to-area fiber optic converter 62. This converter can be made of flexible or rigid optical fibers with cladding of lower index of refraction than the core material. As shown in FIG. 8, the CCD 64 is divided into a number of rows and a fiber optic ribbon is optically coupled or bonded to each row. The coupling of the CCD 64 to the converter 62 can be accomplished using the various systems described in connection with other embodiments. An extramural absorber can be used to prevent light crossing from one fiber to another. The other ends of each ribbon are arranged in tandem to form a linear sensor. In front of the linear sensor (input end), an x-ray converting scintillator 60 is used such as gadolinium oxysulfide activated with terbium (GOS:Tb). Alternatively, a scintillating fiber optic plate can be used for improved quantum efficiency at higher energies. A linear x-ray sensor with a very compact area detector is employed with the slit-scan embodiment.

A typical linear detector of this type comprises a few ribbons in tandem along the length of the slit, and from one to a multitude of ribbons across the width of the detector slit.

In a typical example, consider a 512×512 pixel CCD where each pixel has an area of 20×20 microns. A fiber optic bundle with individual fibers of 60 microns in diameter is used for the embodiment. On the CCD each fiber will cover an area of approximately 3×3 pixels. Perfect alignment between each pixel and fiber is desirable but it is not essential for this application. Close packing of the fibers will result in an array of 170×170 or a total of 29,127 fibers covering the entire area of the CCD. Each ribbon of fibers corresponds to one row consisting of 170 fibers and covering approximately 512×3 pixels on the CCD. If all ribbons emerging from the CCD were arranged in tandem, the linear sensor would be approximately 175 cm in length. Alternatively, the ribbons can be arranged with a small number in tandem and a small number across the width of the slit. Using the above CCD, a 15.3 cm linear detector can be made with approximately 15 ribbons in tandem thus using only a small fraction of the CCD area.

Full use of the CCD area can be made by stacking the ribbons in groups of 15, (one ribbon per CCD row), thus creating a quasilinear detector consisting of an array of 2,550×11 fibers optically coupled to an x-ray scintillator. The dimensions of this slit detector will be 153×0.66 mm with a total sensing area of 1.0 cm2. It is important to note that the total sensing area of the slit must be approximately equal to the total area of the CCD and the linear dimensions of the fiber optic output must be approximately the same as the linear dimensions of the CCD. A wider or longer slit will result in a larger area at the output end. In this case, a larger CCD can be used or a fiber optic reducer optically bonded between the fiber optic converter and the CCD. Alternatively, the converter itself can be tapered to match the size of the CCD. For higher spatial resolution the fiber optic converter is made with optical fibers of smaller diameter (5–6 microns).

If higher signal amplification is required for some high detail low dose applications, a proximity focused image intensifier can be optically bonded between the fiber optic taper and CCD or between the fiber optic converter and fiber optic taper. The image intensifier can be a proximity diode type or a microchannel plate device, both commercially available. Alternatively, an integral assembly of CCD and intensifier can be used commonly called an "intensified CCD". Another approach is to use a lens coupling between the output surface of the fiber optic converter and the intensified or non-intensified CCD.

Cooling of the CCD can be accomplished easily by a thermoelectric cooler. Cooling is required only when very high contrast resolution is required and the image acquisition time is relatively long. If the CCD is read out at 500 kHz ($5 \times 10^5$ pixels/sec), an area of 150 mm×150 mm of the subject can be scanned in approximately 114 seconds (approximately 2 minutes). Faster scanning is attainable by increasing the readout rate of the CCD.

Figure 10:
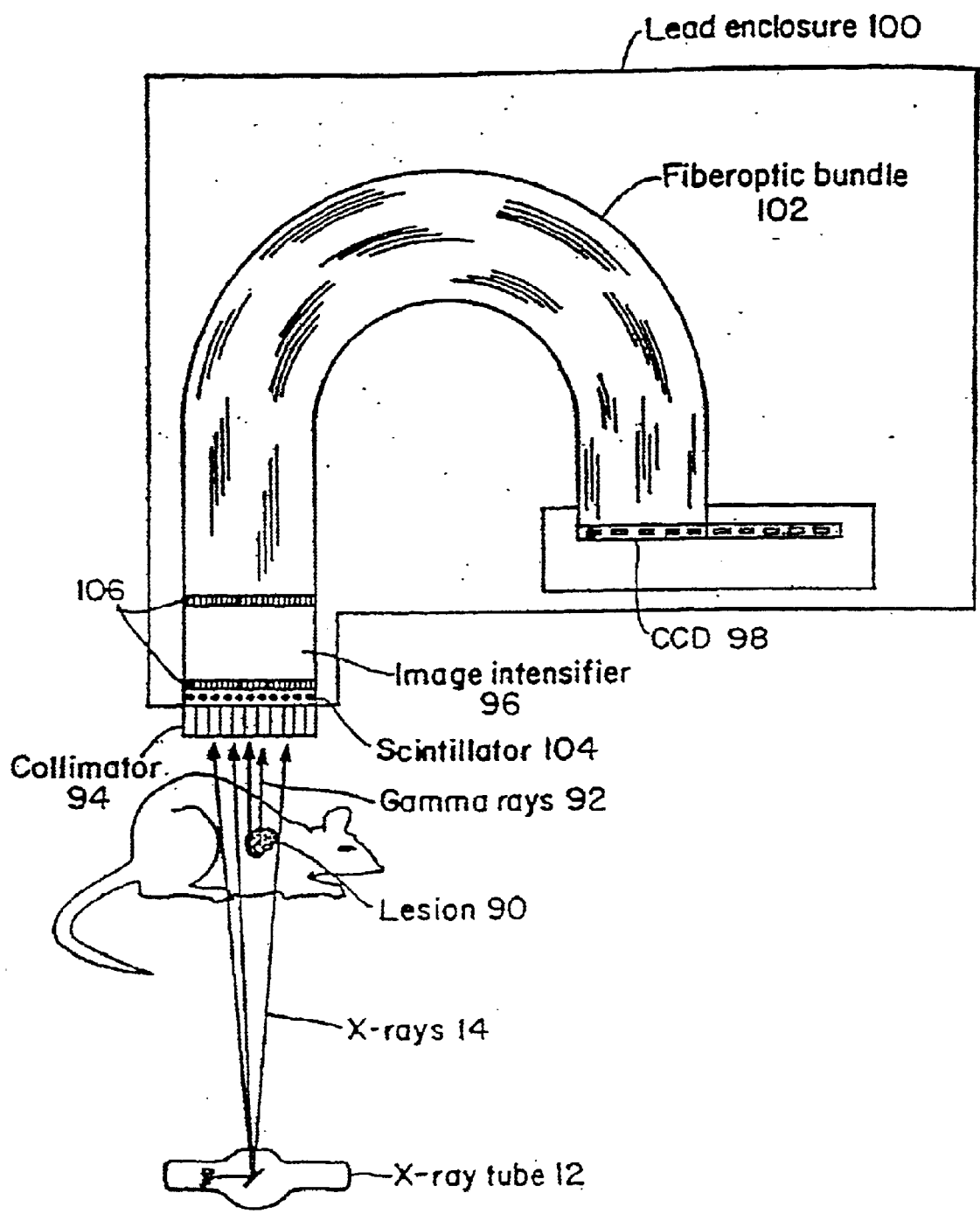
FIG. 10 is a schematic sectional view illustrating a frame transfer CCD used for both emission and transmission studies.

Alternatively, a frame transfer CCD such as the one illustrated in FIG. 10 can be used for faster scanning. This device uses one half of its sensing area for storage and not for sensing. In this way the transfer of the image from the sensing area 91 to the storage area 93 is accomplished in a few milliseconds. A smaller CCD such as a 128×128 or a 64×64 element could be used for this purpose in a similar arrangement as with the 512×512 CCD. Also, larger area CCDs can be used for this purpose. Pixel binning as described previously can be applied in this detection approach. A Gadolinium-153 (Gd-153) radiation source can be used as described in previous sections in place of an x-ray tube. The Gd-153 source is a small pellet or a collimated line source parallel with the long dimension of the detector.

The line to area conversion design enables us to remove the CCD from the direct path of the x-ray beam, thus it allows for easy shielding of the CCD from direct x-ray interactions. This prolongs the useful life of the CCD and it alleviates the "snow" effect which results from direct interactions of x-rays with the sensor. Moreover, this approach allows for greater light transport efficiency between the scintillator and CCD than lenses or fiber optic tapers. Note that the pixel binning approach enables the operator to select the desired spatial resolution and contrast without any mechanical modifications on either the x-ray beam or the detector collimator. The pixel size of the detector which determines resolution and contrast can be controlled by a command from the computer. This x-ray imaging modality can be used very effectively to optimize the scan depending on patient size, and medical history.

An alternate approach provides an improved rectilinear scanning method for quantitative x-ray radiography. In this embodiment, a two dimensional CCD optically coupled to a scintillator is used as the detector of x-rays in a rectilinear scanning mode. The CCD may be a full frame or a frame transfer device. The frame transfer CCD will enable faster data scanning and acquisition.

The CCD scintillator assembly is extremely critical to the performance of the system. Direct optical bonding of a polycrystalline scintillator such as gadolinium oxysulfide with the CCD is possible but this approach is not efficient in shielding the CCD from direct x-ray interactions. If the thickness of the layer is increased the spatial resolution of the x-ray images degrades due to light diffusion. The use of a scintillating fiber optic plate between the polycrystalline scintillator and the CCD provides a solution to this problem.

A scintillating fiber optic plate is a fiber optic faceplate designed to convert x-rays or U.V. light into green light with peak emission at about 550 nm. This faceplate is manufactured with extra mural absorber to prevent light diffusion between individual fibers. The area of the scintillating fiber optic plate must cover the CCD completely. The desirable thickness depends on the energy of the x-ray radiation. A thickness of 5 to 10 mm is preferable but a thinner or thicker plate can be used. The use of a very thick scintillating fiber optic plate such as 10 mm or 20 mm will eliminate virtually any undesirable direct x-ray interactions with the CCD. The scintillating fiber optic plate can also be used without the thin layer phosphor. However, the combination of the two will produce better image quality at a reduced radiation dose to the patient. Alternatively a conventional fiber optic plate can be used as a substrate to the scintillating fiber optic plate. The optical coupling of the polycrystalline phosphor on the fiber optic can be accomplished by direct deposition techniques or by using an optical adhesive.

In an alternate approach, a bent fiber optic bundle can be used between the scintillator and the CCD. The geometry of the bent bundle allows for extremely effective shielding of the CCD from extraneous x-ray radiation. A lens coupling between the CCD and the fiber optic converter can also be used. For improved sensitivity, a proximity focused image intensifier, an image diode or microchannel plate can be used at the input end of the fiber optic or between the fiber optic bundle and the CCD. A preferred approach is to use the intensifier at the input end. A scintillator can be optically bonded to the input of the intensifier or an intensifier with a scintillating fiber optic input plate can be used.

The x-ray tube is aligned in a C-arm configuration with the detector. The x-ray beam is approximately congruent with the area of the detector which is approximately 1×1 cm at the detector plane. As x-rays are transmitted through the patient, some (20%–60%) are absorbed by the primary polycrystalline scintillator producing visible light. This light is transmitted through the optically transparent fiber optic faceplate in the direction of the CCD. The x-rays not interacting with the primary scintillator will be absorbed by the fiber optic faceplate. If a scintillating fiber optic faceplate is used, these x-rays will be absorbed in the fibers thus producing additional scintillations. Therefore, the scintillating fiber optic plate acts as a light conduction device, x-ray shield, secondary x-ray detector and an x-ray signal amplifier.

Upon interaction of the x-ray induced light with the photosensitive surface of the CCD an electron charge is generated which is proportional to the number of x-ray interactions in the scintillators. The cumulated charge on the CCD is then read out. However, in this rectilinear scanning mode, each CCD readout will correspond to a small segment of the total image, approximately one square centimeter. Therefore, the entire image is acquired by spatial additional of each image segment. For example, if a 15×15 cm field is covered and the sensor area is 1.0×1.0 cm, 152 (225) segments must be acquired and synthesized. A 512×512 pixel CCD operating at 500 kHz will read out each segment in 0.5 seconds and will require about 2 minutes for the entire scan at a scan speed of about 2 cm/sec. Faster scanning is attainable by increasing both the scanning speed and the readout rate of the CCD.

A dual-energy scan will be acquired by first scanning the entire area at high tube potential, typically 130 kVp without binning and then repeating the scan at low tube potential, typically at about 70 kVp with binning. An automatic slide mechanism places high aluminum filtration for the high energy beam and less filtration for the low energy beam as described previously. The images of each energy level are stored in the computer for subsequent dual photon analysis. Pixel binned acquisition will be possible at both energies for improved precision. Where both high and low energy images are identically binned, this produces an exact correlation between the images produced. A third high energy-high resolution image can then be used to define the outline of the object being scanned. Note that a gadolinium isotope source with a shutter can be used.

Alternatively, the energy level of the tube can be switched from low to high for each segment of the acquisition and each segment representing high and low energy is stored for subsequent analysis.

An alternate approach employs light intensification from the screen to the CCD sensor. In this approach, an electrostatically focused image intensifier (In FIG. 2) is employed as the primary detector in place of the scintillating plate. This intensifier preferably employs Cesium iodide input phosphor with an approximate diameter of 15 cm and thickness of 0.3–0.5 min. The high voltage of the image intensifier tube can be reduced to approximately half the normal value. A reduction in the image intensifier accelerating potential will contribute to an improvement in the image contrast characteristics and dynamic range of the device. The CCD sensor is optically coupled to the output phosphor of the image intensifier by a fast lens with an f-number of about 1:1.0. Due to the high signal intensification, cooling of the CCD is not essential but it can be applied if very low thermal noise levels are desirable. The use of an intensifier allows for the use of a CCD with lower noise performance characteristics, thus lowering the cost and complexity of the instrument.

Ideally, the detected signal is produced by x-rays that have been transmitted through the body without any scatter interaction. Detection of large amount of scatter events will result in non-linearities and in a reduction in the dynamic range. Effective suppression of scatter is accomplished by using a small field of view, typically 10 cm×10 cm and by using a air gap (approximately 20 cm) between the patient and the scintillating plate. Alternatively a small field of view can be used in conjunction with a linear or crossed antiscatter grid.

Figure 9:
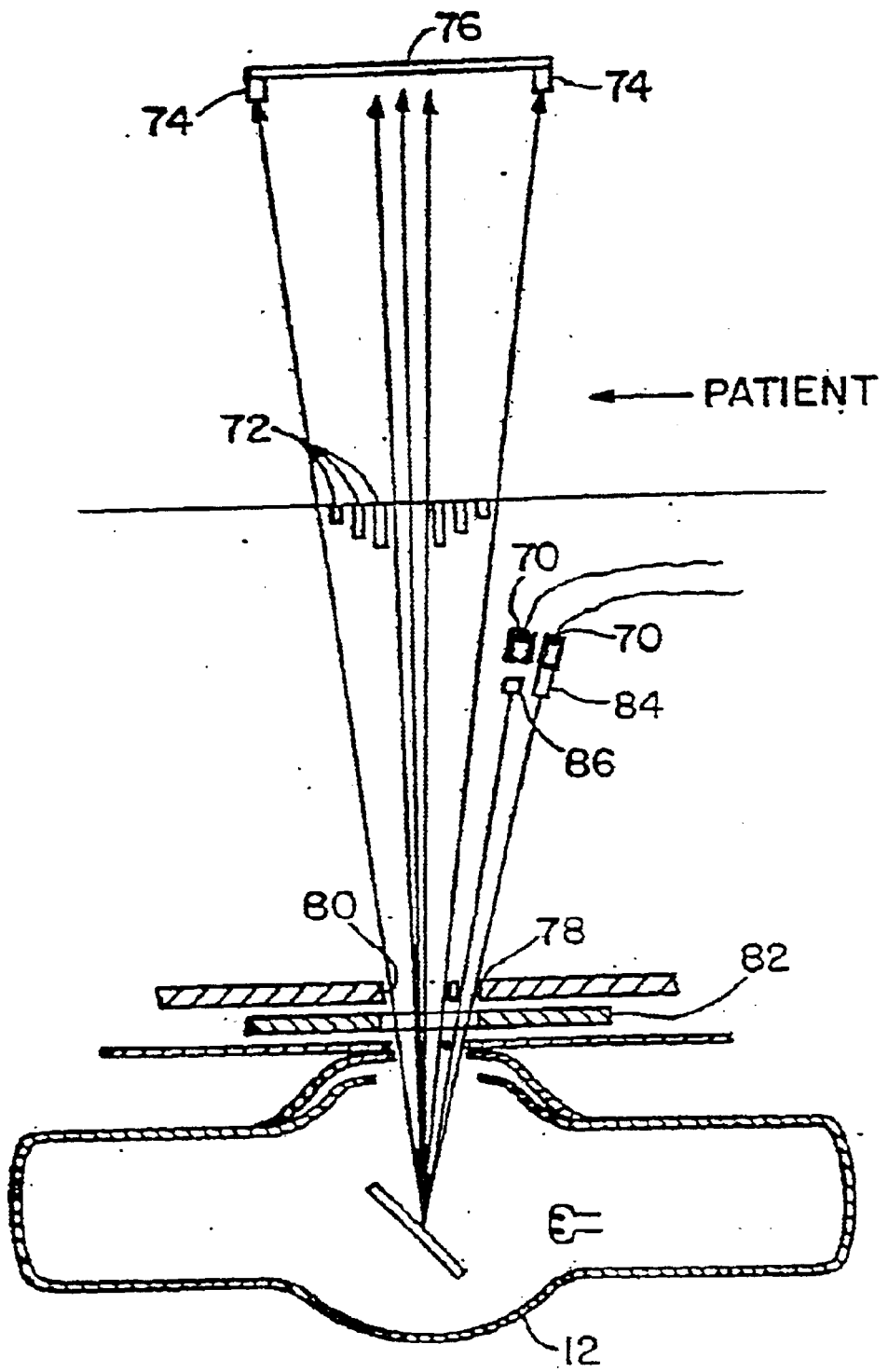
FIG. 9 is a schematic sectional view illustrating the sensor control system.

An internal instrument stability control system has been incorporated to provide a means of automatic compensation for any instabilities in the x-ray tube potential and current. The stability control device is not essential for the operation of any of the described techniques but it provides better reliability and precision in the measurement of bone density. A schematic representation of the proposed device is shown in FIG. 9. The output of the x-ray tube 12 is monitored by a pair of x-ray sensors 70 placed at a secondary x-ray beam port 78 adjacent to the main beam port 80 near the tube window. The sensors can be silicon diodes, cadmium telluride radiation sensors or any other solid state x-ray sensor. Alternatively, a pair of compact photomultiplier- scintillators or a photodiode scintillator assembly could be used. Both detectors operate in the charge integration mode and the detected signal is continuously monitored as a function of time during the entire' scan for each energy. This time varying signal is digitized and stored in the computer memory. The change in the filtration of the secondary beam with energy is identical to that in the main beam because it is controlled by the same filter changing mechanism. As described further in connection with FIG. 12 the sensor system can be used to normalize the detected information or to control operation of the x-ray source to prevent or reduce unwanted variations in the source output.

In front of one of the sensors 70 an amount of polymethyl methacrylate 86 is placed to simulate an average thickness of soft tissue. In front of other sensor 70 an amount of bone simulating material 84 is placed in an amount equivalent to that encountered in the spine or femur. Various hydroxyapatite-epoxy mixtures are commercially available for bone simulation in x-ray imaging. Therefore, a secondary detection system with a bone standard of known density and a soft tissue equivalent thickness is provided in this embodiment.

The signals from each sensor 70 can be used to compute the density of the bone internal standard as a function of time during the scan. Any deviations from a constant density of this standard are due to changes in either the energy or intensity of the x-ray emission. Each value of bone density computed in the patient scan corresponds to a computed value of the bone standard. Therefore, each computation of bone density derived from a pair of high and low energy CCD frame acquisitions can be corrected or normalized by using the deviation from the density of the internal standard. For example, if the value of the bone standard during the rectilinear scan deviated by plus 3% in a given area of the image, the computed bone density of the patient scan must be corrected by that amount in this area. This internal reference approach can be used with all stationary and scanning embodiments described herein.

In conjunction with the above calibration approach, a number of strips 72 (square rods) of bone simulating epoxy material, or aluminum of equivalent x-ray absorption are placed under the table 73 which run in the direction of the scan for the slit scan approach. Each linear strip has a different thickness or bone equivalent density. As the x-ray tube and detector assembly is scanned over the area to be tested, each set of rods are scanned and their density computed. The consistency of the measured densities of these rods is used to ensure proper operation of the system. This set of standards can be placed anywhere from the x-ray exit port 80 to the edges 74 of the detector 76.

The imaging of radionuclide distributions in biological tissues or specimens is a routine task performed in virtually all biomedical research laboratories by the well established technique of autoradiography. In this procedure, a thin slice of a specimen is placed in contact with photographic film thus allowing the radiation from the specimen to expose the film. Subsequently, the film is processed by standard chemical development techniques, manually, or by using an automatic processor. Frequently, an intensifying screen is used in order to enhance the absorption efficiency of the image receptor and for a reduction in exposure time. Intensifying screens are especially useful when images of relatively high-energy gamma or x-ray emissions are recorded (20–200) keV. Also they can be useful for high energy electrons.

Autoradiography produces images reflecting the biodistribution of a radionuclide and it has been established as a powerful tool in many biomedical disciplines. Its major shortcomings relate to problems with quantization of the relative or absolute concentration of radionuclide in an area of interest. This difficulty arises from the non-linearity of photographic film typically used and in reciprocity law failure when intensifying screens are used. Moreover, the development temperature, and in general, the condition of the processing chemicals have an influence on the film fog level and contrast. All these factors render quantization a very difficult and time consuming task which becomes vulnerable to many uncertainties in quantitative autoradiography. Despite these problem, several investigators have digitized film autoradiographs by using microdensitometers or video cameras for both quantization and image enhancement.

In autoradiography, the image represents areas where the radiotracer has been extracted. The anatomical information on the original tissue slide is not transferred with great detail in the autoradiograph. For proper interpretation, it is necessary to observe the tissue slide and autoradiograph side by side in order to correlate radiotracer distribution with anatomy. Often it is necessary to superimpose the slide with the autoradiograph in order to identify the exact anatomic location of the radiotracer. In this process the accuracy in assigning an anatomic location to the tracer is severely compromised.

One of the most important problems with autoradiography is the long period of time required in order to expose the film. In most applications this time ranges from a few hours to several days, even weeks in some cases. Therefore, the technician may have to wait for a few days in order to find out whether an exposure has to be repeated.

Autoradiography does not relate to in vivo imaging of radionuclide distributions in humans or animals. Rather it relates to detecting radioactive distributions in excised samples. All available film-screen image receptors have extremely low quantum efficiencies for most gamma emitters commonly used for this purpose. Moreover, the presence of a large volume of tissue results in enormous amount of gamma ray scatter which will reach the image receptor and degrade the contrast and spatial resolution. The film-screen receptors do not have energy discrimination capabilities, therefore scattered events cannot be rejected. The use of a collimator to suppress scatter will result in a dramatic reduction in geometric efficiency.

Thus the present invention, in its various embodiments, provides an effective means for performing autoradiography by providing a compact device that performs the data acquisition for autoradiography quickly and can superimpose both emission and transmission studies to correlate the emission image with the anatomical features of the object under examination. The embodiments described in connection with FIGS. 10 and 11 below can be used to perform autoradiographic procedures.

Radionuclide imaging of humans and animals is performed on a routine basis by using the Anger camera, most commonly referred to as a "Gamma Camera". The gamma camera has a quantum efficiency in excess of 50% for the most commonly used radionuclides and it has the capability of discriminating scatter from primary photons by pulse-height analysis of each detected photon. The intrinsic spatial resolution of the gamma camera is approximately 3.5 mm. The total spatial resolution of the camera, including the degradation due to its collimator, can vary from 5 mm to 12 min. Modem gamma cameras can detect photons at the rate of 25,000 counts per second (cps) without significant dead time losses. At higher count rates, significant deviations are observed between true and detected events. This is due to limitations inherent in the design of both the detector assembly and processing electronics.

The following presents a further embodiment relating to imaging of radionuclide distributions in tissue samples and in vivo quantitative imaging of humans and animals. This procedure employs a charge-coupled device to detect and process information to provide, in essence, a compact "gamma camera" using a highly sensitive stationary (or scanning) detector to conduct both emission and transmission studies at count rates up to 106 of the object being examined.

Existing gamma cameras have limited spatial resolution, limited capability to perform in high count-rate conditions and it cannot be used to record x-ray transmission (radiographic) images with any degree of acceptable detail to satisfy radiographic imaging standards. Therefore, the recording of a high quality radionuclide (physiologic) image and a radiographic (anatomic) image with the same detector for accurate correlation of the physiologic and anatomic image remain difficult. Where very high detail is necessary, the gamma camera is generally not capable of producing better than 5 mm resolution even under the most favorable conditions. Therefore, the imaging of small parts of the body or imaging small animals like mice cannot be performed with any reasonable detail using the gamma camera. This also applies for the imaging of tissues containing radioactive materials.

The following procedures enable the acquisition of high detail radionuclide images and the option of combining them with the x-ray radiographic images with the same detector. This approach employs a novel acquisition scheme that enables imaging spectroscopy of gamma rays, x-rays or nuclear particles by using a CCD. CCDs have been employed in the past without a scintillator for imaging spectroscopy of very soft x-rays, up to the energy levels of about 6–9 keV. However, above this energy, the CCD becomes virtually transparent to x-rays or gamma-rays. Generally, scintillators have not been used in conjunction with a CCD for imaging spectroscopy because it is believed that the conversion from gamma-rays to light will destroy the useful information carried by the interacting gamma-ray or x-ray. Therefore, imaging spectroscopy of gamma-rays or x-rays in the energy range of about 10 keV to 2,000 keV with a CCD has not been explored. Also, alternating the mode of operation from a counting, energy sensing detector to an integrating detector for radionuclide and radiography, respectively, presents a useful procedure for imaging spectroscopy. Note, however, that the counting procedure can also be used in certain x-ray transmission measurements to measure the energy thereof.

When light interacts with the sensitive surface of the CCD, it generates a charge which remains stored in the pixel where this interaction occurred. As with previous embodiments the magnitude of the charge is directly proportional to the detected intensity of light. Each pixel is represented by its two-dimensional coordinates and by an intensity value. The energy required to produce an electron in the sensitive silicon surface of the CCD is about 3.65 KeV.

This value enables the determination of the energy of detected photons if the system can either detect one photon at a time, or if the number of the photons detected per pixel is known. This provides for imaging of radionuclide distributions with a simultaneous measurement of the energy of the detected events. This procedure is termed "Imaging Spectroscopy" and provides a technique using gamma rays, beta-rays, and x-rays in conjunction with CCD technology.

The upper energy limit of soft x-ray imaging is between 5–10 keV. At 10 keV, the quantum efficiency of a CCD is approximately 5% and it diminishes rapidly at higher energies. The small fraction of the total number of events interacting with the CCD will result in a high partial energy transfer to the sensor with losses in proportion with the energy and the signal. Therefore, when the CCD is used as the primary detector of high energy photons or particles, it is virtually unusable for performing imaging spectroscopy. The following procedure provides high resolution imaging spectroscopy using a CCD that is suitable for many applications including position emission tomography and nuclear particle imaging.

A schematic of the device is shown in FIG. 10. An important component of this device is a CCD 98 with low readout noise, high charge transfer efficiency and dark current levels. A CCD with less than 10 electrons/pixel (RMS) readout noise is suitable for this purpose. The dark current can be reduced to less than 0.6 electrons/sec at −40° C. by a compact thermoelectric cooler.

In one embodiment of this method, a thin scintillator 104 is used as the primary detector of x-rays. One such scintillator can be a layer of gadolinium oxysulfide or thallium activated cesium iodide or any of the commonly available phosphors. The scintillator 104 is bonded to a fiber optic faceplate 106 and the faceplate is bonded to an image intensifier 96. The intensifier is bonded to a second faceplate 106 that is bonded to bundle 102. Optical bonding of this type is well established. To further illustrate this embodiment the sensitive area of the scintillator 104, faceplates 106, image intensifier 96, fiber optic coupler 102, and CCD 98 have, identical dimensions. Note that a collimator 94 can be mounted on the lead enclosure 100 and is used during the transmission study, and depending on its configuration, can also be used during the emission study. Note that the collimator 94 can optionally be removed during emission studies.

When an x-ray photon within the rays 14 interacts with the scintillator 104, it produces light with intensity which is proportional to the energy of the x-ray. This light is transported through the fiber optic faceplate 106 and interacts with the CCD 98. The interaction of optical photons in each CCD pixel will produce a number of electrons in direct proportion to the number of optical photons and to the energy of the detected x-rays 14 or gamma-rays 92 that are produced by the isotope that has collected in the lesion 90. Isotopes commonly utilized include TC 99 m or I-125. The following example as a first order approximation of the expected energy resolution from the detector.

A 60 key x-ray interacts with the scintillator resulting in 3000 optical photons. Approximately one half of these photons are emitted in the direction of the CCD. Assuming a Lambertian distribution of the emitted photons from the screen, the transmission through the fiber optic plate is approximately 40%. Therefore, 600 optical photons will be arriving at the CCD. The quantum efficiency of the CCD is approximately 40%, therefore only 240 photons will be detected in one pixel.

It can be shown that the energy resolution can be in the order of 10% which is approximately twice that attained with conventional NaI-crystal spectrometers at this gamma-ray energy.

Figure 11:
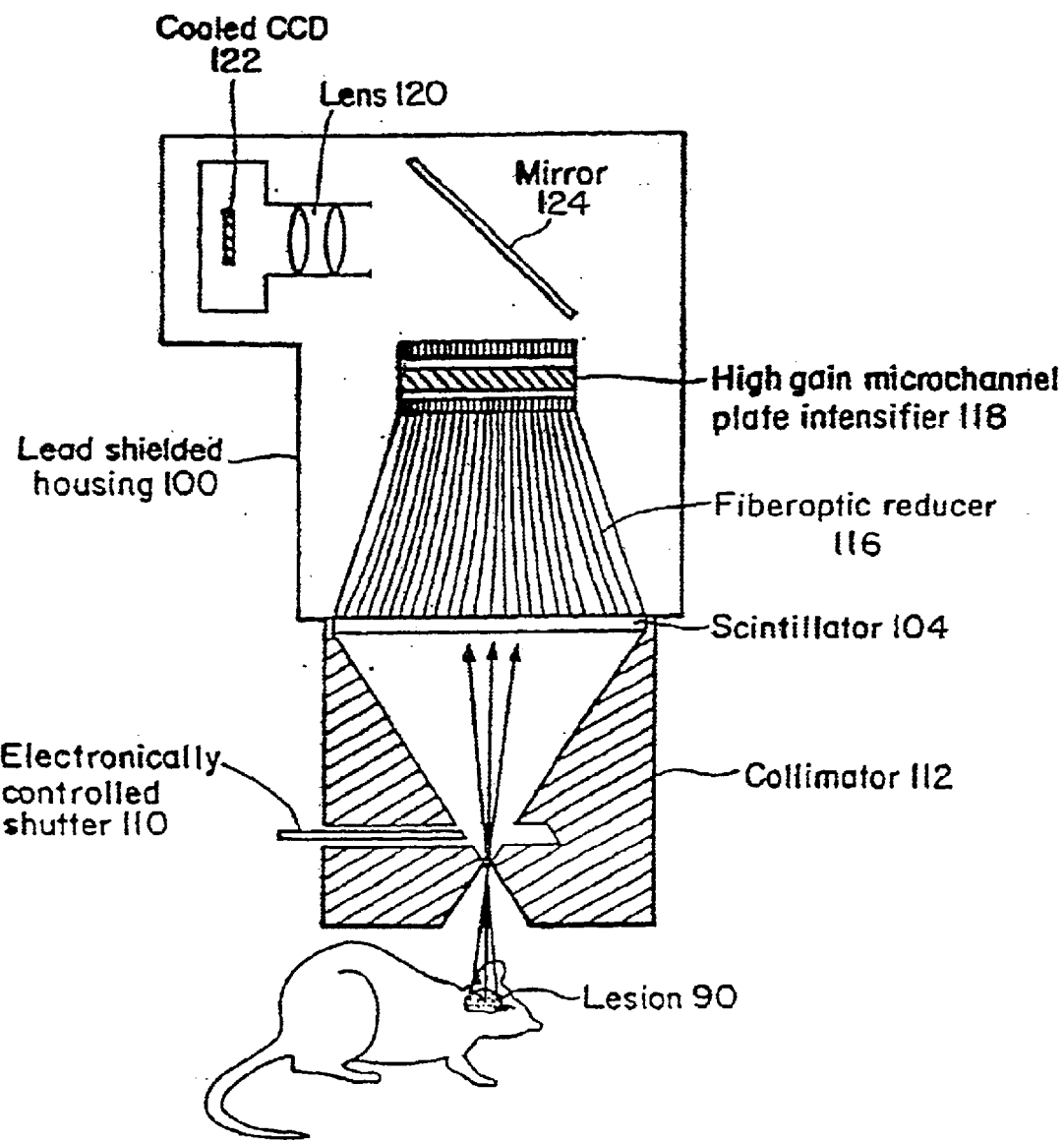
FIG. 11 is a schematic sectional view of a CCD imaging system for both emission and transmission studies.

FIG. 11 depicts an alternative embodiment in which a "pin hole" collimator 112 with shutter 110 is used in performing an emission study of lesion 90 or any selected organ. The emission from the lesion or organ impacts the scintillator 104, into housing 100, through the fiber optic reducer 116, coupled to the intensifier 118, and than directed off mirror 124, lens system 120, and onto a cooled CCD 120.

This procedure produces radionuclide scintigraphy with spatial resolution in the order of about 1 millimeter or less, and transmission images with resolution in the order of 0.2 millimeters. The spatial resolution and sensitivity of the detector will be selectable for both emission and transmission modes via pixel binning. The detector operation will be selectable for pulse-height analysis or integration. For x-ray transmission imaging, the integrating mode of operation is preferred. Note that during x-ray transmission imaging, the pin hole collimator will be removed. Emission imaging of thick tissues requires a collimator, either a multihole type or a pinhole collimator. Very thin specimens can be imaged without a collimator by placing them very close to the scintillator.

This camera has the capability of detecting very high count rates. In conventional gamma cameras, each x-ray photon interaction occupies the entire scintillator and electronics for a period of time of 1 to 8 microseconds after it is detected. In the present method, due to the multiple detectors, higher count rates can be handled due to the multiple detectors, and higher count rates can be handled without using a scintillator with short decay time. Count rates up to 106 counts per second can be acquired with very low probability (less than 1%) of detecting 2 gamma ray events in one pixel when operating in the pulse-height analysis mode.

Note the scintillator can be bonded directly on the fiber optic bundle without the use of an image intensifier. Also, the scintillator can be bonded directly on the CCD without the use of a fiber optic bundle. A frame transfer CCD is a preferred approach, but a full frame CCD can be used.

The following "shutter" methods can be used (a) a frame transfer CCD; (b) a gated image diode, or microchannel intensifier; or (c) a liquid crystal shutter with very thin window or fiber optic window. The liquid crystal shutter can be positioned between the fiber optic bundle and the scintillator.

Note that the system has applications for small animal imaging, skeletal imaging, monitoring of fracture healing, thyroid scintigraphy, Bremsstrahlung imaging of beta emitters within the body (radiation synovectomy), intraoperative imaging probe, radionuclide angiography, small parts imaging, and pediatric nuclear imaging.

Figure 12:
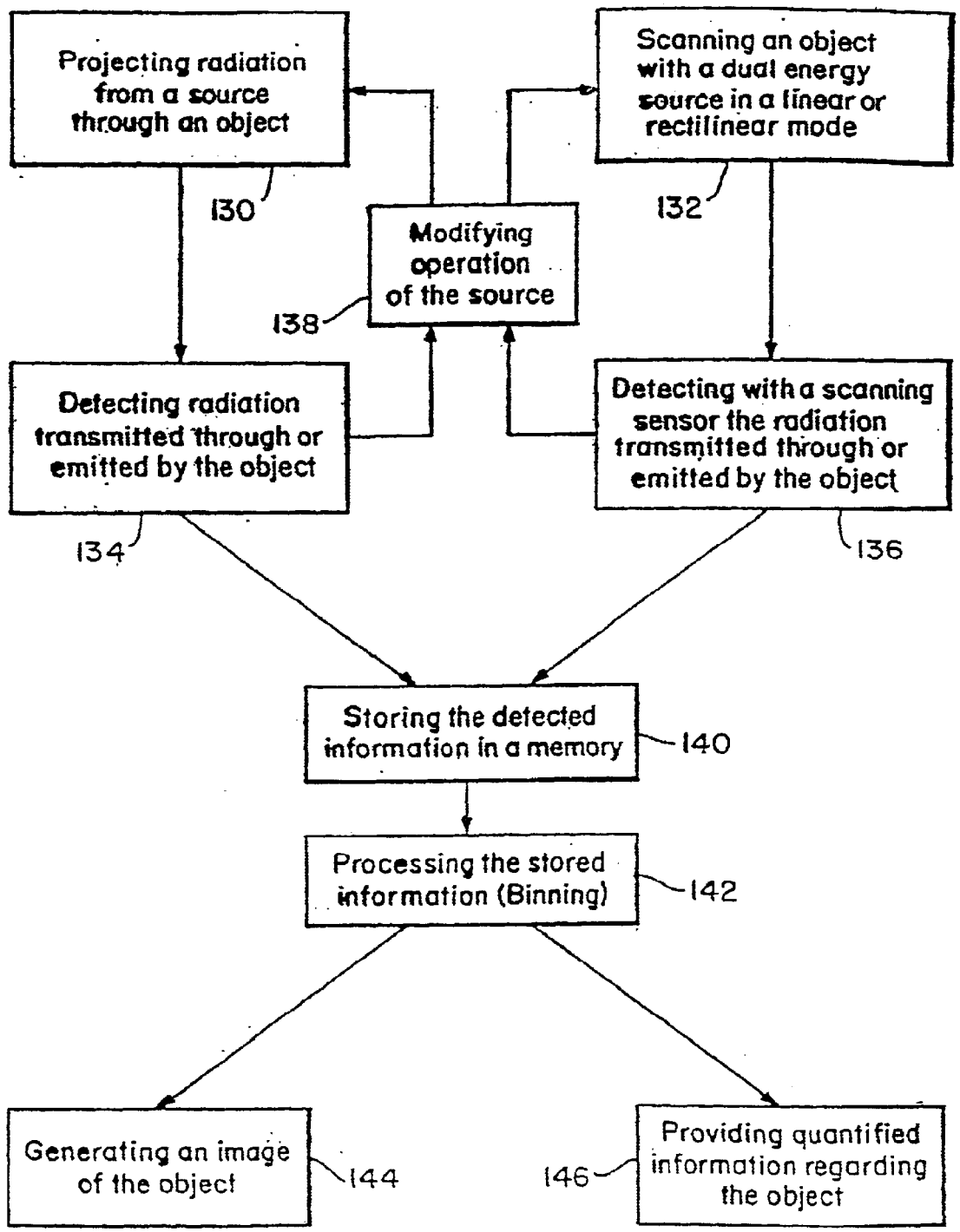
FIG. 12 illustrating a process flow sequence that is used in performing the imaging methods of the present invention.

FIG. 12 illustrates in schematic form several methods that can be used in performing quantitative imaging in accordance with the various embodiments of the invention.

Note that one can use either a stationary source and detector to project radiation 130, or a scanning source and detector assembly to scan the object being examined 132.

Both stationary and scanning embodiments utilize a CCD detector that transfers the detected information to a memory 140. The information can be binned or processed 142 to accomplish various tasks. This processing can include the application of software modules to correct for non-uniformities in the source or collection components, or to identify events where light from one gamma-ray interaction has spread to a number of neighboring pixels. Clusters of pixels with high intensity can be identified as primary events and low intensity clusters can be identified as scattered radiation and be eliminated by a filter.

Quantified information such as an intensity histogram (i.e., a pulse height spectrum) can be generated 146 and a display of the object can be generated 144 with the unwanted pixels removed.

After each set of data is produced in both the stationary and scanning embodiments, the conditions for operation can be modified 138 to produce an image at a different energy level, to perform an emission or transmission study, or to rotate the source and detector assembly relative to the object under study to produce three dimensional images or two dimensional images at different angles.

The emission and transmission studies can be displayed alone or superimposed. Due to the binning capability of the system a one to one correspondence exists between both emission and transmission images that was previously not possible. This high resolution image can be color coded to distinguish between the emission and transmission images.

Figure 13:
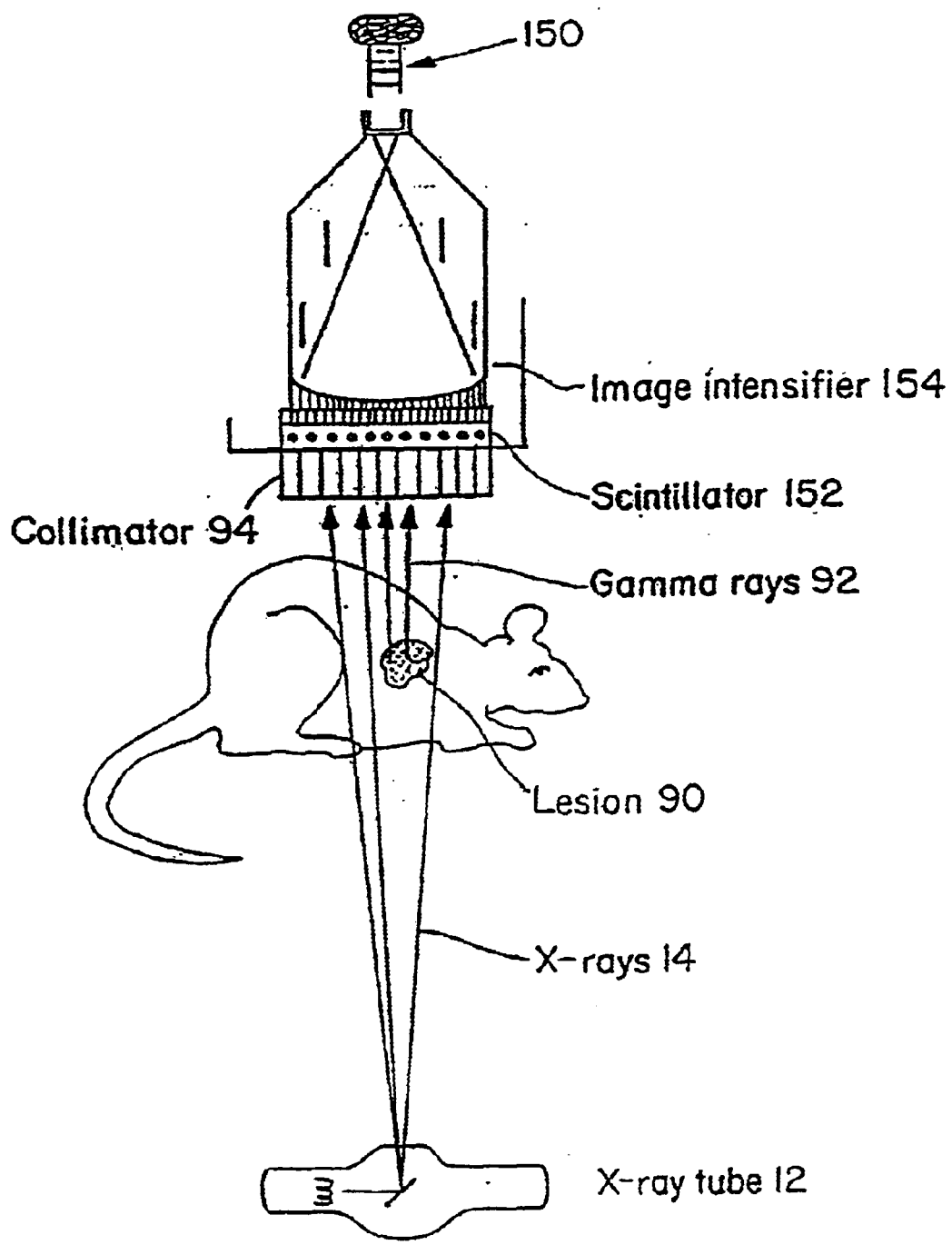
FIG. 13 is an alternate embodiment of a CCD imaging system that can be employed for both emission and transmission studies.

Another preferred embodiment is illustrated in FIG. 13 where a full frame or frame transfer cooled CCD 150 with a transparent scintillator 152 bonded on the sensitive surface of the CCD, or to an image intensifier 154, as shown. The scintillator 152 is preferably emitting anywhere from the UV blue to the red regions of the spectrum upon stimulation with x-rays or gamma-rays. The preferred scintillator is one emitting in the green such as CsI (Tl) or Cadmium tungstate, or alternatively a gadolinium based ceramic scintillator available from Hitachi Corporation. This scintillator has about twice the density of sodium iodide or CsI(Tl) and has higher efficiency. A fiber optic plate (straight or reducing) can be incorporated between the CCD and scintillator. Alternatively, an electrostatic image intensifier 154, or image diode intensifier, can be incorporated between the scintillator and the fiber optic plate. The scintillator 152 can be optically transparent plate or comprise a fiber optic array with fibers ranging in diameter from 0.006 mm to one or more millimeters. The thickness of the plate can be in the order of 0.5 mm to 5 mm.

Another preferred embodiment employs a CCD of the type described above but in conjunction with an electrostatic demagnifying image intensifier. The optical coupling of the CCD is accomplished by a fast lens at the output end of the image intensifier or by a fiber optic plate between the output screen and the CCD.

The process of obtaining a desired image includes the initiation of acquisition with the CCD for about one second or at a desired binning configuration, typically coarser than 2×2 pixels. Shorter acquisition time will be required for high count-rates and longer acquisition time is tolerated for low count rates. The optimal acquisition time for a particular application can be determined empirically by acquiring a few test frames and search for coincident events within individual pixels. Very short acquisition times (less than 1 millisecond) are easily attainable by using a fast mechanical shutter, an electro-optical shutter, or by gating the image intensifier tube. This enables acquisition with spectroscopy capability even at very high count-rates. Each acquisition "frame" will record from a few hundred to a few thousand counts. After acquisition, each frame is stored in the computer memory for subsequent processing. Depending on the application, the total number of frames for a complete acquisition can vary, for example, from ten to a few hundred.

Each gamma-ray event in a given frame stored in the computer is represented by its x and y coordinates and by an intensity value (z) which is the number of electrons generated in this area of the CCD. The z value is directly proportional to the energy of the gamma ray (or x-ray). The number of electrons generated from each interaction should be confined to one pixel or group of binned pixels forming a "superpixel". In a significant percentage of interactions, the electrons generated from a single gamma-ray interaction can be split between two or three pixels or superpixels. These split events form clusters in the image matrix which can be easily identified by the computer software and assigned an x and y coordinate.

Figure 14A:
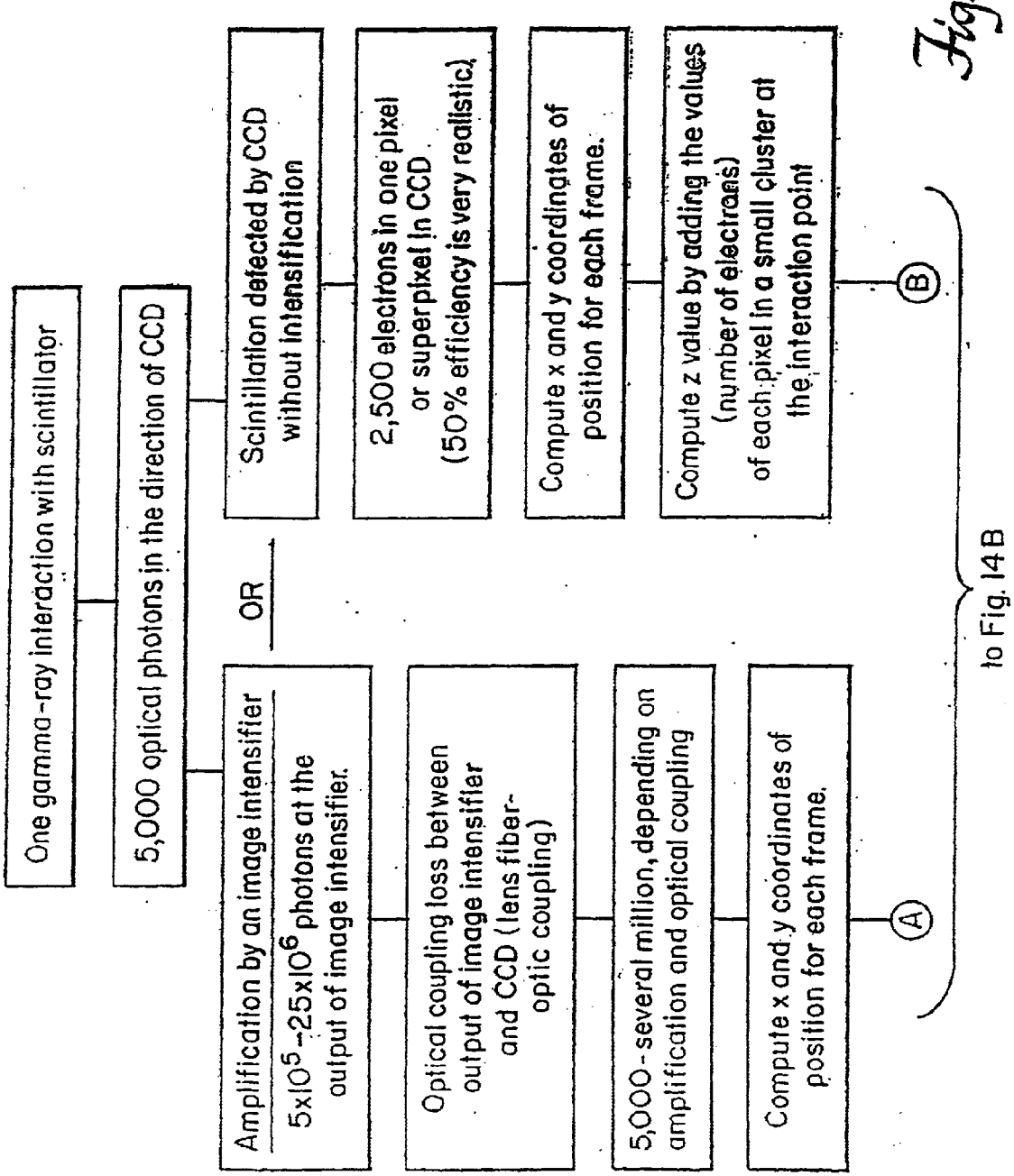
FIGS. 14A and 14B illustrate a process flow sequence for conducting emission and transmission studies of tissue.
Figure 14B:
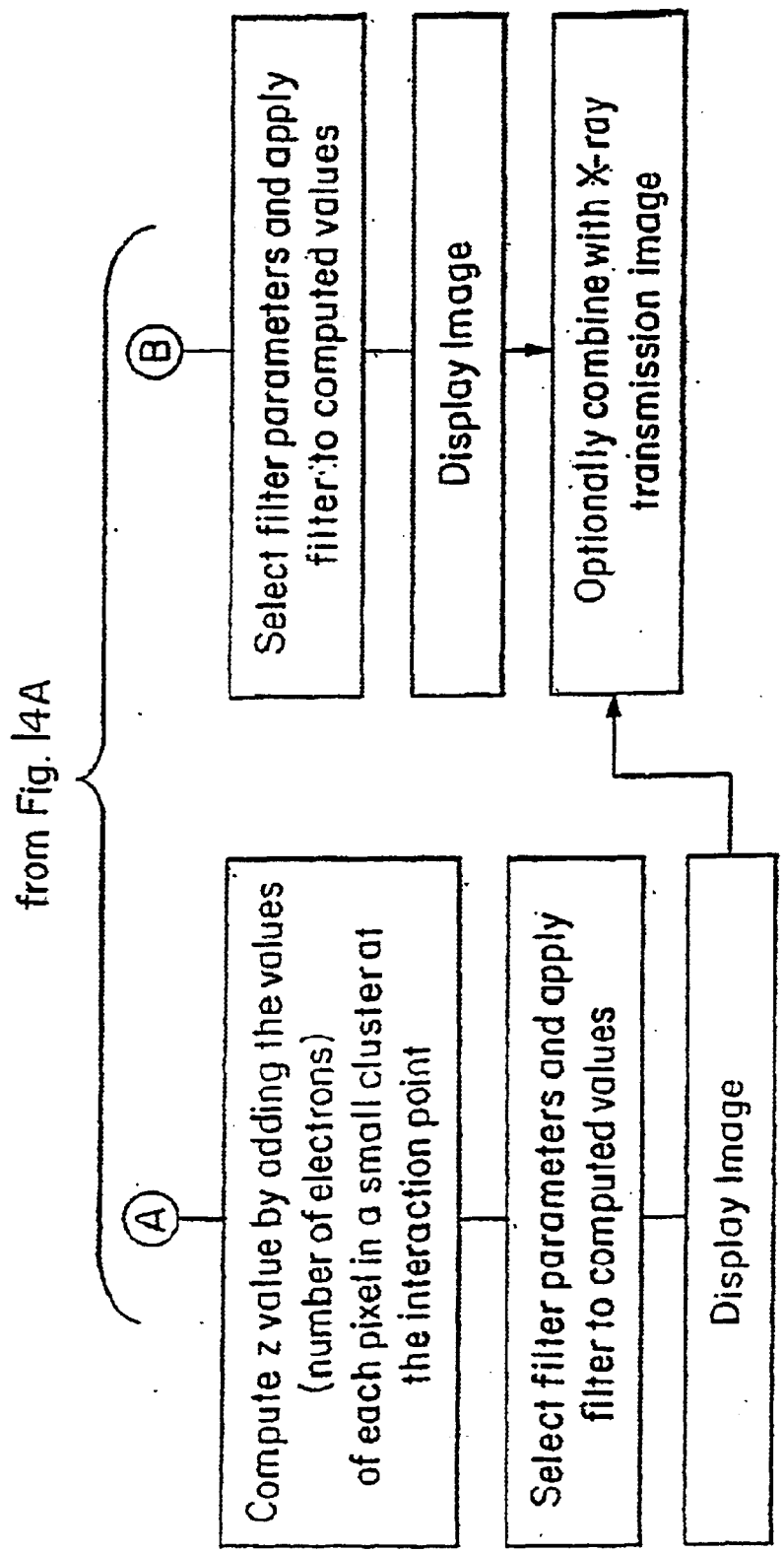

In one embodiment, as shown in the process flow sequences of FIG. 14, pulse height analysis uses the value of these neighboring pixels which are summed to produce the z value for this gamma-ray event. Low z values represent gamma-rays which have been scattered and have lost a portion of their energy. These events are generally not desirable for inclusion in an image because they carry false position information. Therefore, the degree of rejection of each event can be decided by software on the basis of the z value and a spectrum of the number of gamma-rays versus the z value (energy) can be recorded. This filtering process can be repeated for each frame and all the frames can be added together to form the final image. The operator can optionally go back to each original frame, use a different z value threshold and reconstruct the final image using different filter parameters. Variations in the sensitivity of each pixel or superpixel can be mapped and included in the counter for pixel by pixel corrections. The ability to discriminate different radiation sources measured simultaneously or sequentially includes defining filter parameters as selected energy threshold values or ranges.

In this radionuclide imaging technique, the degree of scatter rejection can be varied after the image acquisition in order to decide on the optimal scatter rejection. This is not possible with the conventional radionuclide imaging technology employing a gamma camera or a rectilinear scanner. A gamma camera or rectilinear scanner is generally incapable of detecting and processing high intensity x-rays which are employed for high quality x-ray radiography.

If an image intensifier is not used, the scintillator can be in direct contact with the CCD. Alternatively, a fiber optic reducer can be used between the CCD and the scintillator. Typical reduction ratios vary from 1:1 to 6:1 although the present embodiment is not limited to these ratios. Therefore, for a 20 mm×20 mm CCD, and a 6:1 fiber optic reducer, the area of coverage will be about 120 mm. With a gated image intensifier or a shutter, the CCD does not receive any signal during the readout process. In a direct contact configuration, the use of frame transfer CCD as shown in FIG. 10 is preferred.

In applications utilizing x-ray transmission measurements a single frame is acquired for the recording of the x-rays emerging from the irradiated body of tissue. The CCD is operating in the integrating mode and each pixel or superpixel which accumulates a charge which is proportional to the total number of x-rays in this region without any energy discrimination. The resulting radiographic image can be combined electronically with the radionuclide image to form an accurate representation of both physiologic and anatomic information.

In the case of thin specimens examined in vitro a light source with wavelength ranging from the ultraviolet to near or mid infrared can be used for the transmission image in the integrating mode. In this approach, the light shield in front of the scintillator is removed and the detector is placed in an enclosure to shield it from ambient light.

The present invention can thus combine radionuclide emission imaging and x-ray transmission imaging (radiography) using the same area detector with spectroscopic capability in the gamma-ray imaging mode. This camera can be operated utilizing both, the counting pulse-height analysis for gamma-ray imaging, and in the integrating or counting modes for x-ray substantially transmission imaging. This enables exact superposition of the two images for accurate anatomic and physiologic imaging. Also, the operator can change the energy threshold even after the radionuclide image has been acquired. Thus, higher intrinsic spatial and energy resolution are provided than found in the conventional approaches.

Figure 15:
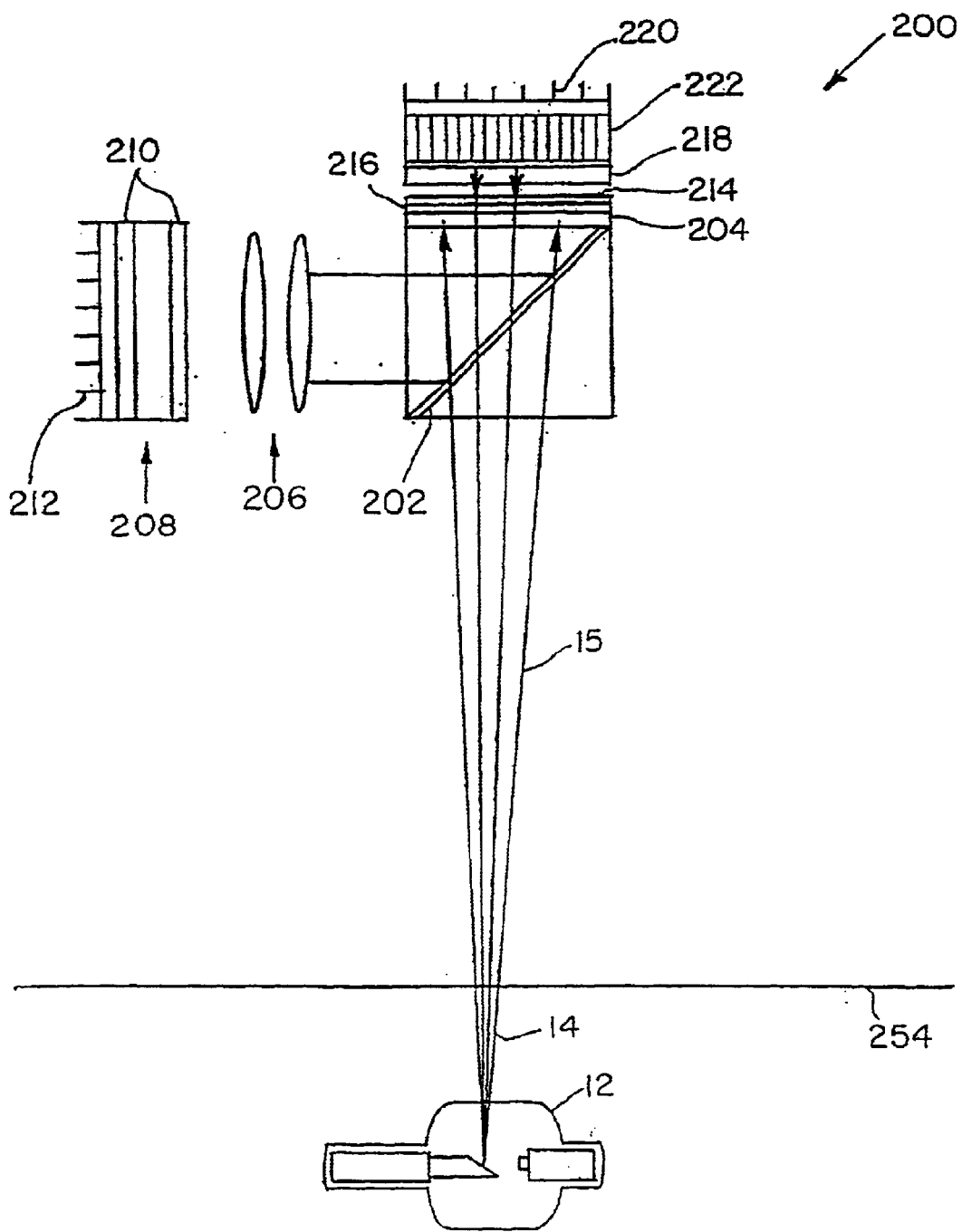
FIG. 15 is a schematic diagram of an alternative preferred embodiment to the bone densitometry measuring apparatus of FIG. 2 using dual scintillation screens and dual detectors.

FIG. 15 is a schematic illustration of one preferred embodiment of a dual-energy bone densitometry system 200 in accordance with the invention. An x-ray tube 12 emits x-rays 14 which pass through the x-ray transparent patient table 254 and into the patient (not shown). The x-rays 15 which pass through the patient are directed through an x-ray transparent mirror 202 and strike a first scintillator screen 204. The scintillator 204 reacts to low-energy x-rays and generates a light pattern corresponding to the low energy x-ray pattern. The light generated by the scintillator 204 propagates back to the mirror 202 which reflects the light to the lenses 206. The lenses 206 couple the image from the scintillator 204 to an image intensifier 208 having microchannel plates 210. Alternatively, the image intensifier 208 can be a proximity-type intensifier without the microchannel plates 210. The light from the image intensifier 208 is received and detected by the detector 212, which can be a CCD array, a CID array or an amorphous silicon or CMOS sensor. The detector 212 senses the image which corresponds to the low-energy x-rays and generates an electronic representation of the image in the form of pixel data.

High-energy x-rays pass through the scintillator 204 to an optional x-ray filter 214. The filter 214 is preferably a copper filter which blocks any remaining low-energy x-rays which pass through the scintillator 204. An optional light block filter 216 can also be included between the scintillator 204 and the x-ray filter 214 to block any stray optical radiation emanating from the scintillator 204 from reaching a second detector 220.

The high-energy x-rays from the filter 214 strike a second scintillator 218 which is reactive to the high-energy x-rays to generate an optical image which corresponds to the pattern of high-energy x-rays. The optical image is received by a second detector 220, which can also be a CCD or CID array or an amorphous silicon image sensor. The second detector 220 senses the optical image and generates an electronic representation of the high-energy x-ray pattern. An optional x-ray absorbing fiber optic plate 222 can also be included between the scintillator 218 and the detector 220 to absorb any remaining x-rays and thus prevent them from interfering with the detector 220.

The system 200 of FIG. 15 can be used in either a scanning mode or a stationary mode. In the scanning mode, the x-ray tube source 12 as well as the detection system are moved continuously or in a stepping motion along the region being examined. While the system scans the region, a series of images are obtained having short exposure acquisition times. In the stationary mode, a single exposure is made of the entire region being examined. Time delay integration (TDI) is used in which the CCD stores the total charge for each pixel during a selected x-ray exposure interval. At the end of the x-ray exposure, the discrete representation in each pixel is readout by a CCD controller. Once the data is thus obtained, the comparative processing techniques of dual photon absorptiometry can be used to determine quantitative density measurements of the calcified material such as bone within the body regions exposed by the x-rays.

In the system 200 of FIG. 15, the image intensifier 208 can be omitted. In that configuration, to ensure that image data for the low-energy x-rays can be accurately collected, the detector 212 can be cooled to increase signal-to-noise ratio.

Figure 16:
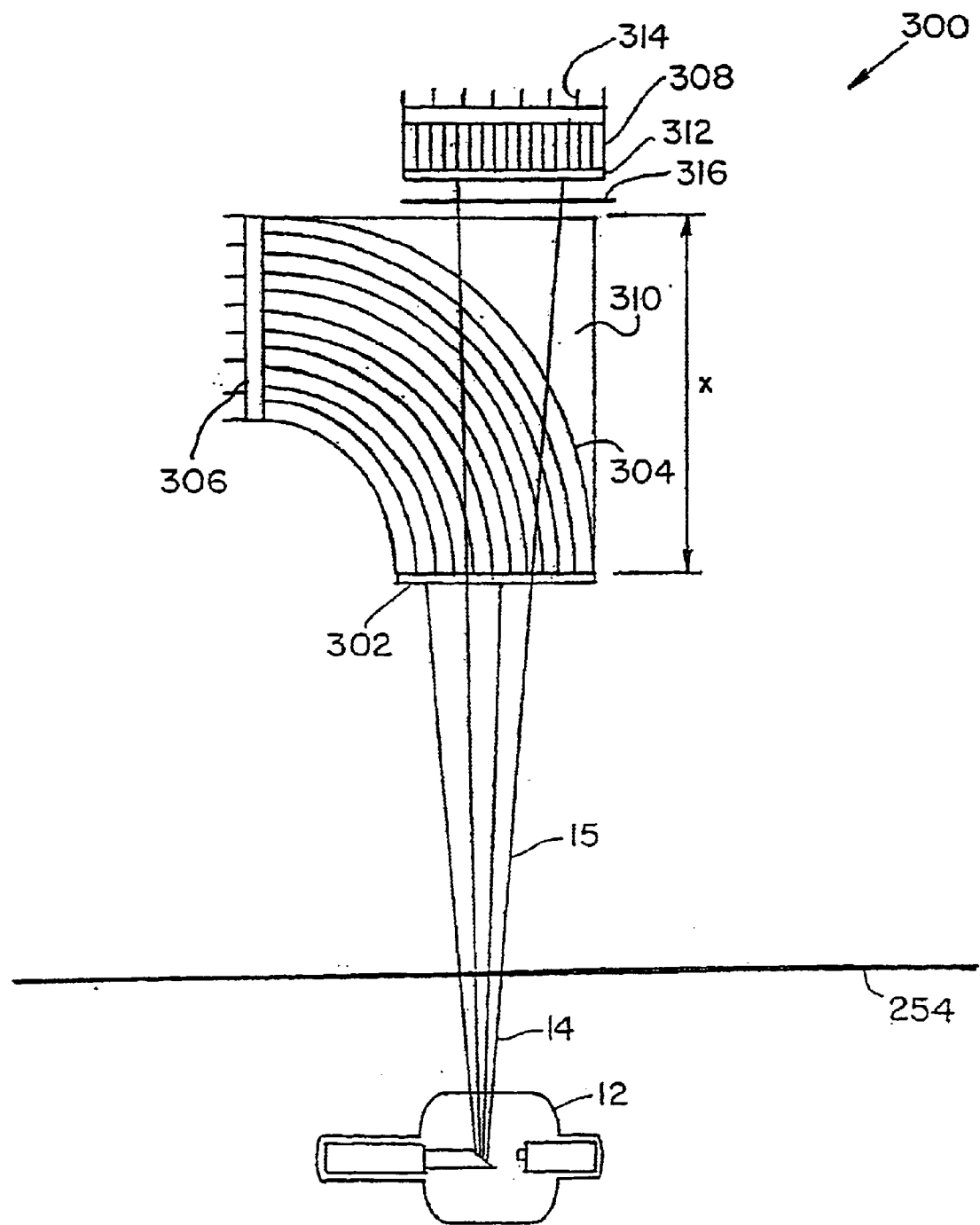
FIG. 16 is a schematic diagram of an alternative preferred embodiment to the bone densitometry measuring apparatus of FIG. 15.

FIG. 16 is a schematic diagram of another embodiment of a dual-energy bone densitometry measuring system 300 in accordance with the invention. An x-ray tube 12 outputs x-rays 14 through x-ray transparent patient table 254 and into the patient. X-rays 15 directed through the patient strike a first scintillator 302 which is reactive to low-energy x-rays to generate an optical image of the low-energy x-ray pattern out of the patient. The optical image is carried by a coherent fiber optic conduit 304 to a CCD detector 306 which detects the optical image and generates the electronic representation of the low-energy x-ray pattern. The fiber optic conduit 304 is preferably made of plastic optical fibers to facilitate collection of the low-energy image. However, if the distance labeled "x" is selected to be small enough, glass fibers can be used instead. The space labeled 310 is filled with a film material being the same material as that of which the fibers are made.

The high-energy x-rays pass through the scintillator 302, the fiber optic conduit 304 and the film material 310 and strike a second x-ray phosphor scintillator 312. The second scintillator 312 is reactive to high-energy x-rays and therefore generates an optical image which corresponds to the high-energy x-ray pattern. The optical image generated by the scintillator 312 is detected by a second CCD array 314 which generates the electronic representation of the high-energy x-ray pattern. An optional copper or aluminum filter 316 can be inserted in front of the second scintillator 312 to absorb any remaining low-energy x-rays. Also, an x-ray absorbing fiber optic plate 308 can be inserted between the scintillator 312 and the CCD 314 to prevent x-rays from impinging on the CCD 314.

Figure 17:
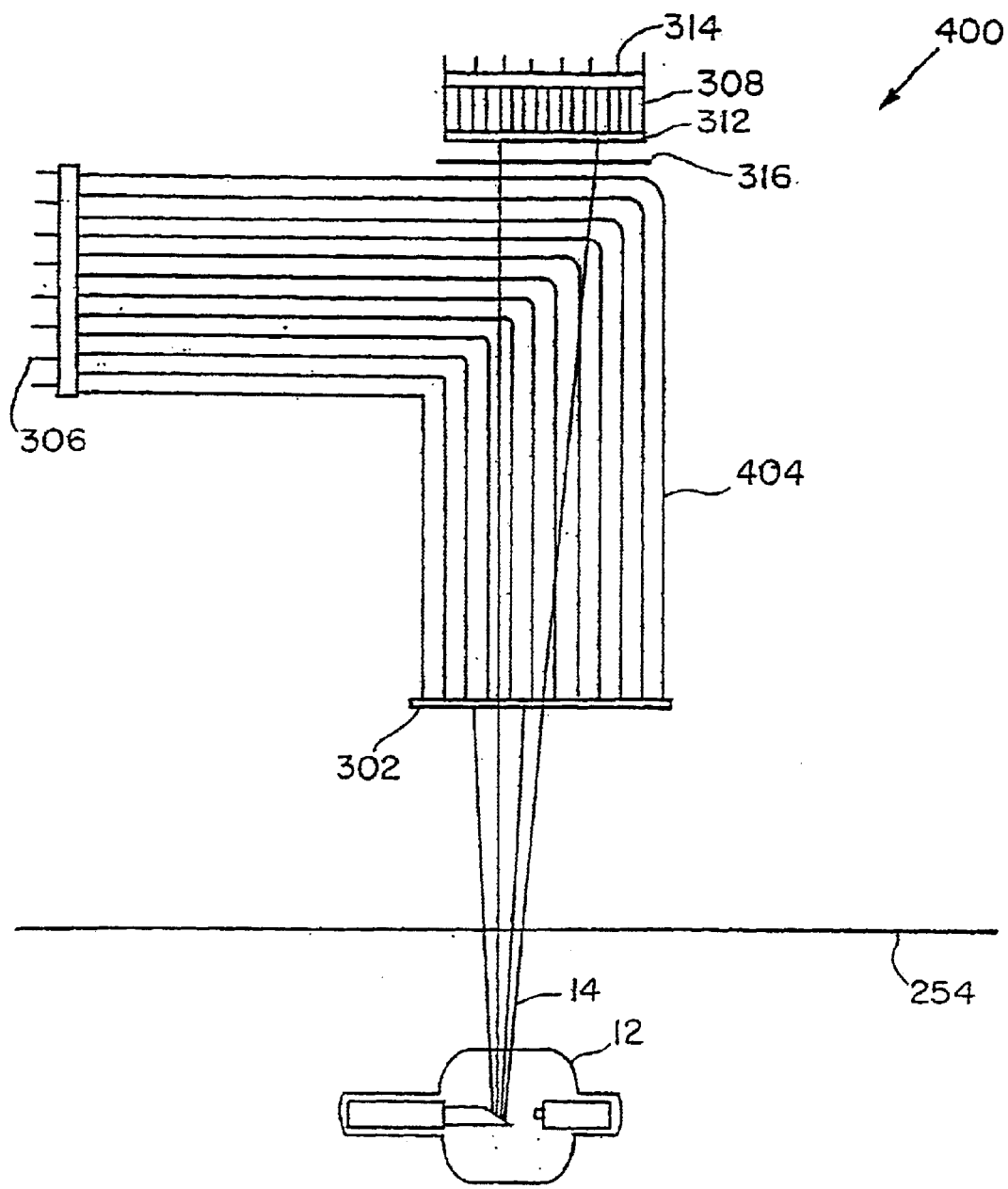
FIG. 17 is a schematic diagram of a variation of the bone densitometry measuring apparatus of FIG. 16.

FIG. 17 is a schematic diagram of another embodiment of a dual-energy bone densitometer measuring apparatus 400 in accordance with the invention. The system 400 of FIG. 17 is the same as the system 300 of FIG. 16 except that the coherent fiber optic conduit 304 in FIG. 16 is replaced with a different conduit 404 in the system 400 of FIG. 17. In the conduit 404 of FIG. 17, the fibers are bent at approximate right angles with moderate to small radii of curvature. As in the embodiment of FIG. 16, the fibers are either plastic or glass. Because of the different fiber bending in which the collected radiation is redirected from a first optical path onto a second optical path, the need for the bulk material 310 shown in FIG. 16 is eliminated.

Figure 18:
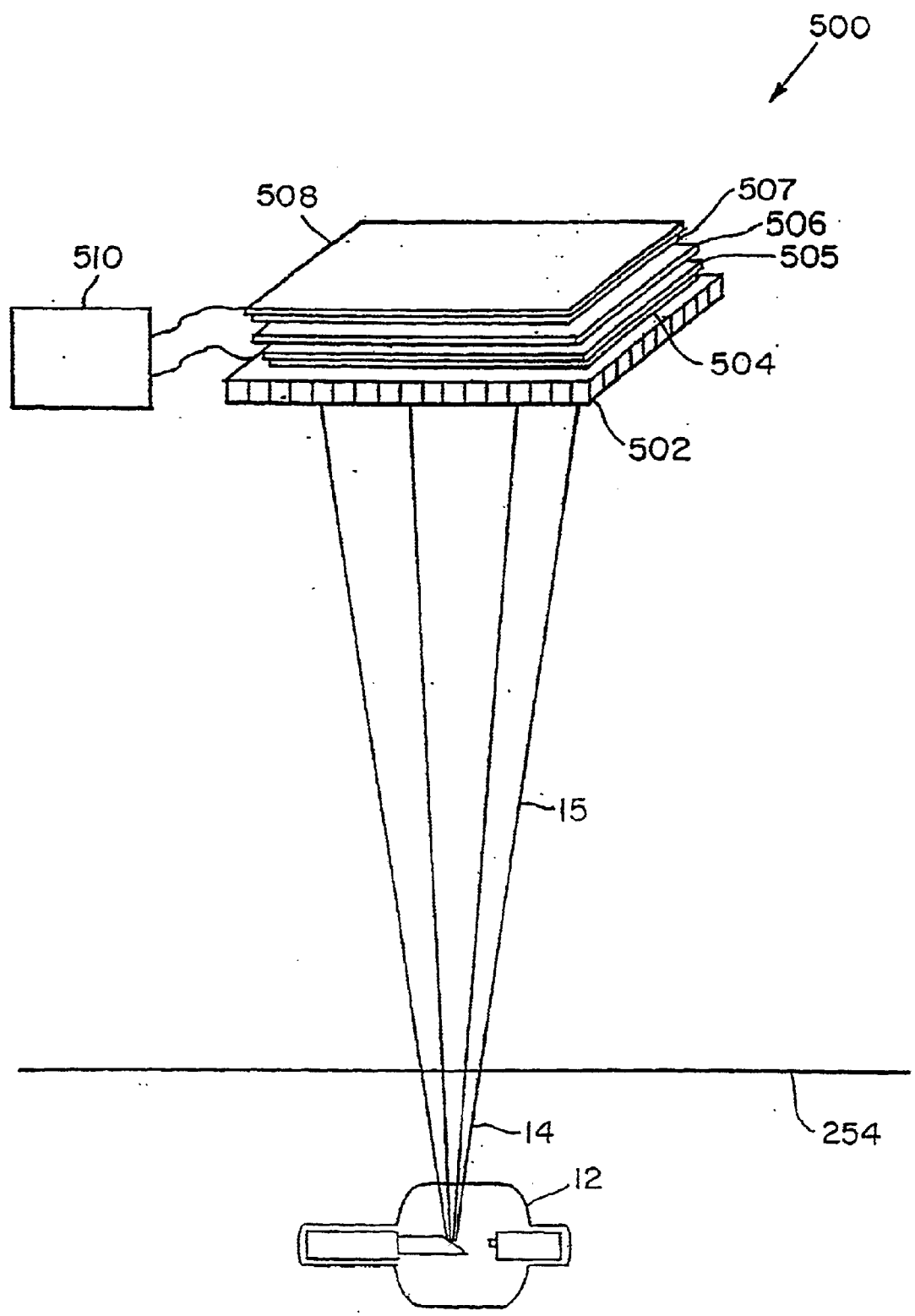
FIG. 18 is a schematic diagram of another alternative preferred embodiment to the bone densitometry measuring apparatus of FIG. 15 having dual amorphous silicon image sensors.

FIG. 18 is a schematic diagram of another embodiment of a bone densitometer measuring apparatus 500 in accordance with the invention. In this embodiment, scintillator plates 505 and 507 are used to convert the x-ray energy into optical energy. Once again, the x-ray tube 12 directs x-rays 14 through the patient table 254 and the patient. The x-rays 15 emanating from the patient first strike an anti-scatter grid 502 which prevents scattered x-rays from reaching the detectors. The x-rays then strike a first amorphous silicon image sensor 504 which detects low-energy x-rays and generates the data which indicates the low-energy x-ray pattern. The low energy sensor 504 can be thinner than the high-energy sensor 508 to reduce the filtering requirements of the system. Also scintillator 505 can be thinner than scintillator 507 to improve collection efficiency of the system. High-energy x-rays pass through the first sensor 504 and then through a copper, tungsten, gadolinium or aluminum x-ray filter 506 which filters out low-energy x-rays. The glass substrate can also act as a low energy filter. The high-energy x-rays then strike the second amorphous silicon image sensor 508 which generates the data for the high-energy x-ray pattern. The low-energy x-ray pattern data and the high-energy x-ray pattern data are read out of the amorphous silicon image sensors 504 and 508, respectively, by a detector controller 510.

Figure 19:
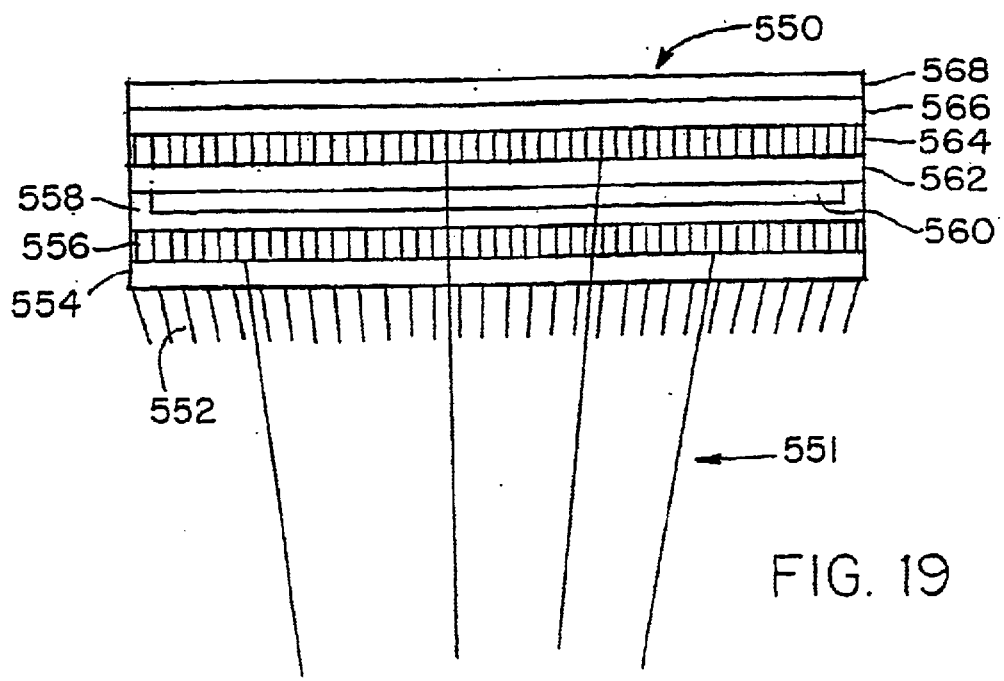
FIG. 19 is a schematic diagram of an alternative detection structure including dual amorphous silicon image sensors which can be used with the various embodiments of the bone densitometry measuring apparatus of the invention.
Figure 20A:
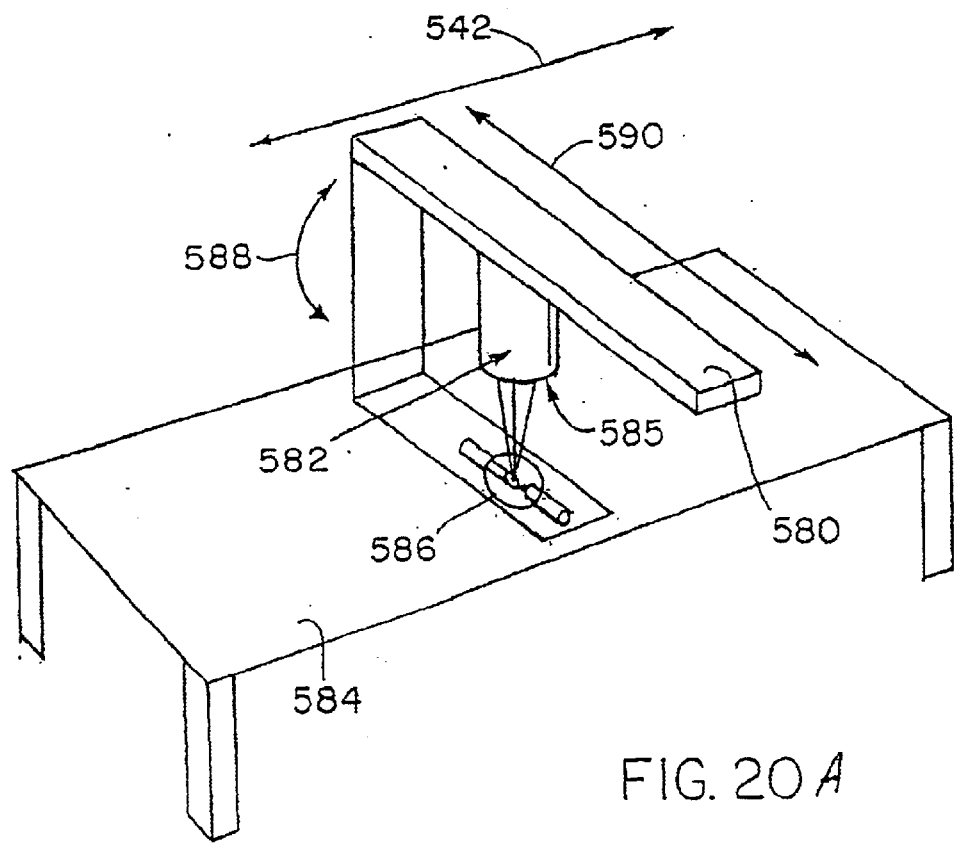
FIG. 20A is another preferred embodiment of a bone densitometer for static, scanning or stepped imaging procedures.

FIG. 19 is a schematic diagram of an alternative detection structure 550 which can be used with the dual-energy bone densitometry measuring apparatus 500 of FIG. 18. The lower layer of the structure 550 is an anti-scatter grid 552 used to prevent scattered x-rays from reaching the detection structure 550. The next layer is a low-energy x-ray scintillator layer 554 which generates an optical image of the low-energy x-ray pattern. An amorphous silicon image sensor 556 detects the optical image from the scintillator 554 to generate the data for the low-energy x-ray pattern. A substrate layer 558 is formed over the amorphous silicon image sensor layer 556. The substrate layer 558 includes a thinned central region 560. If needed, the thinned substrate 558 provides for increased transmission to the second scintillator layer 562. The second scintillator 562 is reactive to high-energy x-rays to generate an optical image of high-energy x-ray pattern. The optical image is detected by a second amorphous silicon image sensor 564. The structure 550 is covered by a protective substrate 566, preferably made of glass. A thin layer of lead can be formed on top of the glass to prevent propagation of x-rays beyond the structure 550. Preferred scintillators include Cs(+1), CdWO4, Cesium iodide (thallium or sodium doped) or gadolinium oxysulfide. The amorphous silicon array sensors and the associated control and processing systems can utilize the binning and other processing capabilities described elsewhere in the present application. Additionally, a plurality of such sensors can be combined to form a single or dual array. The array can be linear, rectangular or square depending upon the particular application. The systems can be used in conjunction with a C-arm assembly where the C-arm 580 rigidly aligns the source 586 and detector assembly 582 as shown in FIG. 20A. The C-arm 580 can also be used to rotate the source and detector about the patient on table 584 as indicated at 588 to provide multidirectional viewing of the entire human skeletal structure including the hip and femur. Thus lateral spine imaging and quantitative analysis can be conducted using the present system. The detector assembly 582 includes a CCD sensor as described herein in conjunction with a straight, angled or bent fiber optic coupler and scintillator. The detector assembly 582 can be scanned or stepped along axis 590 and axis 592 that is parallel to the spine of the patient in order to provide a sequence of images for both quantitative and qualitative analysis.

Figure 20B:
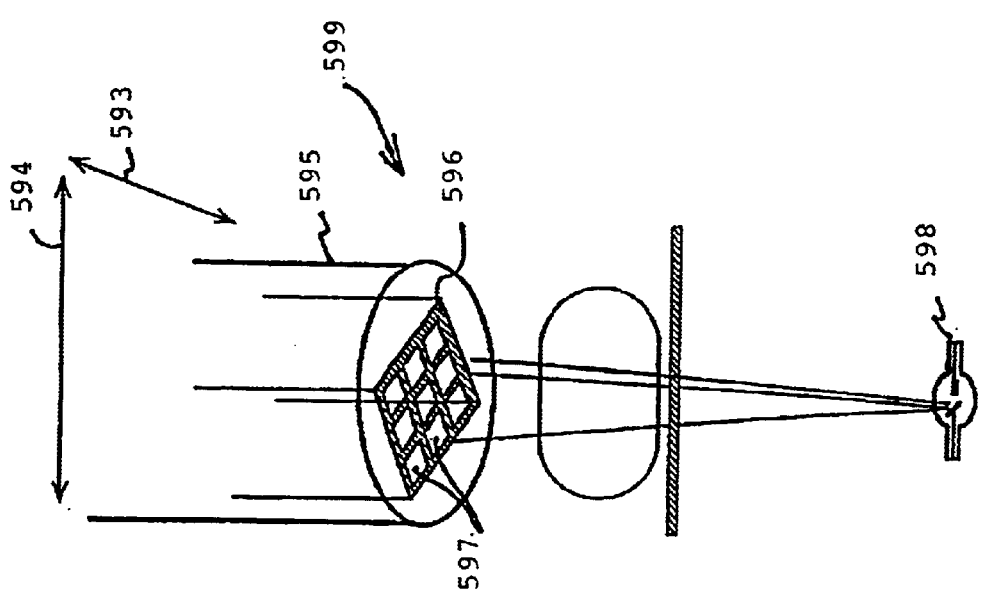
FIG. 20B illustrates a preferred embodiment of an x-ray imaging system using an x-ray detector array.

A preferred embodiment of the detector system 582 is illustrated in FIG. 20B. In this system 599, the detector 596 is secured within a shielded housing 595 and includes a rectangular or square array 597 of pixelated detectors. In this particular embodiment, a 3×3 array of cadmium zinc talluride (CdZnTe) detectors. Detectors based on cadmium telluride compounds detect x-rays directly without the need for a scintillator. This type of detector is available from DG Rad Corporation, San Diego, Calif., or from eV Products, Saxonburg, Pa., or from Amptek in Bedford, Mass. This type of detector receives x-rays after transmission through the patient and generates electron/hole pairs depending upon the energy of the incident x-rays. The detector 596 can be moved in either direction 593, 594 to collect during scanning or to be positioned between snapshots.

Figure 20C:
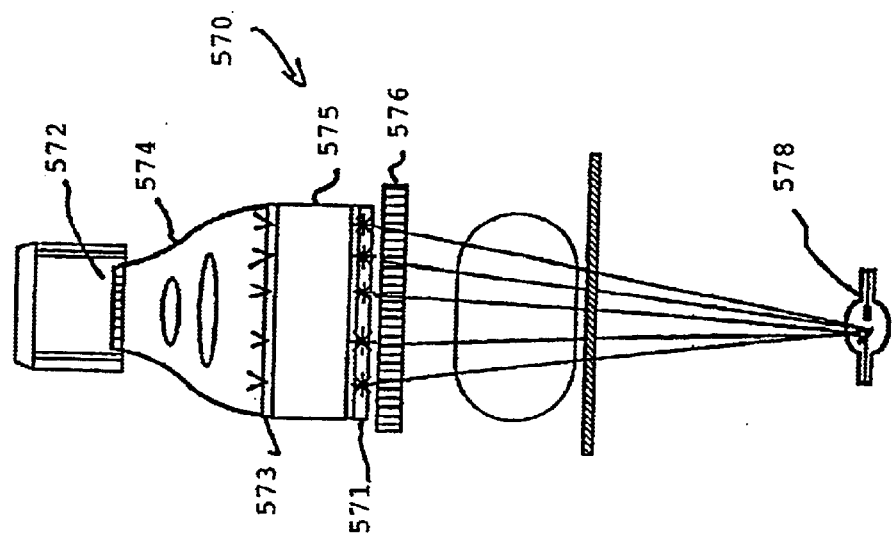
FIG. 20C illustrates a preferred embodiment utilizing a proximity type image intensifier.

Illustrated in FIG. 20C is an alternative embodiment 570, in which an x-ray source 578 generates x-rays that are transmitted through the patient onto an optional focused or non-focused antiscatter grid 576. The x-rays are received by a phosphor 571 which emits light that is accelerated through the gap of a proximity focused image intensifier 575 with a photocathode. A second phosphor 573 receives the intensified image and couples the light to an optical system 574 that reduces the image by a lens of a fiberoptic system onto a detector array 572.

Figure 21A:
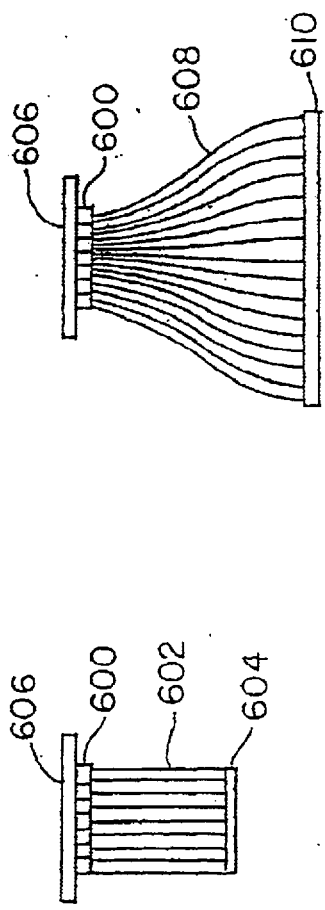
FIGS. 21A–21C illustrate alternate embodiments for the detector assembly of FIG. 20.
Figure 21B:
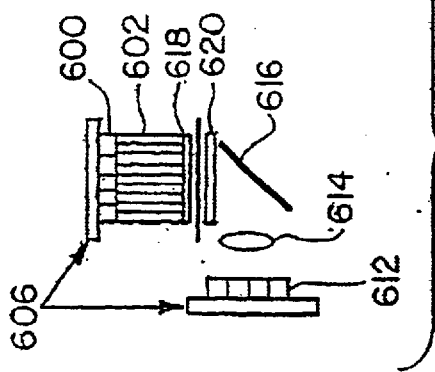
Figure 21C:
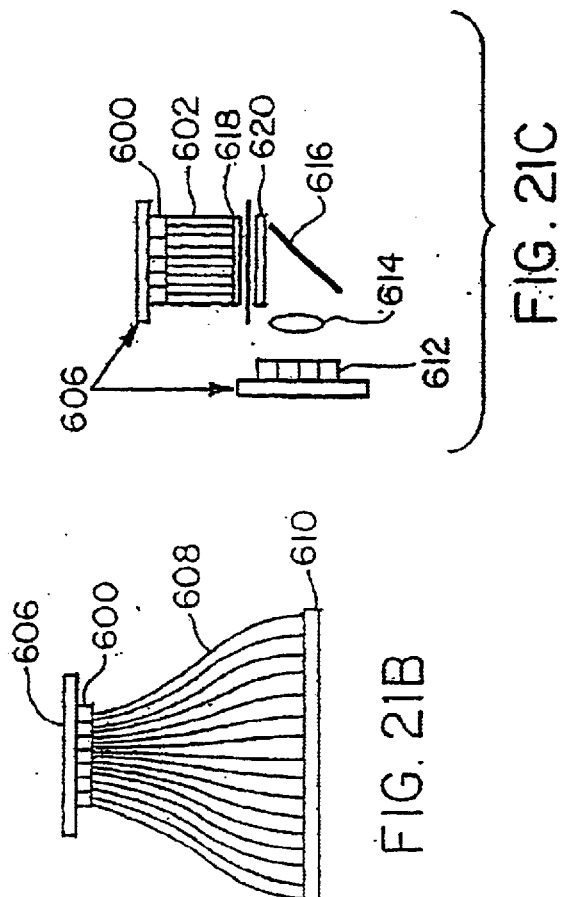

The detector assembly 582 can include various configurations described elsewhere herein, including the examples illustrated in FIG. 21A, 21B, and 21C. In FIG. 21A a straight fiber optic coupler 602 optically couples the scintillator 604 to the CCD (or CID or amorphous silicon or CMOS) sensor array 600. Amorphous selenium or other photodetectors such as zinc cadmium sulfide can be used. They do not require a scintillator. These photoconductors use thin film transistor pixelated readout. An optional cooler(s) 606 can be used in these examples. In FIG. 21B a fiber optic reducer 608 couples the scintillator 610 to the sensor array 600. A proximity type x-ray image intensifier and scintillator can replace scintillators 604 and 610. In FIG. 21C a dual sensor system includes sensors 600 and 612, fiber optic coupler 602, scintillators 618, 620, mirror 616, and lens 614. This system functions in a manner similar to that described in connection with FIG. 15.

Figure 22B:
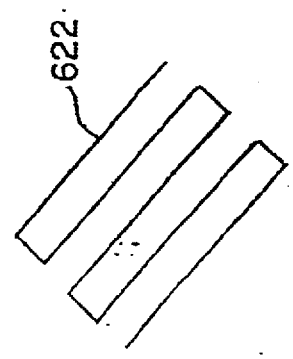
FIGS. 22A–22B illustrate scanning or stepped imaging procedures.
Figure 22A:
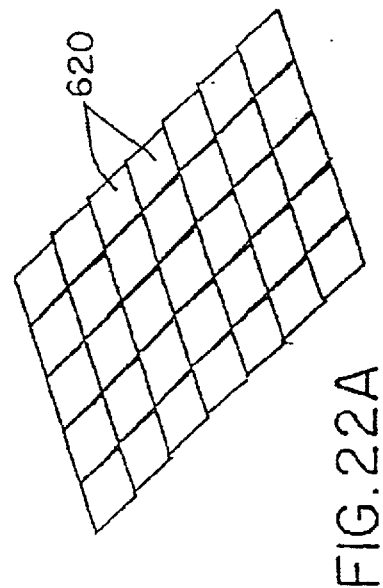

FIGS. 22A and 22B illustrate a preferred method of imaging in which the entire imaging field is composed of a series of slightly overlapping individual images 620 that are acquired by a continuous scan or stepped imaging sequence along the rectilinear path 622. Dual energy tissue or bone density measurements can be accomplished by collecting data at two energies at each subfield 620. The x-ray source can be switched or filtered as described previously to generate discrete energy peaks.

Figure 23:
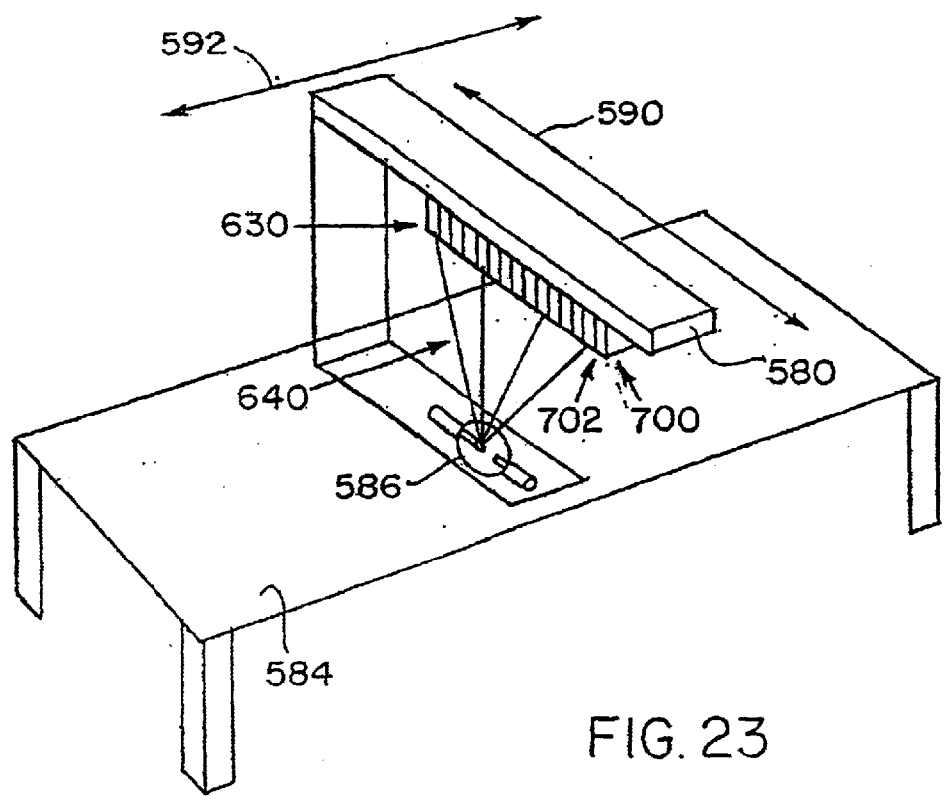
FIG. 23 is another preferred embodiment of an imaging system in accordance with the invention.

FIG. 23 illustrates a fan-beam system in which the x-ray source 586 generates a fan shaped beam 640 that is detected by a detector system 700. System 700 can include a scintillator, fiber optic plate or reducer for each of a plurality of sensors 630 which are aligned in a linear array to collect fan beam 640. Detector system 700 can use a lead slit collimator 702 and can use CCDs, CIDs or a number of amorphous silicon sensors in configurations illustrated, for example, in FIGS. 21A–21C.

Figure 24:
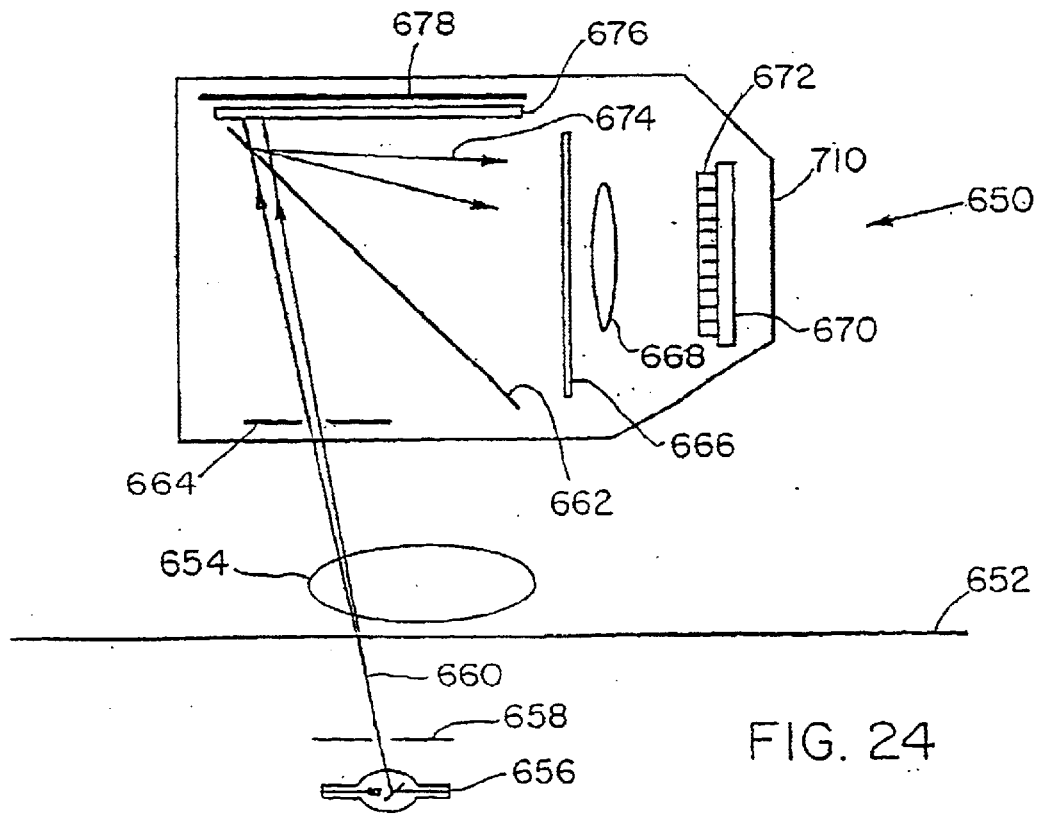
FIG. 24 is another preferred embodiment of an x-ray imaging system in accordance with the invention.

FIG. 24 illustrates another preferred embodiment 650 in which a patient 654 is positioned on table 652. X-ray tube 656 directs fan-beam 660 through a scanning slit collimator 658, the patient 654 and a second scanning slit collimator 664. The radiation 660 then passes through mirror 62 striking the scintillator 676. The scintillator emits light that is reflected by mirror 662 towards the sensor 672 as illustrated at 674. Optional lead glass element 666 can be placed at any position between the mirror 662 and the sensor 672. A lens 668 and cooler 670 can also be employed, if necessary. Lead foil 678 can be used to line the enclosure 710 to reduce interactions between the scattered x-rays and the sensor 672. The system can alternatively use a proximity type image intensifiers in the x-ray path before the mirror.

Figure 25A:
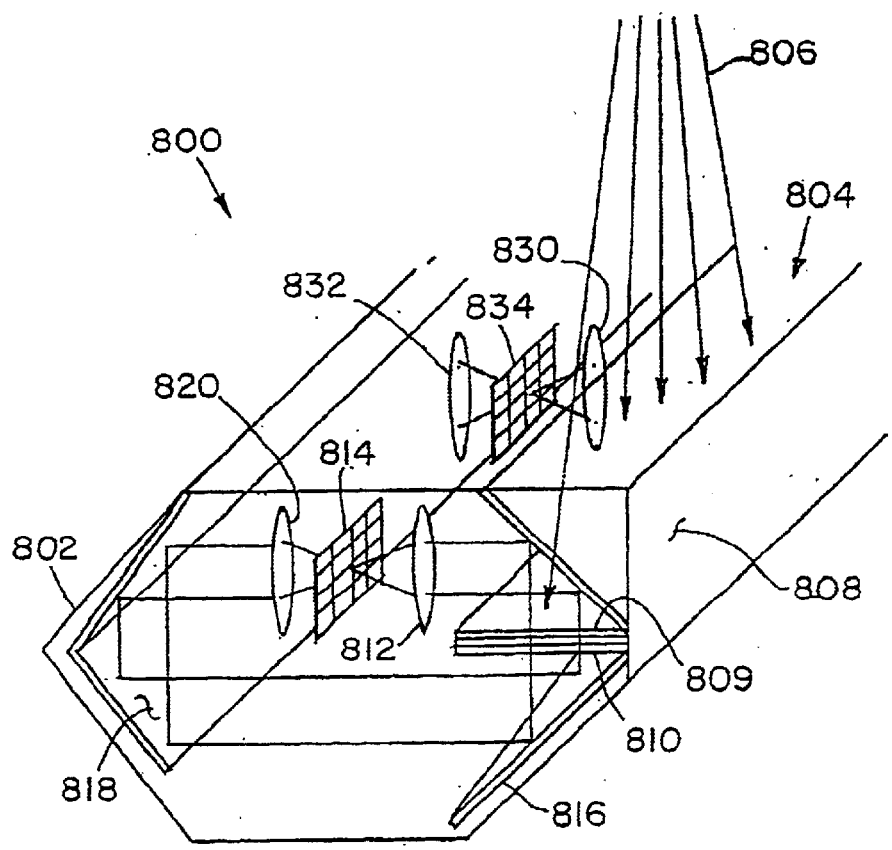
FIG. 25A is a schematic diagram of a detection structure used for bone densitometry measurements and tissue lesion imaging in accordance with the present invention.
Figure 26:
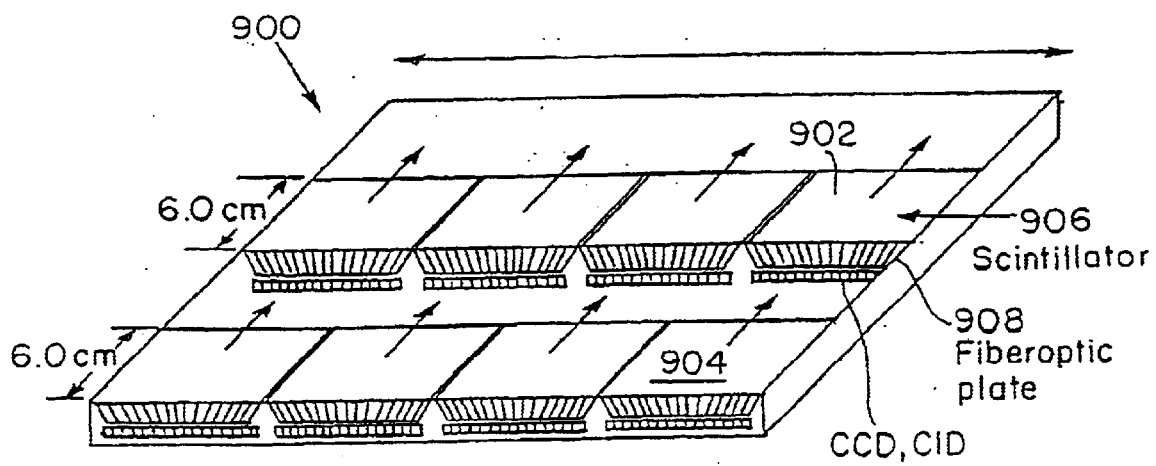
FIG. 26 is a preferred embodiment of the invention in which a dual spaced array is used for digital mammographic imaging and quantitative analysis.

FIG. 25A is a schematic diagram of a detection system 800 which can be used with the systems described above for dual-energy bone densitometry measurements as well as tissue and lesion imaging. The system 800 can include an enclosure 802 having an aperture 804 through which radiation such as x-ray beams 806 enter the system 800. In one embodiment, the x-ray beams 806 pass through an x-ray transparent mirror 808 and strike a first scin-tillating plate 809. The first scintillator 809 is reactive to low-energy x-rays and produces an optical image corresponding to the low-energy x-ray pattern. The optical image is projected back onto the mirror 808 which reflects the image to lens 812. The lens 812 focuses the light onto a first surface of a CCD array detector 814. The detector 814 can include a proximity-type image intensifier to enhance image detection capabilities. An annular cooler (not shown) can also be placed around the CCD detector 814 to cool the CCD and therefore improve signal-to-noise ratio.

High-energy x-rays pass through the top scintillator 809 and strike the lower second scintillator 810 which is reactive to the high-energy x-rays to produce an optical image which corresponds to the high-energy x-ray pattern. The optical image is reflected by a second mirror 816 to a third mirror 818 which directs the light through a second focusing lens 820. The lens 820 focuses the light onto the back surface of the CCD detector 814. The back surface can also include a proximity-type image intensifier. In addition, the annular cooler, if present, cools the front and back surfaces of the CCD detector 814.

Thus, the system 800 of FIG. 25A produces increased sensitivity by sensing on opposite sides of a single thinned CCD detector 814. Spatial correlation between the two images which are fused to form a single image is greatly improved over the previously described embodiments with separate detection surfaces since the relative locations of the image detection surfaces can be more precisely controlled. High and low energies can be detected on both sides.

The detection system 800 of FIG. 25A can include plural two-sided CCD detectors to provide the system with a wide field-of-view along with combined electronics and cooling. FIG. 25A illustrates a second detector 834 and associated lenses 830 and 832. It will be understood that more detectors and lenses can be added as needed.

The dual-energy configuration of the system 800 described above facilitates bone densitometry measurements as previously described. However, the system 800 can also be used for detecting and imaging lesions in patient tissue as described above. In that embodiment, the x-ray beams 806 are replaced with other types of radiation such as in the visible or infrared ranges. The scintillators 809 and 810 and the mirrors 808, 816 and 818 can be used to form images of the tissue to be formed at two different wavelengths on opposite surfaces of the detectors 814 and 834.

That panel detectors are being developed for digital x-ray imaging, primarily chest imaging and mammography. These area detectors are made of amorphous silicon which is deposited on a glass substrate. The thickness of the amorphous silicon and other materials on the plate is a few microns at the most and the glass substrate has a thickness typically about 2 millimeters. Amorphous selenium area detectors can also be employed for x-ray imaging applications. With pixelated detectors, images can be acquired in full pixel resolution or in the pixel binning mode which produces lower spatial resolution but higher signal to noise ratio. The pixel binning acqui-sition can be symetric (2×2 pixels) or asymetic (1×2 pixels).

Amorphous silicon area detectors on glass substrates use a scintillator. The scintillator is typically a gadolinium oxysulfide based phosphor which is in common use for x-ray imaging with film. The use of vapor deposited Thallium-activated Cesium iodide has also been used. Cesium iodide can be grown in a needle-like structure which results in a reduction of the lateral diffusion of the scintillation light. However, even with Cesium iodide, diffusion of the scintillations occurs and loss of spatial resolution and contrast are inevitable in most practical x-ray imaging applications. This problem is compounded by the fact that most x-rays interact near the entrance to the scintillator due to exponential attenuation and therefore the induced scintillation light must travel as long as 400 microns in order to be detected by the light sensing elements of the area detector. This is a well known problem in radiological imaging which is of concern with both digital and film-based imaging tasks.

A preferred embodiment of the invention uses an area or linear detector array, such as amorphous silicon, or amorphous selenium, in an irradiation geometry which maximizes the spatial resolution. The system 840 illustrated in FIG. 25B directs the x-rays 842 first through the substrate 894 of the detector 846 with minimal absorption or shadowing. This may be very problematic with detectors which do not present a backing package and substrate which is substantially transparent to x-rays. Some detectors however, can be modified to be transparent to x-rays which enables their use in the reverse illumination geometry. Amorphous silicon plates are typically manufactured on a glass substrate of approximately 2 mm thickness. The silicon sensor itself and the associated structures on the plate do not exhibit significant x-ray absorption because they are extremely thin. However, the thickness of 2 mm of glass can absorb a significant amount of x-rays, and for this reason it will have to be designed specifically depending on the parti-cular x-ray imaging application. At an x-ray energy of 50 kiloelectron volts for example, the glass substrate may transmit about more than 80% of the incident x-rays. The actual transmission will depend on the type of glass and the actual thickness. If a thinner glass substrate is designed, 1 millimeter of thickness for example, it any transmit about 90% of the incident x-rays. By further reduction of the substrate thickness to 0.5 millimeters the x-ray transmission may exceed 95%.

Therefore, by using a thinned substrate, amorphous silicon sensors can be adapted to a back-illumination geometry which results in better spatial resolution. In cases where the incident photon energy is higher than 50 kiloelectron volts, the commonly used substrate thickness may be used. This can be particularly true in high energy imaging such as teletherapy imaging or some industrial x-ray imaging tasks. Ideally, a very thin substrate is desirable for allowing nearly 100% of the incident x-rays to interact with the scintillator 848 which provides the useful signal. An important embodiment of this invention is the use of a reverse illumination geometry with amorphous silicon-scintillator detectors. A further embodiment is to use a thinner substrate for further optimization of the detection efficiency. Although some theoretical absorption will occur in the substrate, it can be sufficiently transparent for many x-ray imaging applications.

The mammographic application presents a significant challenge because of the low energy and weak penetrating power of x-rays in the mammographic energy spectrum, but even in this case the glass substrate thickness can be reduced to a thickness of a few microns if necessary. Mechanical stability of the plate can be achieved by a layer of a material with low atomic number and density such as beryllium or a carbon fiber composite, polyethylene and other synthetic light composites. The substrate can be thinned after the deposition of the silicon detector by mechanical means, chemical etching or laser ablation techniques, or reactive ion etching. Chemical etching is a very effective method of removing glass and is used widely for making microchannel plates where etching of glass fibers to a depth of a few millimeters is routinely done. Likewise, excimer laser ablation is used to remove top layers of materials with micrometer precision.

In some x-ray imaging applications, the substrate can be the scintillator itself. For example, scintillating glass can be used as the substrate for the photosensor array and the x-rays can be directed first through the photosensor on to the scintillator. This reverse illumination method results in the production of x-ray induced scintillations close to the photsensing element which results in minimal light diffusion and loss in spatial resolution. Moreover, because of the proximity to the photosensors and the lower self absorption of light by the scintillator, this method is expected to produce a stronger signal per absorbed x-ray in the scintillator than the conventional front-illumination technique.

Although this method can be easily applied to amorphous silicon areas or linear photosensors, it can also be applied to other image sensors such as CCDs which are used with a scintillator, but they can tolerate a significant amount of direct x-ray interactions also applicable to selenium detectors using scintillators. The reverse illumination method not only allows for increased spatial resolution and the higher signal per absorbed x-ray, but it can reduce the backscatter of x-rays onto the scintillator.

FIG. 25C shows a similar reverse illumination approach, but the substrate of the a-silicon includes a spatially-coherent fiberoptic plate 850. The fiberoptic plate is sufficiently thin to minimize x-ray absorption. A thickness of one millimeter or less is desirable. The fiberoptic plate can be made of conventional low x-ray absorption glass or a fiberoptic scintillating glass. In this method, x-rays pass through the patient and a fraction is absorbed in the first scintillator 852. The light emitted is directed through the fiberoptic onto the photosensing elements of amorphous silicon or amorphous selenium where it is detected, while most of the x-rays penetrate the fiberoptic plate and silicon photosensors to interact with the scintillator 848 on the other side of the photodetector plate. Light emitted from the scintillator 848 is detected by the photodetector elements.

Figure 25E:
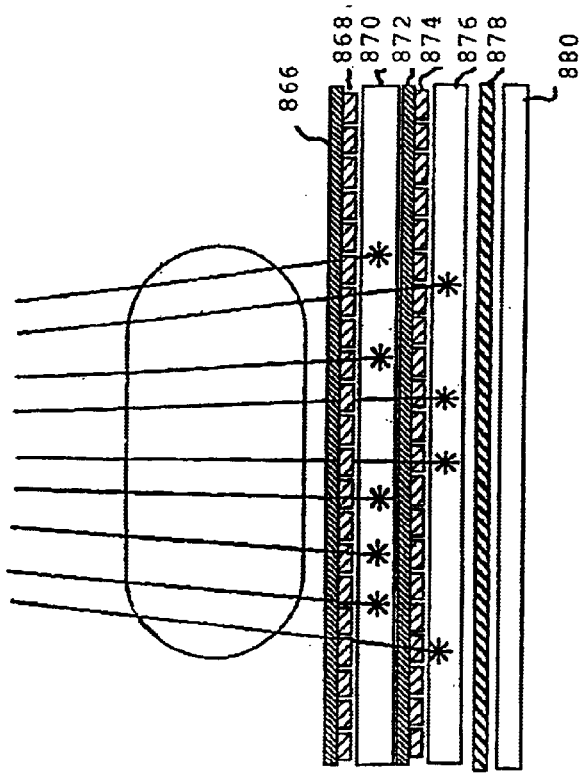
FIG. 25E illustrates a preferred embodiment in which both detectors are coupled to the scintillators on the back.
Figure 25D:
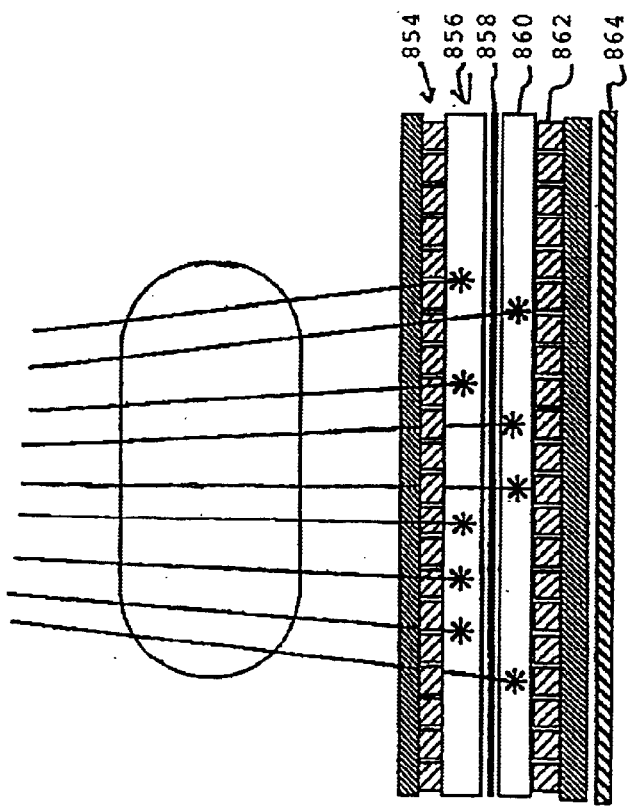
FIG. 25D illustrates a preferred embodiment utilizing two scintillators and two detectors.

FIG. 25D shows another embodiment utilizing the reverse illumination method but instead of a single detector a sandwich of detectors is used. In this embodiment, x-rays transmitted through the patient pass through the thin substrate of the first detector 854 undergoing minimal absorption.

Then a significant number of x-rays interact with the first scintillator layer 856 where they produce useful signal, which is detected by the first detector array. X-rays not detected by the first scintillator pass through the optical isolation layer 858 which is essentially transparent to x-rays, and interact with the second scintillator 860 where they produce useful signal which is detected by the second photodetector array 862. This detection approach can achieve higher spatial resolution than a single thick scintillator shared on each side by each detector array. Moreover, dual-energy separation can be achieved because the first detector array detects mostly the lower energy x-rays, while the second detects mostly the higher energy x-rays. The individual resulting images may be combined for increased signal, or analyzed for dual energy.

FIG. 25E shows a stack of the same detectors, but both photodetectors 868, 874 are in the reverse illumination geometry. In this geometry, x-rays which pass through the patient penetrate the first photodetector substrate 866 and photodetector thin film with minimum absorption, and they are detected by the first scintillator 870 where they produce useful signal. The remaining fraction of x-rays pass through the substrate 872 and photodetector array 874 of the second detector with minimal absorption, and they are detected by the second scintillator 876 where they produce useful signal. On the other side of the detector, a lead or other heavy elements shield 878 is used for safety purposes and for suppression of backscatter. The detector electronics 880 can be placed behind the lead shield. This detection geometry favors higher resolution, x-ray imaging, and dual energy quantitative imaging capability.

Figure 25G:
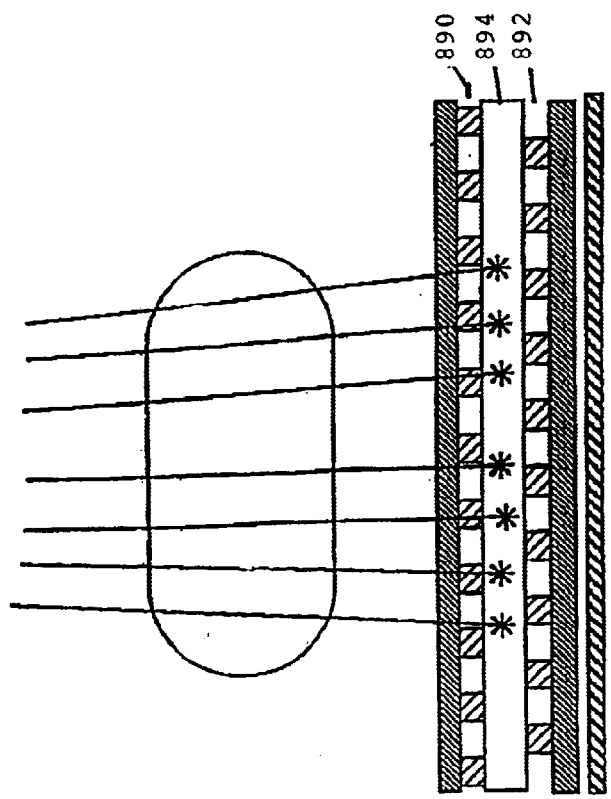
FIG. 25G illustrates a preferred embodiment using two staggered detector arrays having a single phosphor layer.
Figure 25F:
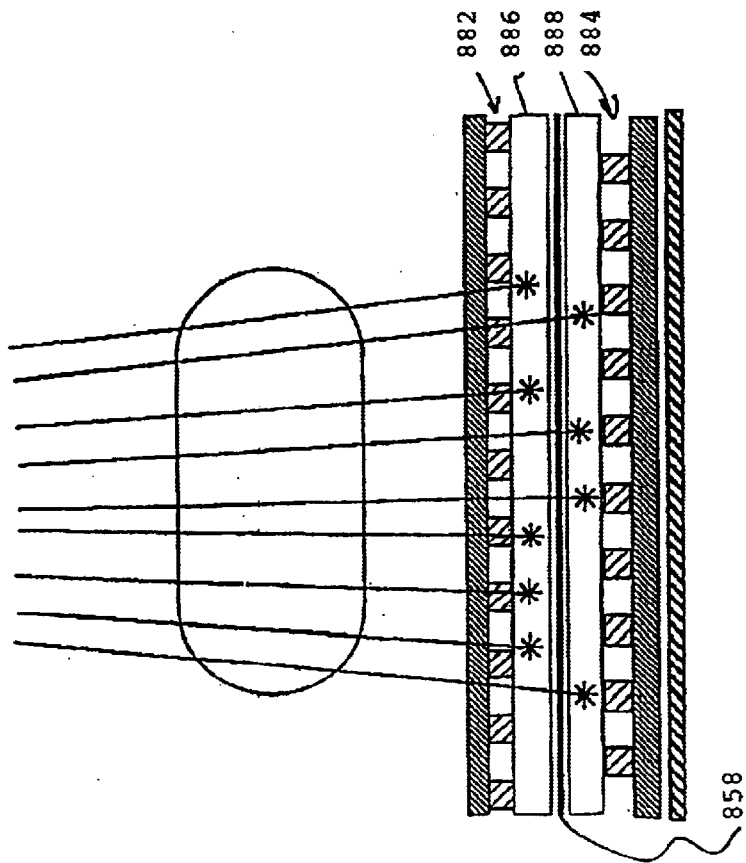
FIG. 25F illustrates a preferred embodiment in which two optically isolated detector arrays are staggered.

FIG. 25F shows the sandwich detector approach, but each detector 882, 884 has a staggered array of photosensitive elements with respective scintillators 886, 888. Detector arrays with densely spaced photodetectors are expensive and difficult to produce for large area coverage. Therefore, a number of stacked and staggered detector arrays can be used to fill the gaps. The schematic shows this arrangement only in one dimension, but the two dimensional approach can also be employed. In this schematic, two identical arrays of the photodetectors are shifted by one pixel. As many as four detector arrays can be stacked in this configuration, and the use of a thin substrate is very important in order to suppress parallax effects. Each detector array may be positioned in the reverse or front illumination as described earlier.

FIG. 25G is similar to the previous Figure, but in this embodiment, a single scintillator 894 is shared between the two photodetector arrays 890, 892.

A particular application of the methods and systems described herein for detecting and imaging of soft tissue lesions includes digital mammography using CCDs or similar type silicon-based detectors such as amorphous silicon type detectors described above. These systems are used to detect lesions in the tissue including calcified material within the soft tissue, that can indicate the need for more careful diagnostic procedures and/or treatment of the patient. Slot-scanning approaches using time-delay integration, where the CCD records continuously during a scan as described herein, can be used for digital mammography. However, the continuous recording approach results in certain problems, particularly with artifacts due to the shear distortion of the fiber-optic plates which can be used with such an embodiment. While slot-scan approaches using the continuous record mode can be used, the quality of the images is less than ideal due to the distortion effects.

Other methods for scanning the breast include the dividing of the image area into four quadrants or even a greater number of segments. Every time it is necessary to take multiple exposures of the breast, the associated problems including increased exposure level and collection time can limit the variety of applications for which the system can be used. It is desirable, therefore, if one needs to acquire the image in a step-wise fashion, that there be no more than two, or at most, three acquisition steps. If one uses a greater number of acquisition steps, the breast has to remain compressed for too long, thus causing extreme discomfort to the patient. Moreover, the x-ray tube power requirements increase significantly. The preferred method for digital mammography applications involving sequential multiple imaging is thus limited to a two image acquisition process. This procedure involves directing x-rays from the source through the tissue to the stationary detector system for about 0.2–5.0 seconds and preferably in the range of 0.5–1 second, the detector system can then be moved to a second position while the first image is read out, then a second exposure is obtained and read out. As many as 2–5 million pixels can be read out in a time interval that is less than the exposure interval.

A problem associated with the two-dimensional array approach, is its complexity and cost. Although the tiling of 4×3 CCDs, for example, to form an array can be used for digital mammography, it is likely to be too expensive for many common applications. This results from the cost of the CCDs themselves, and with the problems associated with making a seamless joint to three or four sides of the CCDs.

Referring to FIGS. 26–32, the detector module 900 can consist of from 3 to 5 CCDs in a first linear array 902 and another set of CCDs can be positioned approximately 6 cm apart in a second linear array 904. This embodiment utilizes four CCD elements in each array. Each element can include a scintillator 906 and a tapered fiber optic plate 908. In the embodiment where the CCDs are replaced by amorphous silicon sensors, a single strip silicon sensor can be substituted for each linear array in these embodiments.

The first set of CCDs can be placed as closely as possible to the chest wall of the patient. The x-ray beam is collimated by using a double slot to provide two fan beams, each fan beam being directed onto a linear array, thus only two areas are irradiated which correspond exactly to each CCD group. After one x-ray exposure and acquisition, the x-ray collimator is translated in synchrony with both CCD banks which are also translated to the next position. Another exposure is taken and the signal is read out. A small amount of overlapping of the fields, about 1–3 mm can be desirable. With the use of a micro-stepping translation stage the successive fields can be aligned to within a few microns with or without overlap. The images can then be joined and will be substantially seamless with less than a 5–10 micron difference between the region of the body and the joined images of the region.

Figure 27:
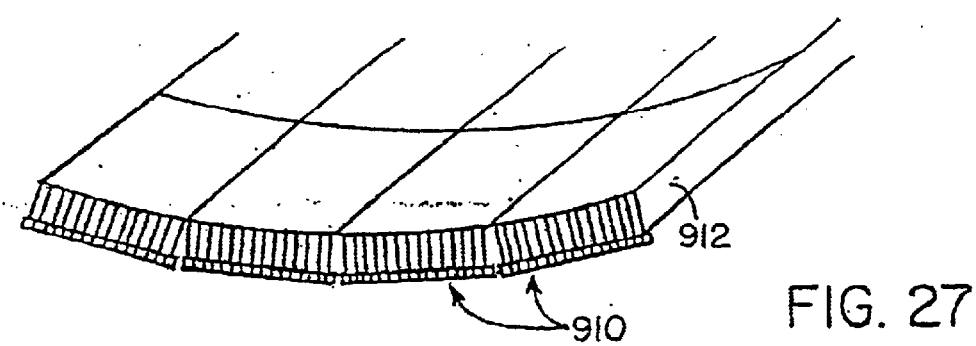
FIG. 27 illustrates another preferred embodiment in which the imaging elements in each linear array positioned at a different angle relative to the patient and the x-ray source.

The sensing surface does not have to be on a plane. As shown in FIG. 27, the CCDs 910 can be arranged on a curving or non-planar surface. This is an extremely important embodiment because it provides for the use of straight (non-tapering) fiber-optic plates 912 which dramatically reduces the cost and contributes to better image quality. Please note that the CCDs can be cooled or non-cooled and can be operated in the pixel binned or non-binned mode. Additionally, an anti-scatter grid can be used between the breast and the detectors. Each element 910 in the array is generally equidistant from the x-ray source in order to reduce distortion across the entire field of view of the array. This arced linear array can be used for many different applications as described elsewhere herein.

Figure 28:
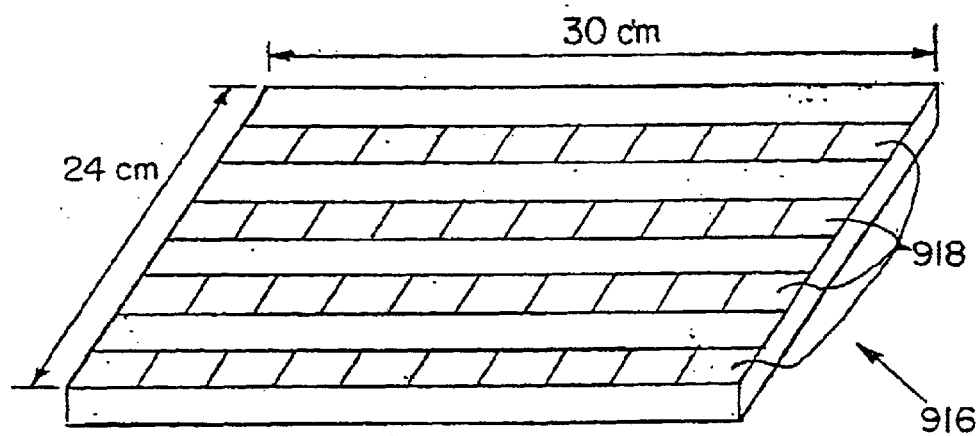
FIG. 28 illustrates a preferred embodiment in which a large number of imaging elements are arranged in a large array conforming in size to a standard x-ray film cassette which can have three or more spaced linear arrays.
Figure 29:
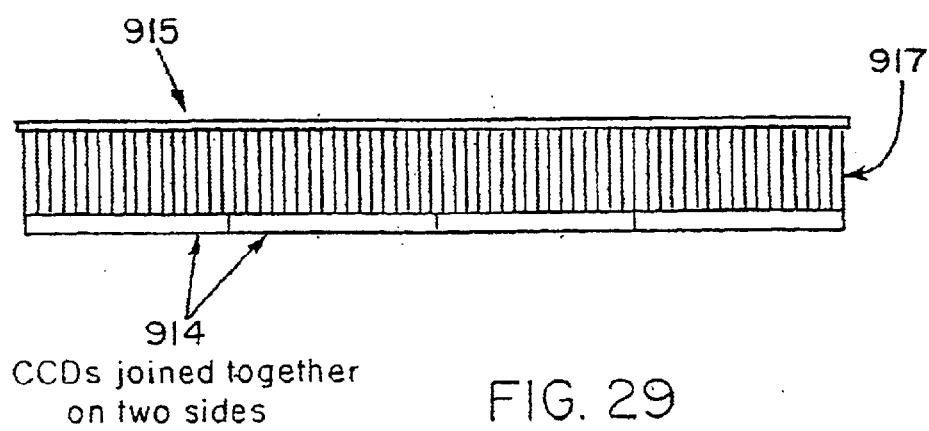
FIG. 29 illustrates a cross-sectional view of a linear array using a common fiber-optic plate and scintillator.

This approach is preferable as current manufacturers can readily make CCDs which are buttable on two sides. It remains difficult and expensive to make CCDs buttable on three or four sides. In the illustrated embodiment there are only six joints required between the CCDs, unlike a large area cassette which has many more. A typical CCD for this application can have an area of 6×6 cm but for economy reasons, one can use a larger number of CCDs, such as 3×3 cm elements. For example, if one uses a 3×3 cm device, each CCD linear array 902, 904 incorporates eight CCDs for a total of 16 CCDs. This can also be used to provide a larger area of coverage comparable to a standard large film cassette. FIG. 28 illustrates a four line separated array 916 covering a 24×30 cm planar area with 10 of the 3×3 cm devices in each line 918. In FIG. 29, a partial cross sectional view of one of the lines 918 in FIG. 28, illustrates a preferred embodiment in which each CCD 914 is butted against one or two adjoining CCDs in each line with each line coupled to a scintillator 915 and a fiber optic plate 917. The two-step acquisition is preferable relative to the narrow slot-scanning approaches which typically use a slot width of about 1.5 cm, and the larger area imaging approaches which are effective but can be extremely costly.

Figure 30:
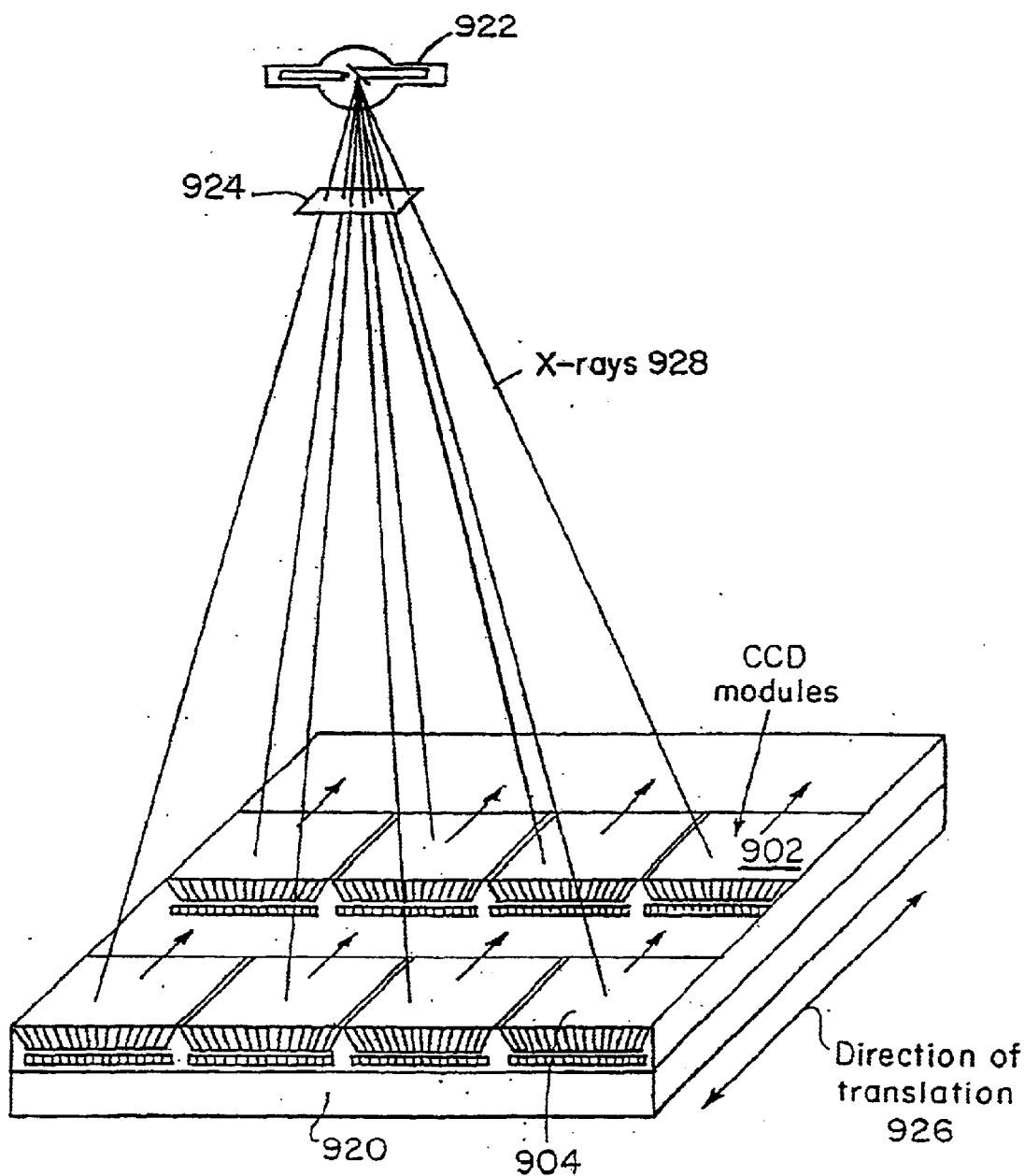
FIG. 30 illustrates a system for translating the array relative to a radiation source.

As illustrated in FIG. 30, an x-ray source 922 and a double or multiple slot collimator 924 can be used to generate and align the x-rays 928 with the translating CCD modules. An actuator or motorized system 920 is used to translate both CCD arrays 902, 904 without altering the distance between the rigidly aligned CCD arrays. The system 920 can be connected to a controller or personal computer as described previously so that the user can control array position along the direction of translation 926, which in this embodiment, is towards or away from the chest wall.

Figure 31A:
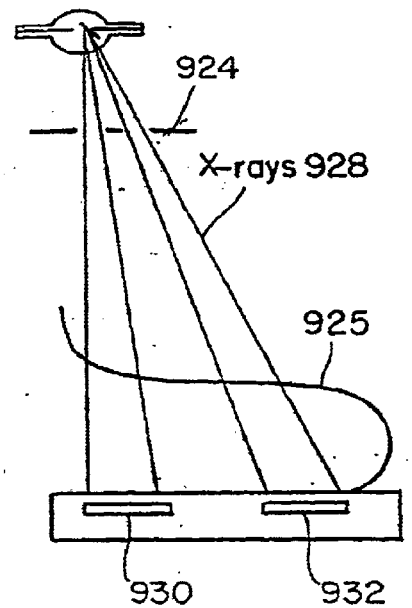
FIGS. 31A and 31B illustrate the process of a two step imaging sequence.
Figure 31B:
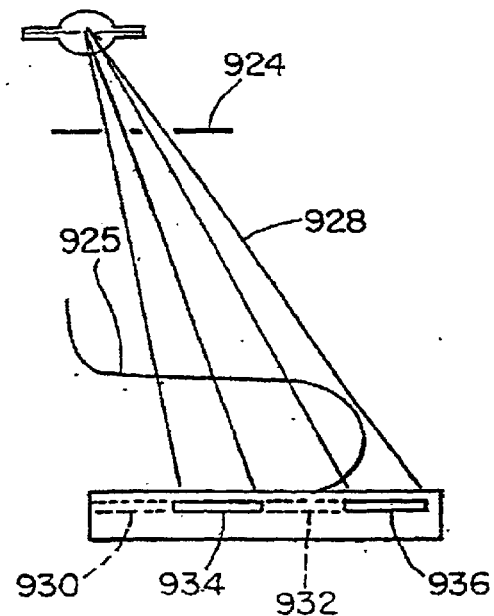

As shown in FIGS. 31A and 31B, the arrays 902, 904 are positioned to image two parallel regions 930, 932. The detectors 902, 904 are then translated from the first position to a second position to image and analyze two further parallel regions 934, 936 to provide a full image of compressed breast 925. The relative spacing between the two linear arrays can also be controlled to increase or decrease overlap. A preferred embodiment, however, retains the two spaced arrays in a rigid position relative to each other. This particular embodiment moves the detectors towards or away from the chest wall of the patient.

Figure 32:
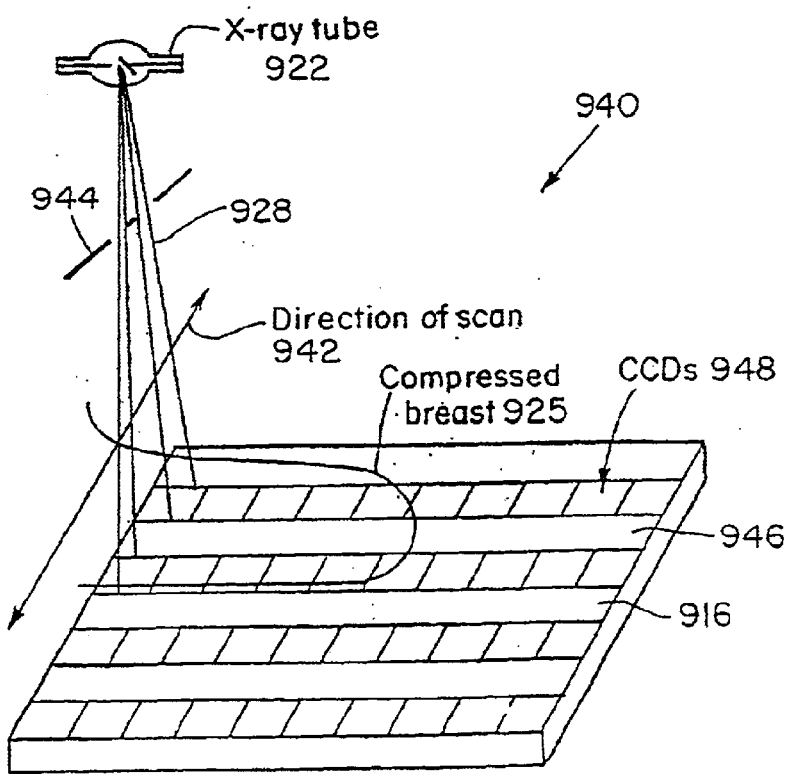
FIG. 32 illustrates a system for sequential imaging or scanning of tissue in which the array is moved relative to a source.

Shown in FIG. 32 is an embodiment 940 in which the array 916 of FIG. 28 in which the direction of scan 942 is along the chest wall. The collimator 944 is also moved along the same axis as the array to direct x-rays 928 onto the CCDs 948 and not onto the spaces 946.

Figure 33A:
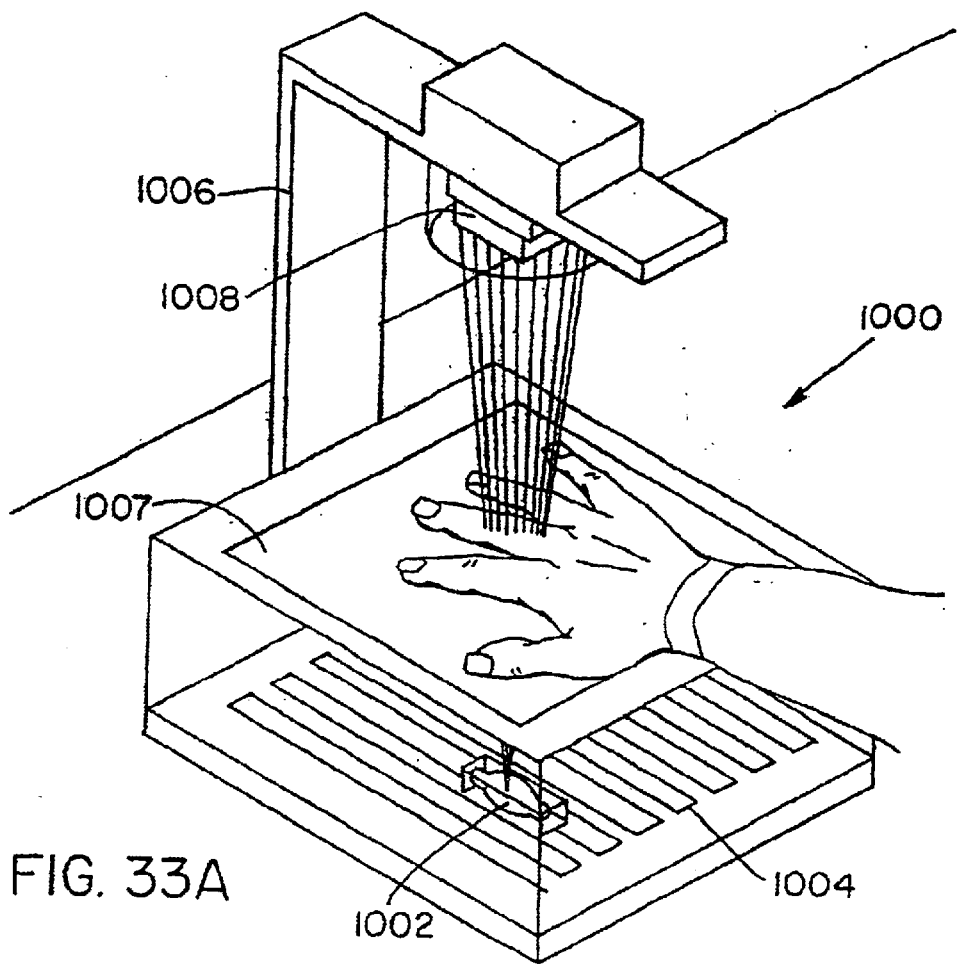
FIGS. 33A and 33B illustrate perspective and top cross-sectional views of a peripheral scanning x-ray imaging system in accordance with the invention.
Figure 33B:
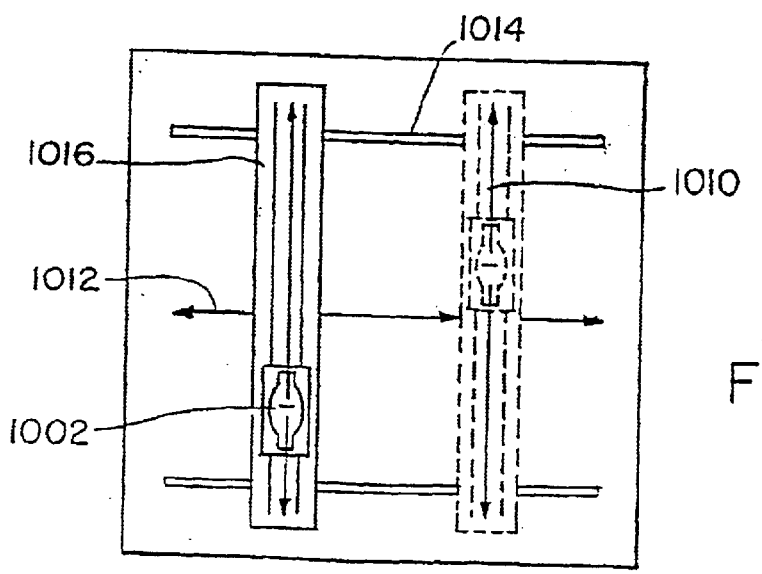

Illustrated in connection with FIGS. 33A–33B and 34A–34B are digital x-ray imaging systems for scanning of peripheral anatomy such as the hand. Shown in FIGS. 33A and 33B is a preferred embodiment 1000 in which the x-ray source 1002 is positioned directly underneath the platform 1007 on which the hand is placed. The source 1002 can be attached to a C-arm 1006 and is rigidly aligned with a detector 1008. The source 1002, detector 1008 and C-arm 1006 can be mounted on a support 1016 shown in the top view of FIG. 33B. The detector can be placed in close proximity of the hand or a few centimeters away to provide a magnified image. The support 1016 can move back and forth along axis 1012 supported by rails 1014. The source 1002 can also be moved along axis 1010 over the support 1016. This structure is driven in each direction using motor and control systems to provide a rectilinear scan 1004 as shown schematically in FIG. 33A. The system can be used to make morphometric measurements of the hand or other peripheral locations.

Figure 34A:
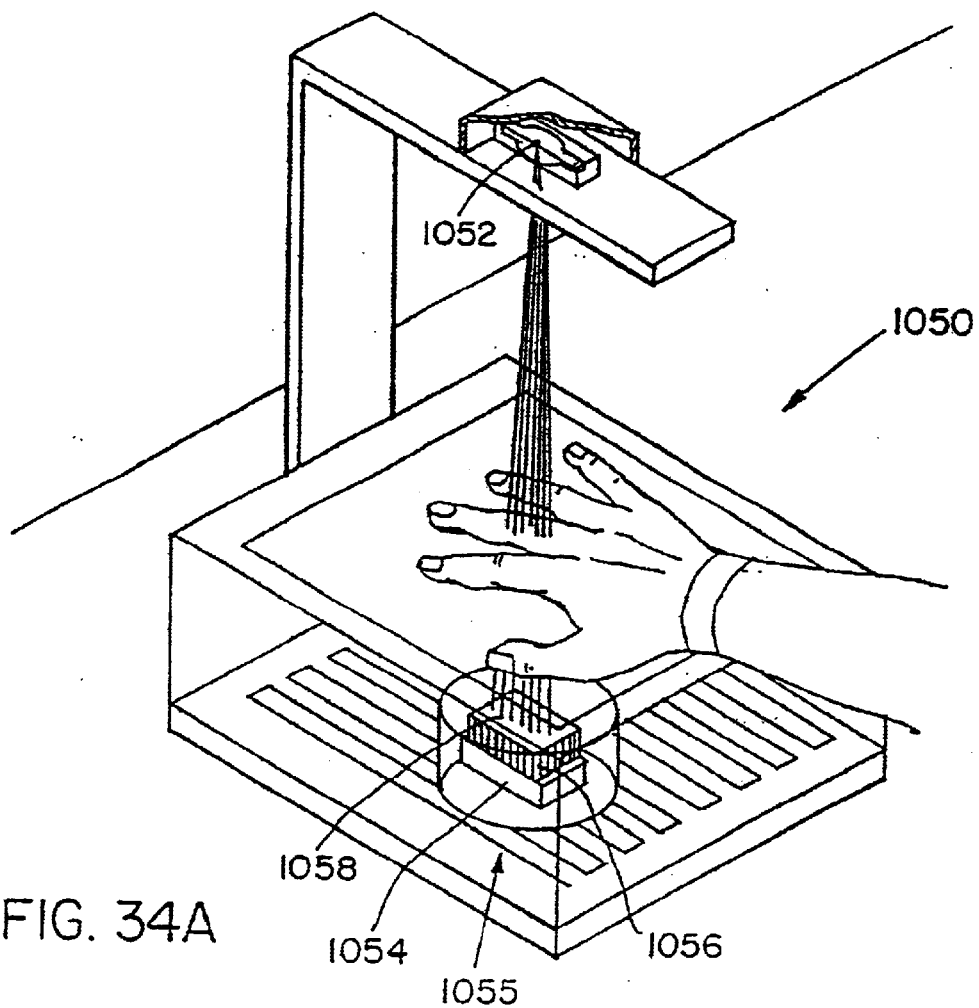
FIGS. 34A and 34B illustrate another preferred embodiment of a peripheral scanner in accordance with the invention.
Figure 34B:
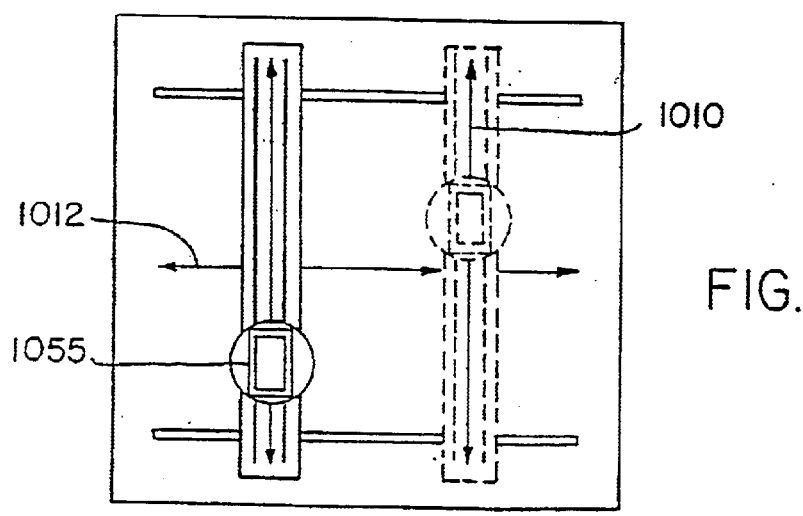

Another preferred embodiment 1050 is schematically illustrated in FIG. 34A. In this embodiment the source 1052 is attached to the C-arm above the region to be imaged. The detector 1055 is positioned underneath to scan along axes 1010 and 1012 as shown in FIG. 34B. In this particular example, the detector system 1055 includes a scintillator 1058, a fiber-optic plate 1056 and a CCD 1054. Note that in the rectilinear scanning approach, the imaging detector 1008, 1055 can be a CCD or charge-injection device (CID), a complimentary metal oxide semiconductor (CMOS) detector, a zinc cadmium telluride detector, a pixellated amorphous silicon detector, a position sensitive photomultiplier tube, or an amorphous selenium detector. The stacked detector approach described earlier (FIGS. 18 and 19) can also be used in this embodiment.

The digits or other bones in the hand such as the distal radius can also be imaged by a single snapshot, using a fiber optic taper, or a lens as previously described. Dual energy can be accomplished also by two successive exposures at two energies with filtration. Another desirable system is to use either a straight fiber optic plate taper or a taper using a very small demagnification, between 1—1 and 3–1 for example, and compose an image by scanning in rectilinear fashion. The readout can be performed by a time delay integration (TDI) or by frame transfer or by full frame snapshot. All three readout modes are well known in CCD imaging. In the frame transfer and snapshot modes an essentially seamless image is composed by joining adjacent frames. The time delay integration method can also provide a seamless image from different scanlines. Demagnification for a static imaging system can be between 3–1 and 7–1.

The dual-energy approach has been shown to be extremely effective for the quantitative measurement of tissue densities and the most widespread application of this technique is in bone densitometry. Current approaches to dual energy scans use switchable tube potential (kVp) and filtration, or alternatively, a split detector approach. The former approach adds to the complexity, size and cost of the instrument. The split detector approach is currently implemented on systems using a linear detector array with relatively large detector elements. In the split detector method, two adjacent detectors are assigned to a single volume element in the body. One of the two detectors is blocked by an x-ray absorbing filter, while the other detector has no added filtration in front of it.

In existing systems, the spatial resolution of split detector systems is limited to relatively low spatial resolution. The typical minimum detector size is about 1 mm for prior art systems. If the detectors are made smaller for higher spatial resolution (for example, 0.5 mm) the design and manufacture of the filter at this size level becomes difficult due to the limitations of the conven-tional mechanical techniques of cutting and forming filter materials. For example, if we need to make a split detector with 250 micron pixels (500 microns per pair), a filter with dimensions of 250 microns×250 microns must be placed over every other pixel. Therefore, current practice is limited to the millimeter scale filtration only. A two-dimensional imaging device capable of simultaneously detecting high and low x-ray energies has many appli-cations, including dual energy bone densitometry, mammography and angiographic imaging.

A preferred embodiment uses a microscopic patterned film which can be placed appropriately in front of an x-ray detector such as a CCD. The film can include, for example, a checkerboard-like pattern of material which produces an alternating attenuation of x-rays. For example, the film material can be a metal (e.g., copper molybdenum, iridium, palladium, indium, cadmium, tin, iodine, barium, terbium compounds, tungsten tantalum gold, Pt, Aluminum and cadmium and various known alloys and compounds of these materials, lead, lead glass, lead acrylic, lead plastics) or other x-ray attenuating foil. A typical pattern can consist of elements as small as a few microns, for example. Such a pattern can be manufactured by using micromachining techniques. Such techniques include excimer laser ablation, electroforming or vapor deposition techniques, chemical or photochemical etching, or reactive ion etching techniques. The pattern can consist of a filter element followed by a blank element, or by a variation of thickness between adjacent elements. Due to the high absorption characteristics of many materials which can be used as x-ray filters, the thickness of the film can be, for example, between 20–2000 microns.

The x-ray filter can be placed at an appropriate distance between the x-ray source and the CCD or other detector, and each area element can be aligned to correspond to the detector pixels. In this configuration, the signal detected by the blocked pixel represents mostly the high energy, because most of the low energy component of the x-ray spectrum has been absorbed by the filter. The unblocked detector pixel represents the signal from the entire spectrum (high and low energy). From this information, the densitometric properties of tissues can be computed by conventional methods.

Figure 35B:
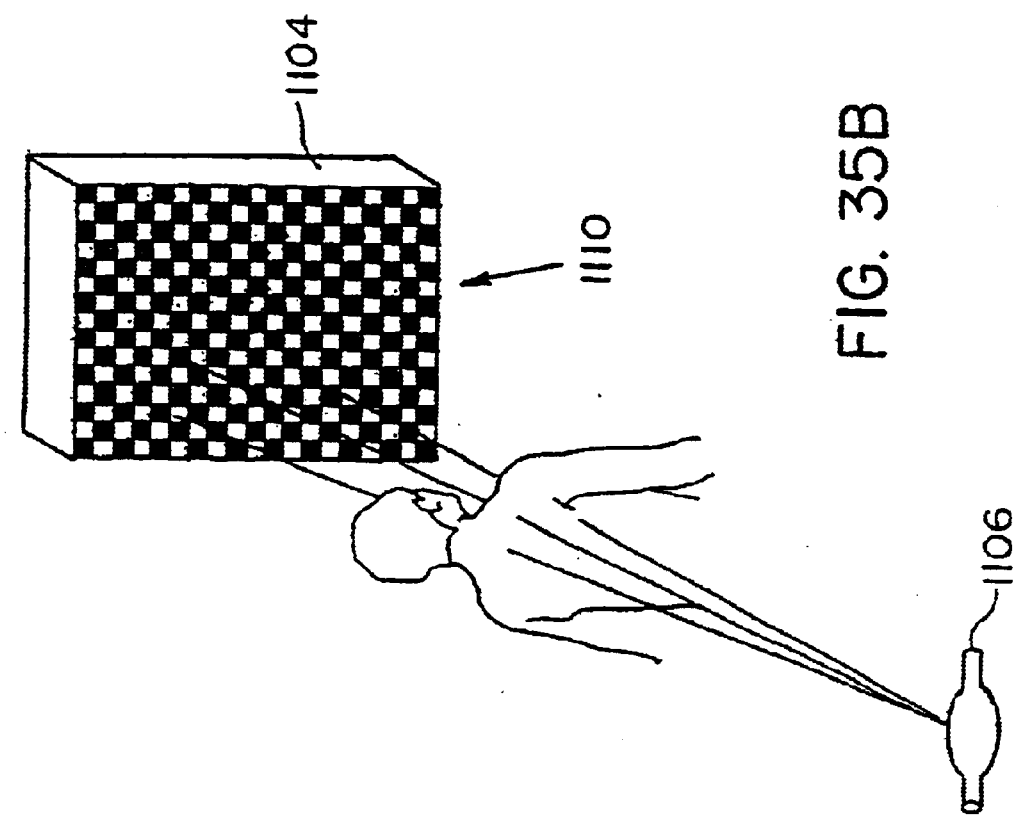
FIGS. 35A and 35B illustrate preferred embodiment of a microfabricated filter system for dual energy x-ray imaging in accordance with the invention.
Figure 35A:
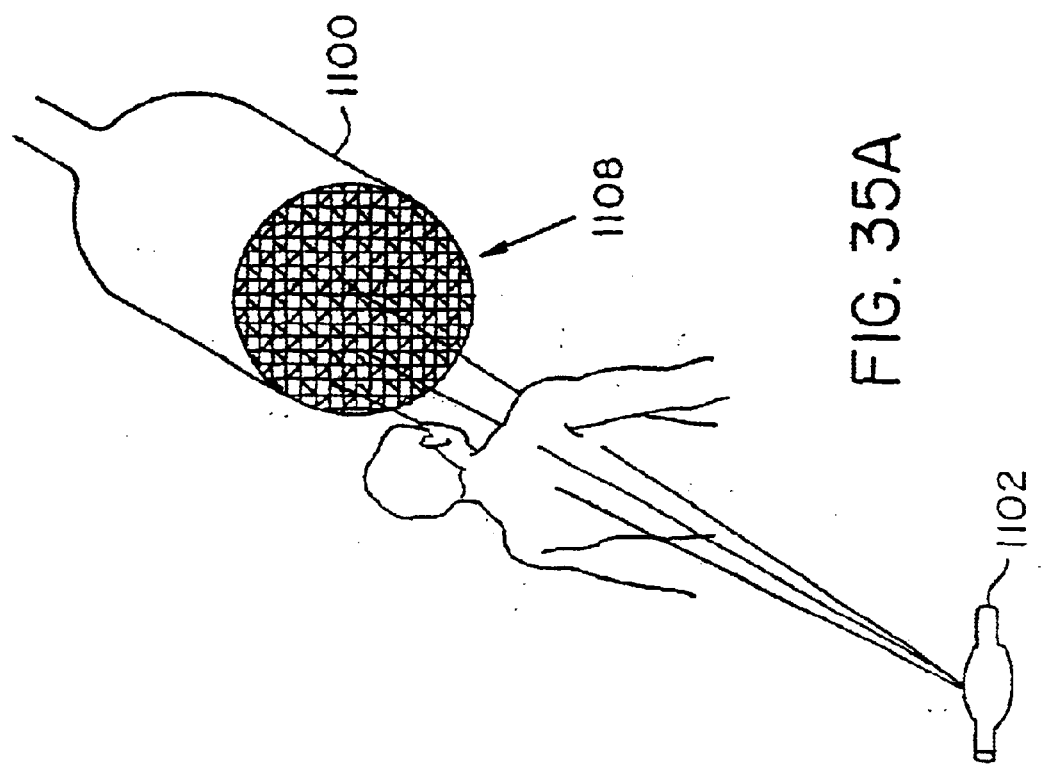

In one embodiment, the x-ray absorbing film is placed in front of a fiber optic plate. Note that the detector can be a conventional image intensifier 1100 as shown in FIG. 35A, or a flat panel detector 1104 as shown in FIG. 35B, such as a CCD, a CMOS detector, an amorphous silicon area detector, an array of photodiode detectors, an amorphous selenium detector, or a zinc cadmium sulfide detector. The x-ray source 1102, 1106 containing both energy levels is directed through the region of the patient being studied and onto the film 1108, 1110. This can also be used with a linearly scanning rectangular array in which a plurality of pixels extend in the direction along the scanning axis and a much larger number of pixels in the orthogonal direction.

Alternatively, the scintillator, or the photocon-ductive material in the case of selenium or zinc cadmium telluride, itself can be formed in a checkerboard pattern by using the above techniques. This provides a scintillator with alternating thickness across its entire surface. Therefore the scintillator can be used for discrimination between high and low x-ray energies. In the case of the non-scintillator based detectors, such as amorphous selenium or zinc cadmium sulfide, the detector can be manufactured in a similar fashion to yield the desired results. In both detector types, the filter pattern does not have to be square; it can be rectangular, circular, or of any other desired shape. Alignment of the pattern with the detector pixels, can be accomplished in a number of ways. One method is to position the film between a light or x-ray source and the detector. Running the CCD in the zoom imaging mode can be used to position the film in the proper alignment and secure it by mechanical methods, such as bonding compound. A micrometer stage can be used for these alignment procedures. The above technique can be used not only for the two-dimensional detector, but also for a linear detector.

Figure 35C:
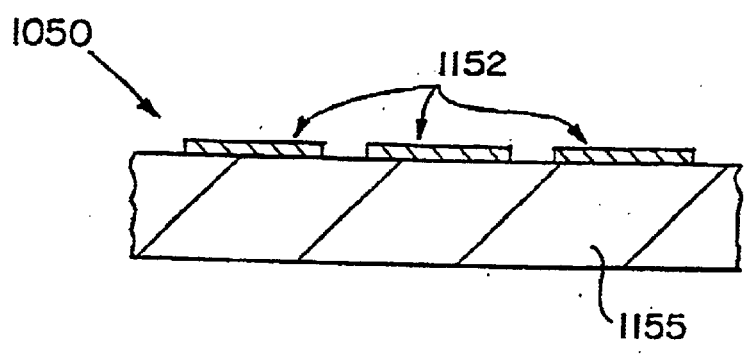
FIGS. 35C(a)–35C(d) illustrate a preferred process sequence for fabricating a filter system as shown in FIGS. 35A and 35B.
Figure 35C:
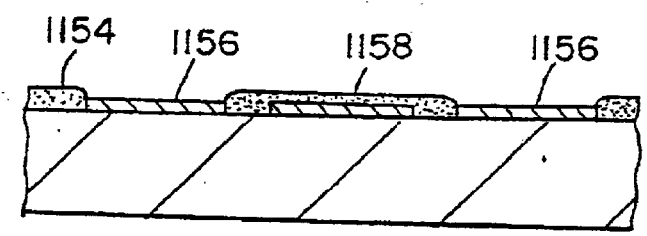
Figure 35C:
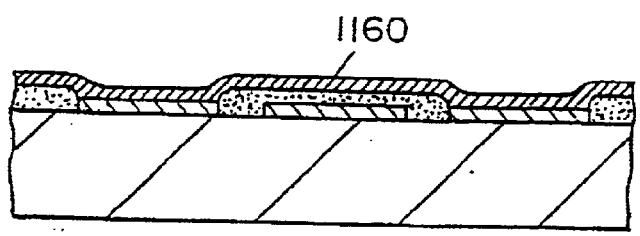
Figure 35C:
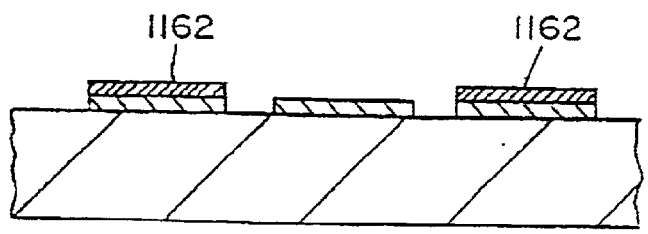

Illustrated in FIGS. 35C(a)–35C(d) is a process sequence for fabricating a pixel filter array in accordance with the invention using techniques known in the semiconductor industry. FIG. 35C(a) illustrates a CCD or other array detector 1150 having pixel elements 1152 formed on panel 1155. A mask or patterned sacrificial layer 1154 is then deposited and patterned to cover selected pixels 1158 and expose selected pixels 1156 (FIG. 35C(b)). As seen in FIG. 35C(c) the filter material 1160 is formed over the entire structure. The film can be an evaporated metallic film. The thin-film filter material is then patterned and the excess material is removed to expose the mask 1154. Finally, the mask 1154 is removed to provide the final patterned device with thin film filter array 1162, as shown in FIG. 35C(d). These pixels 1162 can also be formed on an x-ray transparent or transmissive panel that is mounted relative to the detector.

An alternative method of acquiring a dual-energy image is to use a pair of stacked phosphors which emit at two substantially different wavelengths. In this embodiment, two phosphors, one green and one red, for example, are used in conjunction with a lens, a CCD or other area detector described herein. A single CCD or other sensor and a microstructure optical filter between the phosphor stack and the image sensor provides a dual energy capability.

Certain scintillator (phosphors) can store x-ray energy after x-rays or gamma rays interact with the material. After the phosphor is exposed to x-rays, a laser beam is scanned over the plate and during this process, the laser light energy stimulates the phosphor to release a substantial portion of the x-ray energy, which has been stored. As a result of this photostimulation process, the phosphor emits light which is typically in the UV-blue region of the electromagnetic spectrum typically between 380–420 nm, for example. One preferred embodiment uses the barium fluoro-halide phosphors available from Fuji Photo Film Co., Ltd or Eastman Kodak Company. This light is detected typically by a single channel, photomultiplier tube. The positional information is encoded by tracking the position of the laser beam by some optical or electro-mechanical system. In this process the image is constructed using the rectilinear scanning movement of the laser beam, and image formation is done on a point-by-point basis.

In an alternate preferred embodiment, a flash-emitting, wide-apertured light source, as opposed to a narrow-apertured laser, is used to stimulate the phosphor. The light pulse created by this flash-emitting light source simultaneously illuminates the entire imaging area on the opposing face of the photostimulable phosphor with sufficient intensity to stimulate the transmission, at a single moment, of a two-dimensional image of the entire x-ray pattern. Accordingly, the image can be instantaneously generated and recorded using a pixelated CCD to produce a snapshot, in contrast to the scanning point-by-point process of the prior art.

In similar uses of stimulable phosphors for general radiography, the energy from the x-rays stored in the phosphor plate is stimulated by a scanning laser beam in a raster fashion to stimulate the plate on a point-by-point basis. Use of the scanning beam approach, however, requires a relatively long period of time to read the entire plate and requires complex and costly moving mirrors and optical components to accomplish this task. Any vibrations or misalignment of these components can damage the radiographic image quality. Moreover, only a fraction of the stored signal is stimulated by the laser beam due to the fast rate of scanning. A significant amount of useful signal remains on the phosphor plate which is never recovered. If the phosphor plate is scanned slowly enough to capture most of the useful signal, the readout time can be impracticably slow, perhaps in the order of several minutes. Alternatively, a super-fast optical scanning system can be used with a higher power laser beam; however, this approach is likely to be expensive, bulky and impractical for most clinical imaging applications.

Moreover, those using laser scanning systems have recorded the stimulated light output using photomultipliers which merely record the intensity of light output as a function of time. The position of the laser is then correlated with time and the image is reconstructed. Spatial resolution and contrast is sacrificed with this method, however, because some of the laser light scatters within the phosphor such that areas of the phosphor remote from the laser are stimulated. Without means for detecting the position from which light emanates and strikes the receiver, the absence of a pixelated CCD produces a loss of image quality. The use of a single light pulse and pixelated CCD, as described by applicant, thereby allows for more accurate resolution as a result of its ability to more closely identify the position of light produced from scattering within the phosphor.

Image sensor saturation may result as a consequence of the large variation in the exposure incident on the photodetector. In the case of dental imaging for example, the part where the x-ray beam is not attenuated by dental tissue is likely to produce signal saturation in the CCD or other detector.

Pixel saturation can be controlled, however, by adaptive multiple excitation and sampling of the area detector. Instead of reading out the phosphor with a single excitation and detection, the stimulable phosphor is read out by a number of excitations and readouts. In most cases, two to five excitation s and readouts will be sufficient. The individual images can be added and averaged in order to increase the signal-to-noise ratio and overall detectability. In a variation of the above approach, a presampling low-intensity excitation pulse may be applied. The low-intensity excitation pulse will extract only a small portion of the stored energy in the phosphor. Most of the energy will remain for the final excitation. This presampled image is not of high radiographic quality but it contains adequate information to delineate the anatomy and therefore the areas of the high and low x-ray attenuation in the image. This image information can be routed to a spatial light modulator. The spatial light modulator may be placed in front of the excitation beam in order to spatially modulate the spatial distribution of the light. Therefore, the areas where the sensor receives very high exposure correspond to the areas of the spatial light modulator where the greater absorption of light will occur. Examples of suitable spatial light modulator include commercially-available liquid crystal displays.

The application of CCDs and other area detectors to x-ray imaging tasks usually employ conventional phosphor material, which emits light promptly after x-rays interact with it. This method works quite well for some applications, but it may not be optimal for x-ray imaging tasks, where the exposure time is relatively long. For example, in mammography, exposure times in the order of 1–6 seconds are very common. During the x-ray exposure, the CCD must be in the signal-collection mode in order to record the light emitted from the phosphor. However, in addition to the signal, which is generated in the CCD as a result of the light detected from the phosphor, the CCD also accumulates dark current, which is a spurious signal generated by thermal excitations of electrons within the sensor. This dark current signal is detrimental to the final image. In mammography, thermoelectric cooling of the CCD is used in order to suppress the dark current. Cooling of the CCD is extremely effective for this purpose, but it also adds significantly to the cost and size of the device.

In some applications, cooling can be eliminated by using a well-known approach, called multi-pinned phase (MPP). This involves biasing the detector to prevent electron drainage. The MPP technique can be also effective, but it often results in a lower capacity of charge in each pixel of the CCD. This has become an extremely serious problem in the design of mammographic imaging devices, particularly those used for stereotactic localization. The well (pixel) capacity of the CCD is extremely important, not only for adequate dynamic range, but also for avoiding charge saturation, and spillover of charge in areas of the sensor, where the x-ray beam is not attenuated adequately by the tissue. In order to avoid charge saturation, CCD camera manufacturers use pixel readout (clocking) schemes, which can be effective to some degree. However, this also results in higher dark current which is very detrimental to the radiographic image.

A solution to this problem provides a high resolution radiographic image with greatly reduced dark current by using an area or linear detector, such as a CCD, CID or CMOS detector and a photostimulable phosphor. This not only minimizes the dark current, but it can be adapted to avoid pixel charge saturation. This method can also be used for radionuclide autoradiography as the exposure times are also relatively long. This process can be described by the following steps.

Figure 36B:
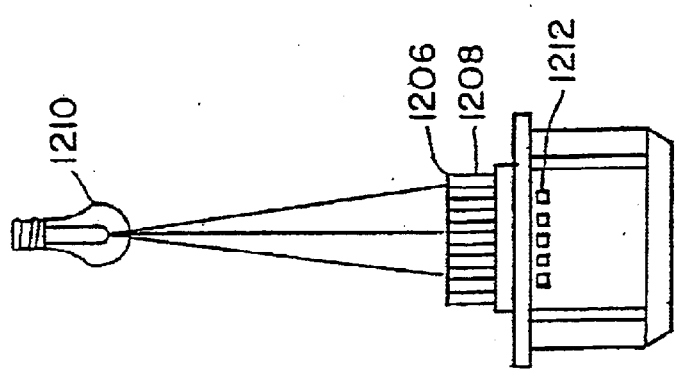
FIGS. 36A and 36B illustrate an x-ray imaging system using an optical storage element.
Figure 36A:
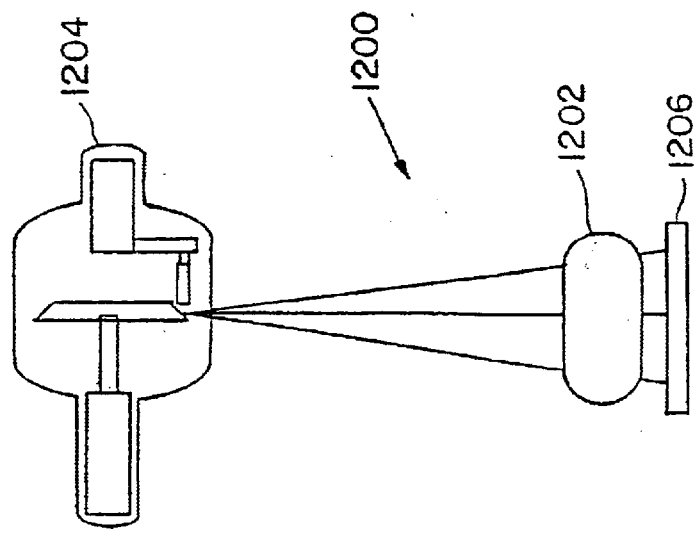

First, leave the CCD in the normal mode (typically in the non-acquisition mode). Next, as shown in FIG. 36A, take an x-ray exposure of the object 1202 or part of the body using an x-ray source 1204 and a photostimulable phosphor storage element 1206. Now the phosphor 1206 has stored the energy within its structure. Then, the x-ray storage element 1206 is positioned between a light source 1210 and a fiber optic plate 1208 over CCD 1212, as shown in FIG. 36B, and the CCD electronics are activated just as if the user was ready to take an exposure. A light pulse is injected upon the phosphor over its entire area. This can be accomplished by an intense light source which irradiates over the entire surface of the phosphor. The CCD sensor starts sensing within a very small time fraction prior to or after the light pulse. A reasonably good synchronization between the injection and the light pulse and the CCD acquisition can be desirable. The duration of the light pulse is preferably much shorter than the duration of the x-ray exposure. Therefore, the dark current, which is time-dependent, is much less in the CCD. A light filter is used in order to reject the stimulating light and detect only the fluorescent light. The CCD is then read out at the end of the light pulse.

The storage scintillator can be stimulated by a light source which irradiates the entire area of the phosphor, or by a scanning light source such as a laser. It is desirable that the light source emits optical radiation in the red, or near infrared, region of the electromagnetic spectrum, typically in the region between 530 to 1500 nanometers. The light source can be filtered appropriately in order to narrow its spectral emission. In this particular application, it is desirable to suppress or completely eliminate the emission of light below approximately 620 nanometers.

In a variation of this technique, the light source may be filtered further in order to limit its emission in a fairly narrow band between 650 and 800 nanometers. Other sources that peak closer to the near infrared approaching about 1,000 nanometers can also be used. Most stimulable phosphors emit light upon stimulation in the region between 380 to 420 nanometers with a strong peak at 400 nanometers. The rationale behind this detection method is to allow most of the stimulated fluorescence to pass through the optical system and be detected by the position-sensitive photo-sensor while blocking almost completely the stimulating light. In order to achieve this, there are various commercially available band-pass filters, which allow extremely high discrimination between red and UV-blue light. One such filter is the Schott BG-3 filter which can be used very effectively for this purpose. By using approximately 4–5 mm thick filter, the ratio of the red to UV-blue pass, can be on the order of 10-10. This type of wavelength discrimination is well known in the art and has been used for other applications, such as Raman spectroscopy. In this particular application, a greater than 10–8 discrimination may be necessary, and this may be achieved by using either a thicker band pass filter, or by using a thin substrate with a band-pass optical coating.

In the case of the lens coupling, the relatively thick filter element, such as BG-3 glass, can be very easily applied, because of the ample distance available between the stimulable phosphore and the lens. This filter can be placed at some point between the stimulable phosphor and the photodetector. If desirable, a thin layer band-pass filter which is typically applied by evaporation techniques, can be applied onto a substrate or onto a band-pass filter glass. Alternatively, the lens itself, or even the photosensor, can be coated with a multi-layer optical coating which can act as a band-pass filter.

While the selective discrimination against the red light and the passage of UV-blue light can be attained in the lens coupling approach, this type of wavelength discrimination is more difficult in the fiberoptic coupling approach as the optical elements are in contact with each other, and there is relatively little freedom to use very thick bandpass filters. However, selective filtration of the red light, can be accomplished by applying a thin coating at some point between the stimulable phosphor and the photosensor. These coatings are typically made by thin-layer deposition techniques and can be made extremely thin, typically less than 50 microns.

Figure 40G:
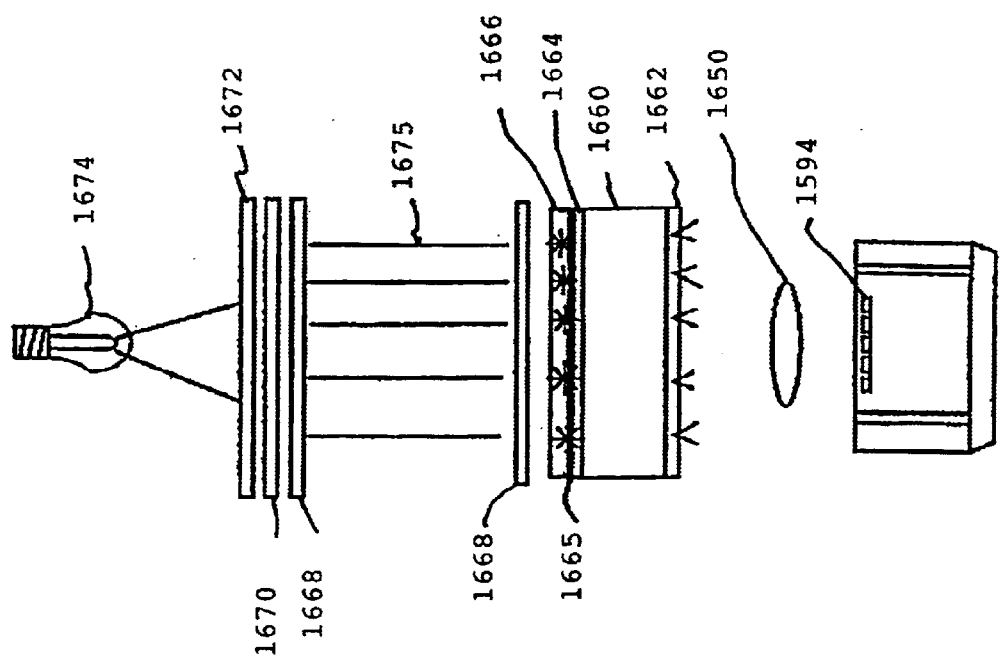
FIGS. 40A and 40G illustrate additional preferred embodiments of an optical stimulation system for detecting a stored x-ray image.

Examples of filtering systems are illustrated in connection with FIGS. 40A and 40B in which a housing 1560 completely encloses the system during readout. In FIG. 40A, a broadband light source such as a xenon arc lamp, a mechanical or electroptic shutter 1504, a bandpass optical filter 1506 that is transmissive in the red or infrared and absorbing in the blue, ultraviolet and green regions of the electromagnetic spectrum. After transmission through an optically transparent compression plate 1510, the incident light falls on the storage scintillator 1512, which in turn emits light of a different wavelength onto a first fiber optic plate or coupler 1514, a thin bandpass optical filter 1516 that absorbs in the red and transmits in the ultraviolet and blue regions. The filter output is directly coupled to a second fiber optic plate 1518 and the area detector 1520.

Figure 40B:
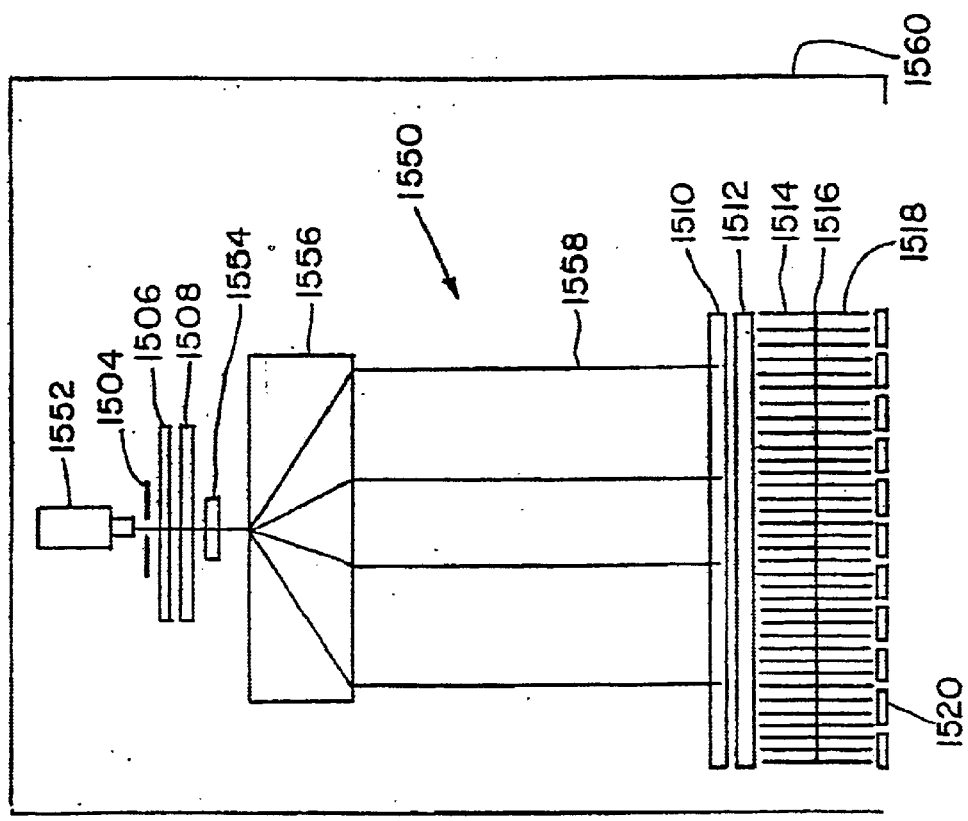
Figure 40A:
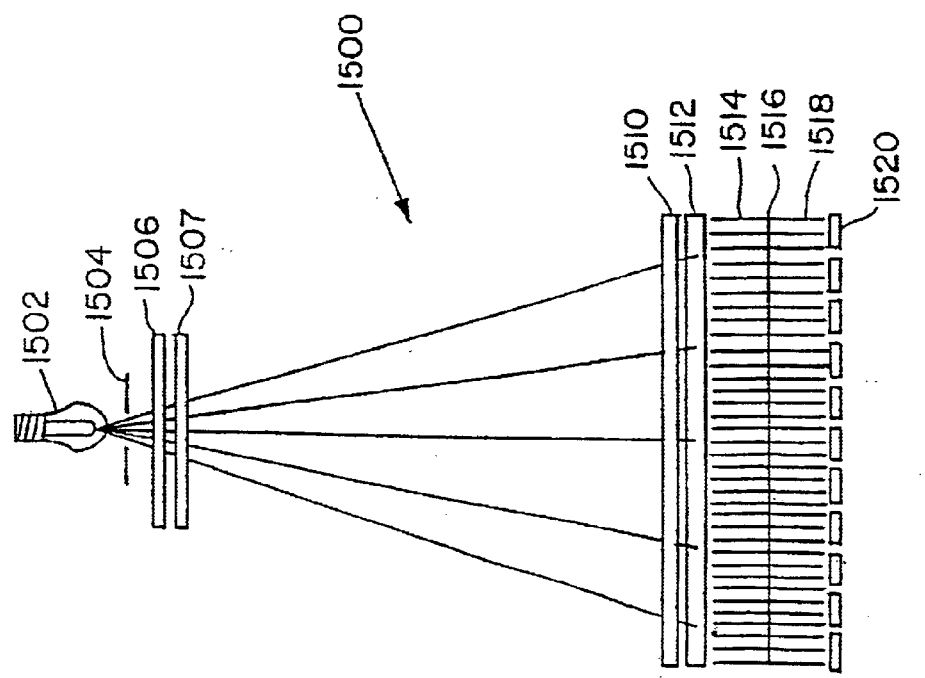

The laser system 1550 shown in FIG. 40B includes a laser, such as a helium neon, or diode laser, or surface emitting laser. A beam shaping aperture can be used in the shutter 1504 (pinhole) and the diffuser or microexpander 1508 can be followed by a spatial light modulator and expander 1556 which provides a collimated beam.

An alternative technique for the readout would be to use fast timing between the irradiation source and the readout. A very short light pulse may be injected in order to stimulate the phosphor. This may have a duration of 10–20 nanoseconds with conventional lasers and xenon lamps. Light pulses in the fempto second range can be used. As an example, a 10 nanosecond light pulse is injected onto the system. Immediately after this charge injection, the entire CCD is read out two or three times in order to clear any residual light. This readout can be accomplished in a very small time, typically, in a fraction of a microsecond. Following the CCD clearing, the CCD is turned in the sensing mode, to detect the stimulated fluorescence, which has a typical duration of approximately 10 microseconds. Time gating between the excitation and fluorescence light, provides an alternative means of reading out the CCD. A combination of time-gating and the use of the bandpass filter can also be used can also avoid flooding by modulating the duration and/or intensity of light to generate a sequence of frames.

An intensified CCD can be provided by using or another similar type of detect, such as amorphous silicon sensor, CID, can be provided by using either a microchannel plate-type, or proximity-focused image intensifier. The use of the intensifier not only enables amplification of the signal, but also can provide a convenient means of gating the CCD. A particular family of CCDs which might be applicable to this application are electron-bombarded CCD's which are currently manufactured by Pixel Vision Corporation (Beaverton, Oreg.). Position sensitive photomultipliers and tube-based cameras can also be used as detectors.

Alternatively, the fiberoptic plate can be manufactured with a red-absorbing glass which passes light in the UV-blue region (380–420 mm). The Schott BG-3 type glass is one example. This approach results in a relatively low numerical aperture for the fiberoptic plate, but still provides adequate blue-UV light pass for a reasonably strong signal onto the photosensor.

The thin layer optical coatings which provide extremely high discrimination between red and UV-blue, can be used. Selective discrimination by multi-layer coatings and green can also be used. Therefore, a green emitting stimulable phosphore can also be desirable for this type of application. Alternatively, a wavelength-shifting filter can be used in order to covert the UV-blue light of the phosphor to green light, and beyond this conversion step, the multi-layer optical coating discriminates between red and UV-blue.

This procedure accomplishes at least two important goals: (1) it reads the entire photostimulable plate in a snapshot instead of employing laser scanning; and (2) more of the available light is read out than with the slow scanning laser approach. Also, the method separates the x-ray acquisition step from the CCD read-out step. Therefore the dark current in the CCD is largely due to the time it takes to read it out and not to the length of the x-ray exposure.

This approach can be further modified to prevent pixel charge saturation which is a serious problem, especially with CCDs. The degree of saturation can be predicted by the time of the x-ray exposure; for example, a long x-ray exposure is required when imaging a dense or thick breast. This causes a large disparity between the signal under the breast, and the signal on the CCD is very high on the area where the x-ray beam does not pass through any tissue. This condition causes charge spillover.

A further objective is to provide is to provide a system for suppressing charge saturation in the imaging sensor. This is accomplished by tracking the time of the x-ray exposure and modulating the duration of the light pulse accordingly. For example, a very long x-ray exposure time suggests that significant charge saturation is to be expected. Having this information, the duration of the light pulse can be reduced and thereby generate a lower overall signal on the CCD. In some instances, a less then full discharge of the photostimulable phosphor plate can provide a sufficiently strong signal and avoid saturation. However, if a stronger signal is necessary, an additional light pulse can be injected in order to discharge the rest of the stored energy in the plate. This requires acquisition of another CCD or other imaging detector frame, and the frames can be added in the computer.

Alternatively, the exposure level can be tracked by recording the prompt scintillation of the photostimulable phosphor. Many of these phosphors also produce light immediately as a response to the x-ray interactions. This light can be detected by the CCD in order to assess the level of the x-ray exposure, and this information can be used in a similar way to provide exposure time information. Pixel binning can be used in all of the above techniques. The prompt scintillation can be used as an add-on to the final signal if desired, in order to increase the signal-to-noise ratio. If the photostimulable phosphor does not provide a strong prompt scintillation, a very thin coat of conventional phosphor can be applied on one side of the photostimulable phosphor, which will scintillate during the exposure.

A more detailed view of a preferred embodiment 1300 is illustrated in FIG. 37, where source 1302 directs stimulating light 1310 onto the x-ray storage element 1304 to induce fluorescence therein. The fluorescent light is collected through bandpass filter 1306 and fiber optic plate 1308 before being detected by area detector 1312, which in this particular illustration is an array of CCD elements.

Figure 38B:
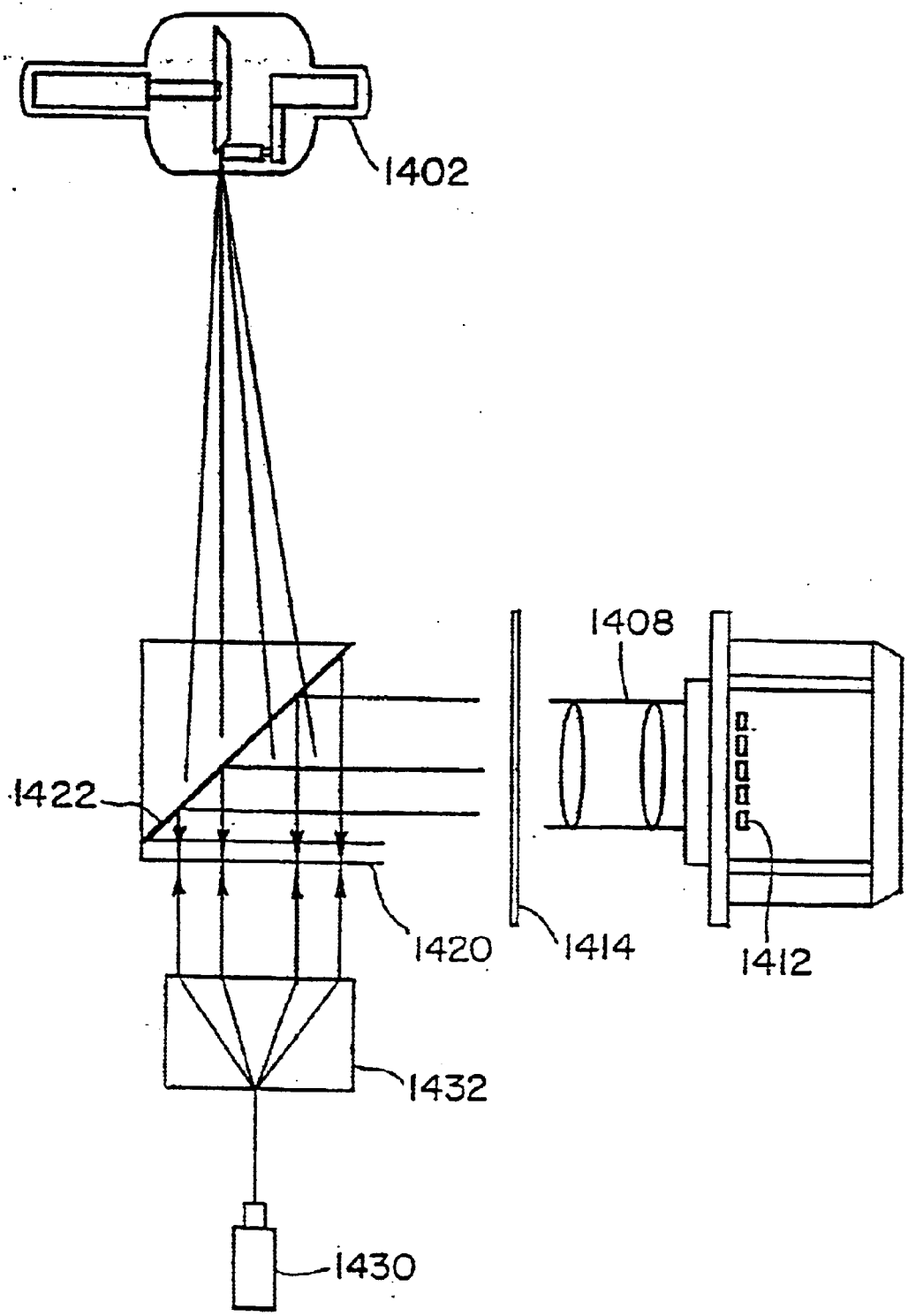

FIG. 38A illustrates another preferred embodiment 1400 in which one or more light sources 1406 illuminate the x-ray storage element 1404 after collection of transmitted x-rays from source 1402. The sources 1406 are positioned on the opposite side of element 1404 so as not to interfere with x-ray collection yet provide immediate data collection without moving the storage element 1404. In the illustrated embodiment, a lens 1408 is used with detector array 1412. Another embodiment that does not require transport or repositioning of the storage phosphor is illustrated in FIG. 38B in which mirror 1422 transmits the incident X-rays onto phosphor 1420. The laser 1430 and beam expander 1432 then stimulates emission that is reflected by the mirror 1422 through bandpass filter 1414, lens system 1408 onto the detector array 1412.

The method using the photostimulable phosphor readout with a CCD or other photodetector such as amorphous silicon is particularly suited to dental x-ray imaging. One approach to digital dental radiography has been to employ a CCD with an intraoral probe. These probes tend to be bulky due to the CCD and electronics. Cooling of the CCD is impractical, and there are additional costs associated with maintaining a clean CCD imaging probe from patient to patient.

Figure 39A:
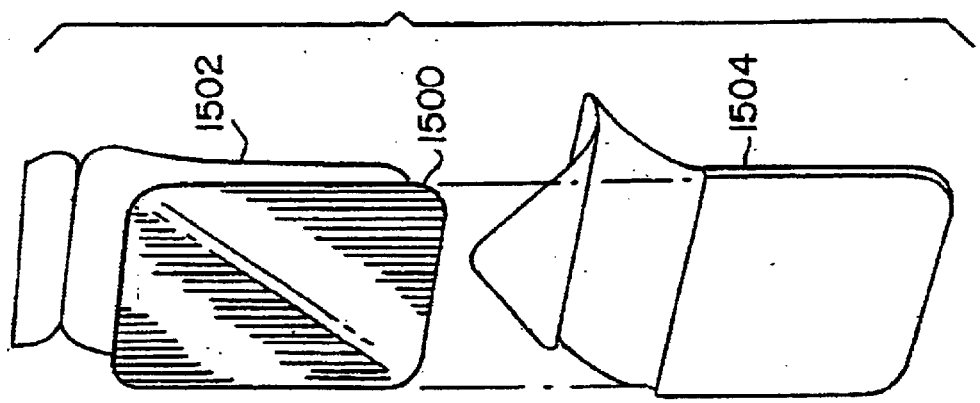
FIG. 39A is an exploded view of the components of an oral insert using an optical storage element for digital dental radiography.

A preferred embodiment of the invention uses a photostimulable phosphor that is placed in the mouth of the patient. As shown in FIG. 39A, an x-ray storage phosphor 1500 can be made having dimensions rendering it suitable for insertion in the oral cavity, for example between 4 cm2 and 20 cm2. The storage element 1500 can be inserted using slip 1502 that absorbs transmitted x-rays which is inserted in sleeve or cassette 1504 which is inserted into the patient's mouth adjacent to the teeth to be imaged. After the x-ray image is stored in the phosphor, the phosphor is removed from the oral cavity and exposed to light as described previously to provide the digital image. This has many advantages over the current practice. For example, this provides a simple disposable product to avoid the expense of cleaning the CCD probe after each oral insertion. The phosphor can also be cleaned and reused or it can be recycled in bulk quantities. The cassette can be flexible so that it can be bent upon oral insertion, or the phosphor can be coupled to a rigid support such as a fiber optic plate to prevent deformation of the phosphor.

Current stimulable phosphors are commonly available on a polyester or other bendable substrate. This phosphor can be incorporated in a plastic, light-tight package and used in a manner analogous to the use of conventional intraoral film. Using this approach, the phosphor is placed in contact with a fiberoptic plate on a readout instrument. A wavelength-selective filter is placed between the fiberoptic plate and an image sensor.

FIGS. 39B and 39C illustrate an alternate embodiments. FIG. 39B illustrates cassette 1700 which includes the following elements affixed as shown: photostimulable phosphor layer 1702, wavelength-selective filter 1704, fiberoptic plate 1706, and protective layer 1708. Photostimulable phosphor 1702 typically has a thickness of 50 to 500 microns, thickness being measured along the axis placed parallel to the path of stimulated fluorescence. Protective layer 1708 is transparent to allow the fluorescent light to exit for detection. Fiberoptic plate 1706 acts both as a mechanical substrate and an optical element, and it includes a contrast enhancement optical material, conventionally known in the art as an "extra-mural absorber." Typically, fiberoptic plate 1706 has a thickness of one to three millimeters. The small thickness of each of these elements offers a significant advantage over the prior art intraoral hardwired CCD's, which are bulky and often do not fit comfortably in the mouth, particularly in the mouths of children.

Cassette 1700 can be hermetically sealed and can be autoclaved or sterilized by other means. After each use, each cassette can be sterilized in a manner similar to that used for other dental instruments. Cassette 1700 can be enclosed in a small plastic disposable enclosure or very thin box for light shielding and to increase protection against cross-contamination.

Cassette 1700 can further be encapsulated in a disposable, plastic, light-tight cover as shown in FIG. 39B which shows cover 1710 in an open position and includes the above-recited elements absent wavelength-selective filter 1704. Cover 1710 protects the cassette from light. The omission of wavelength-selective filter 1704 is appropriate for use with a lens-coupled detection system or for use with time gating between stimulation and fluorescence.

The phosphor can be subjected to an intense light source after each use to erase any residual energy.

Certain flat panel area imaging detectors including CCDs have higher collection efficiency in the wavelength range between 400–700 nm. There are optical storage materials that emit in this range including $LiTaO_3:Tb3+$ which emits in the range between 500–700 nm (See Journal of Applied Physics, 79(6) 2853), kBr: In which emits around 440 nm (See, Phys. Stat. Sol(b), 180 K31, 1993), $Y_2SiO_5:Ce$, Tb, Zr which can emit up to 700 nm (See Mat. Chem. & Physics 38 (1994) 191), $Ba_5SiO_4Br_6$ which emits around 450 nm (Mat. Chem & Physics 21 (1989) 261–70), La O Br:Tb which emits in the range of 500–700 nm (See U.S. Pat. No. 4,236,078 the contents of which is incorporated herein by reference) and CaS:Sm, Eu which emits around 640 nm, the above referenced publications being incorporated herein by reference. These optical storage materials can be used as photostimulable or optostimulable elements which absorb x-rays and emit in the visible regions, particularly above 450 nm.

Another embodiment of the invention is illustrated in FIG. 40C. Flash illumination system 1570 includes light source 1572, stimulating light 1573, reflecting optics 1574, optical filter 1576, beam-shaping lens system 1578, light-diffusing element 1580, first fiberoptic plate 1582, photostimulable phosphor layer 1586, stimulated fluorescence 1588, second fiber optic plate 1590, wavelength-selective filter 1592, and electronic area detector 1594. Reflecting optics 1574 directs light emitted from light source 1572 toward optical filter 1576. Optical filter 1576 allows light in the red, green, or infrared wavelength spectrum to pass. The optical filter can be a monochromator or combination of filters which produces a relatively narrow spectral emission. After passing through optical filter 1576, stimulating light 1573 passes through beam-shaping lens system 1578, which redirects emitted light 1573 in a direction towards the stimulable phosphor layer 1586. Continuing its path away from light source 1572, stimulating light 1573 then contacts light-diffusing element 1580.

Light-diffusing element 1580 is fabricated of conventional frosted glass or plastic or a holographic beam-homogenizing element. Holographic light shaping diffusers from Physical Optics Corporation (Torrance, Calif.) can be used for this purpose. The combination of light shaping diffusers and reflective optics can be used for optimal light diffusion and maximum light output. Better than 98 percent illumination uniformity can be attained by using an integrating sphere system in conjunction with the stimulating light source. Light-diffusing element 1580 redistributes the intensity of stimulating light 1573 to produce a more uniform horizontal distribution of light 1573. Optionally, fiberoptic plate 1582 can be placed subsequent to light-diffusing element 1580 to further minimize non-parallel transmission of stimulating light 1573. The numerical aperture of fiberoptic plate 1582 can be adjusted to achieve this purpose. Stimulating light 1573 then contacts photostimulable phosphor layer 1586 where stimulating light 1573 is converted into stimulated fluorescence 1588. A reflective layer that reflects the fluorescent light can be placed before the stimulable phosphor in order to increase the collection of the fluorescent emission. This layer must also transmit the excitation radiation.

Photostimulable phosphor layer 1586 stores a representation of an imaged object in the form of a two-dimensional pattern of retained x-ray energy. Stimulating light 1573 contacts all of photostimulable phosphor layer 1586 on which the two dimensional pattern is retained. The contact of light 1573 with photostimulable phosphor layer 1586 triggers the release of stimulated fluorescence 1588 from layer 1586. The intensity and distribution of stimulated fluorescence 1588 is representative of the x-ray energy pattern stored on photostimulable phosphor layer 1586. Stimulated fluorescence 1588 then passes through second fiberoptic plate 1590. Second fiberoptic plate 1590 can include an extra-mural absorber, a contrast-enhancing optical material. Second fiberoptic plate guides stimulated fluorescence 1588 to wavelength-selective filter 1592.

Wavelength-selective filter 1592 blocks stimulating light 1573 while allowing stimulated fluorescence 1588, which has a shorter wavelength, to pass. Additionally, appropriate adjustments in the filter can be made to accommodate other wavelength bands. The filter 1592 can be a multilayer film having a thickness in the range of 1–10 microns and can be deposited directly on the fiberoptic plate and will not substantially impact the spatial resolution of the system.

After passing through wavelength-selective filter, stimulated fluorescence 1558 contacts electronic area detector 1594, which converts the pattern of stimulated fluorescence 1588 into representative electronic signals. Electronic area detector 1594 can be a CCD (front or back illuminated), amorphous silicon plate, or diode array. The detector can also be used with a proximity-type image intensifier.

Figure 40D:
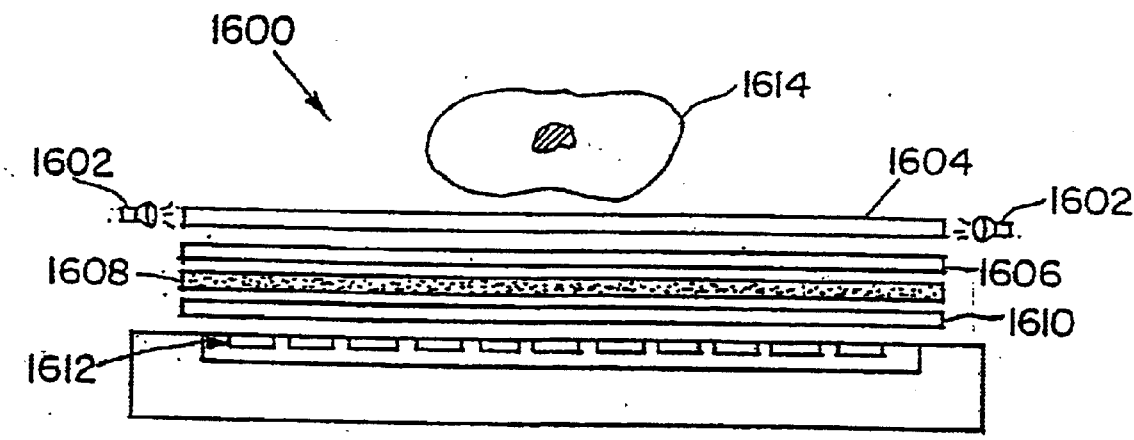

Flash illumination system 1600, shown in FIG. 40D, illustrates another embodiment. System 1600 includes light source 1602, diffuser 1604, light collimator 1606, photostimulable phosphor 1608, filter 1610, removable array 1612, and imaged object 1614. Light source 1602 can include a plurality of xenon lamps and is positioned at the outer edge of diffuser 1604. Positioned accordingly, light source 1602 is outside the path of radiation as it approaches photostimulable phosphor 1608. Therefore, neither light source 1602 or imaged object 1614 need be transported or repositioned between the stages of x-ray exposure and photostimulation. Light source 1602 produces a diffuse pulse of light transmitted to diffuser 1604. Diffuser 1604 disperses the intensity of the light pulse to produce a substantially uniform flash above photostimulable phosphor 1608. Optionally, the flash passes through light collimator 1606 before reaching photostimulable phosphor 1608. Photostimulable phosphor 1608 stores a representation of imaged object 1614 in the form of a two-dimensional pattern of retained x-ray energy. The flash irradiates the entire area of photostimulable phosphor 1608 at one instant and stimulates the phosphor to release a substantial portion of the stored x-ray energy in the form of fluorescence, the intensity and distribution of which is proportional to the absorbed x-ray energy pattern.

Filter 1610 absorbs x-ray radiation that passes through the photostimulable phosphor to prevent the radiation from contacting and potentially damaging removable array 1612. Examples of suitable filter materials include optical grade lead glass or a lead acrylic material. Filter 1612 can also include, or in the alternative consist of, a material capable of removing the longer-wavelength light continuing from light source 1602 while allowing the shorter-wavelength light emitted from photostimulable phosphor 1608 to pass through. This light-filtering process enhances the integrity of the light pattern received by removable array 1612 by removing "background interference" emanating from the light source. Removable array 1612 can be a charge coupled device that is positioned to receive and convert the filtered light pattern emanating from photostimulable phosphor 1608 into an electronic representation.

Figure 40F:
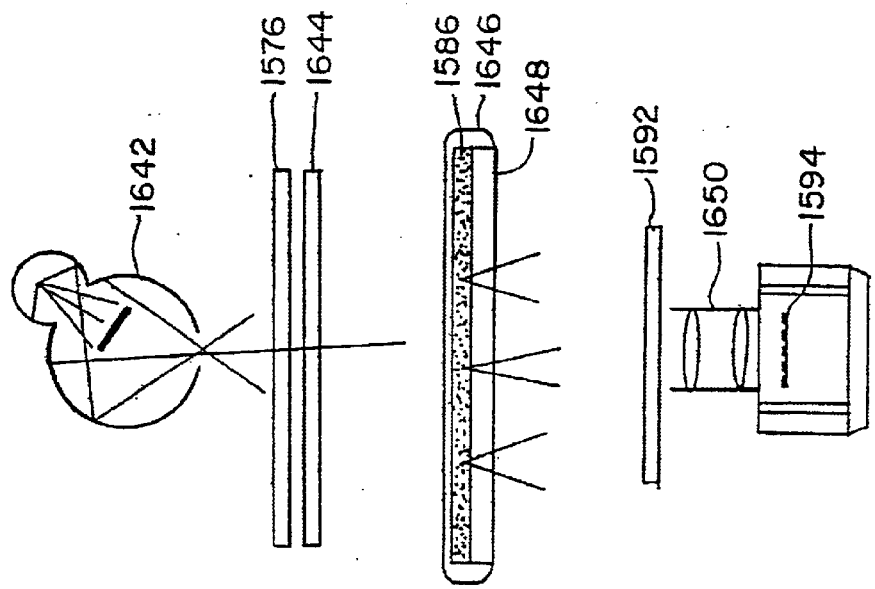
Figure 40E:
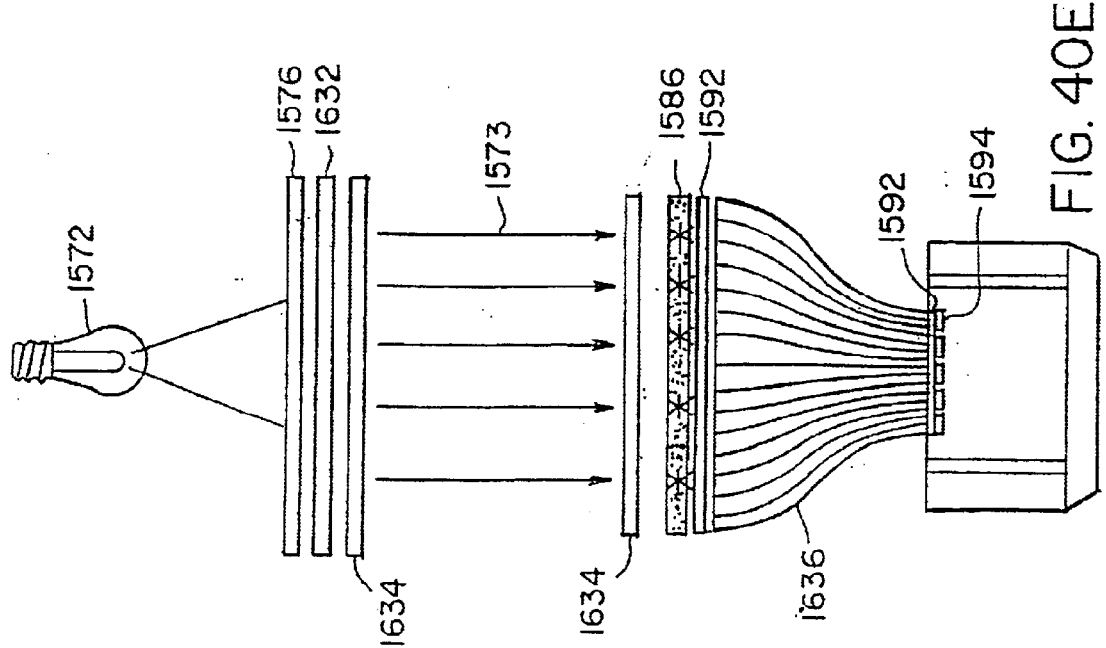

FIG. 40E illustrates an embodiment of the system in which uniform distribution of light intensity is provided by a spatial light modulator. Stimulating light 1573, emitted from light source 1572, passes through first optical filter 1576 and spatial light modulator 1632. Spatial light modulator 1632 redistributes the intensity of stimulating light to provide a beam of light of substantially uniform intensity. An example of a suitable spatial light modulator 1632 is an active or passive liquid crystal display. The resolution of the liquid crystal display matches that of electronic area detector 1594. Next, stimulating light 1573 passes through second optical filters 1634. Second optical filters 1634 reduce the angular spread of light 1573. Stimulating light 1573 then irradiates photostimulable phosphor 1586, triggering the release of stimulated fluorescence. The stimulated fluorescence travels through wavelength-selective filter 1592 to spatially-coherent fiberoptic element 1636. The stimulated fluorescence then travels through fiberoptic element 1636, through another wavelength-selective filter 1592 and onto electronic area detector 1594.

FIG. 40F illustrates an embodiment of a system incorporating an integrating sphere light source. Integrating spheres are in common use for various applications and systems providing uniform illumination are commercially-available Labsphere Corporation (North Sutton, N.H.). Integrating sphere 1642 produces highly uniform stimulating light. The stimulating light passes through optical filter 1576 and light homogenizer optical element 1644 before reaching photostimulable phosphor 1586. Photostimulable phosphor 1586 is bound to substrate 1648. Substrate 1648 is a transparent material such as glass or a wavelength-selective filter such as Schott BG-3 glass or a thin-film filter. Substrate 1648 and photostimulable phosphor are encapsulated within optically-transparent enclosure 1646. Optically-transparent enclosure 1646 is constructed with curved boundaries to minimize loss of light at the edges. Fluorescence stimulated from photostimulable phosphor travels through substrate 1648 and optically-transparent enclosure to wavelength-selective filter 1592. Passing through wavelength-selective filter 1592 and lens 1650, stimulated fluorescence is finally received by electronic area detector 1594.

In a flash illumination system, such as those illustrated in FIGS. 40C through 40G, problems may be encountered as a result of interference between the flash, which acts as an electromagnetic energy excitation pulse, and the stimulated fluorescent pulse. Even with the use of filters, a portion of the electromagnetic energy excitation pulse can pass through the relatively thin photostimulable phosphor layer, through the filters and onto the CCD array, where it may be registered by the detector thus producing interference. Interference can be avoided by using a flash with a duration much shorter than that of the stimulated fluorescent pulse. Through the process of time gating, a CCD array can be activated for a controlled interval of time such that it registers luminescence only for a limited interval of time matching the duration of the stimulated fluorescent pulse. The luminescence of most common photostimulable phosphors have a duration from about one to five microseconds. Accordingly, interference from the excitation pulse can be minimized by using an excitation pulse with a duration much shorter than the duration of the stimulated fluorescent pulse. Because the excitation pulse precedes the fluorescent pulse, a sufficiently-brief excitation pulse will be exhausted before the peak of the stimulated fluorescent pulse.

Following this approach, time gating can be used to read the CCD in the binned mode (heavy binning is desirable for very rapid acquisition) at very rapid frame rates and freeze an image frame in the desired binned or non-binned mode immediately after the decay of the excitation pulse. The signal detected during the fast successive framing is rapidly discarded and the image signal of the freeze frame which contains the fluorescent image is retained. This process can be repeated several times with lower intensity excitation pulses to prevent pixel saturation in areas of strong fluorescence. The gating technique can also be used in combination with wavelength-selective filtration.

Illustrated in FIG. 40G is another preferred embodiment of a system for retrieving an x-ray image from a storage phosphor 1666. Light source 1674 directs light through filter 1672, a spatial light modulator or light valve 1670, filters 1668 for reducing the angular spread of the excitation radiation 1675, storage phosphor 1666, filter 1665, photocathode 1664 of image intensifier 1660, output phosphor 1662, optical system 1650 and detector 1594. Optical system 1650 that is used to couple the image onto the pixelated detector can be a single lens, a lenslet array, a Fresnel-type lens, a refractive lens, a diffrac-tive optical element, or a reflection-type lens such as a Schmidt lens.

Figure 41:
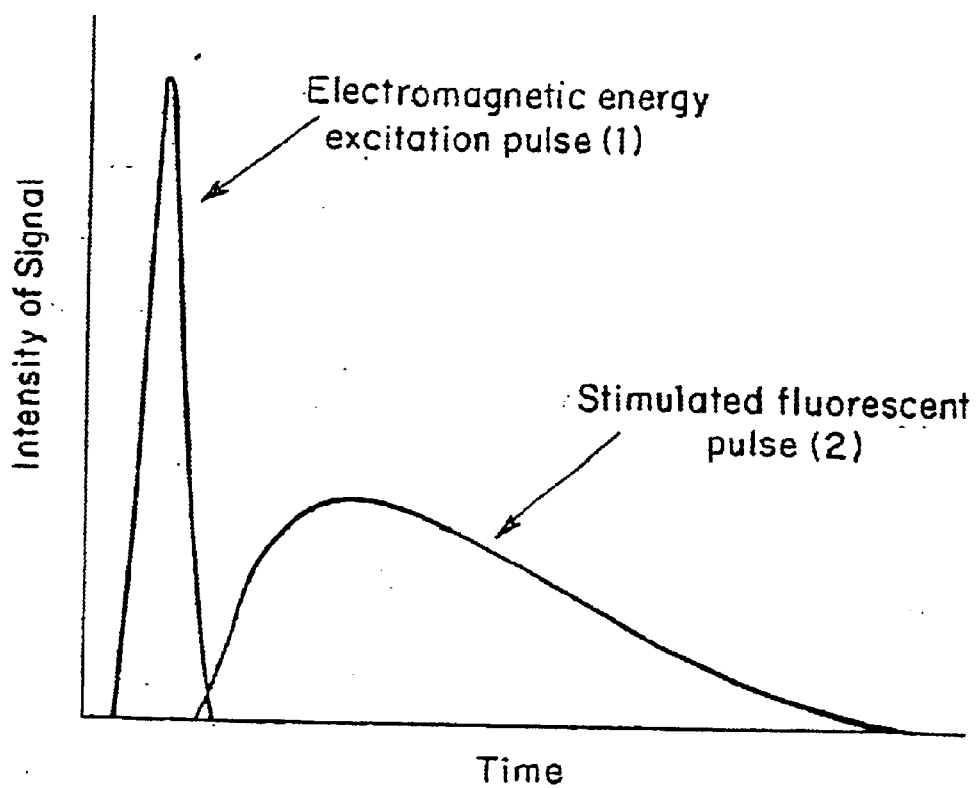
FIG. 41 is a chart illustrating the intensity of both the excitation pulse and the stimulated fluorescent pulse as a function of time.

FIG. 41 illustrates this sequential segregation of excitation pulse 1 and fluorescent pulse 2 as a function of time. Flash lamps with excitation pulses having a duration of 500 nanoseconds or shorter are widely available (for example, from Oriel Corporation, Stratford, Conn.) and would be suitable for this application. Alternatively, dispersed laser sources can easily achieve picosecond duration pulses which are also be suitable for this application. The light pulsing and gating approach can also be used to improve the contrast in conventional raster-scanned laser readout systems. In this method, the scanning laser beam, instead of being continuous, may be pulsed and gated with the optical fluorescence detector. This permits less or no filtration which will substantially increase the fluores-cence signal.

Figure 42:
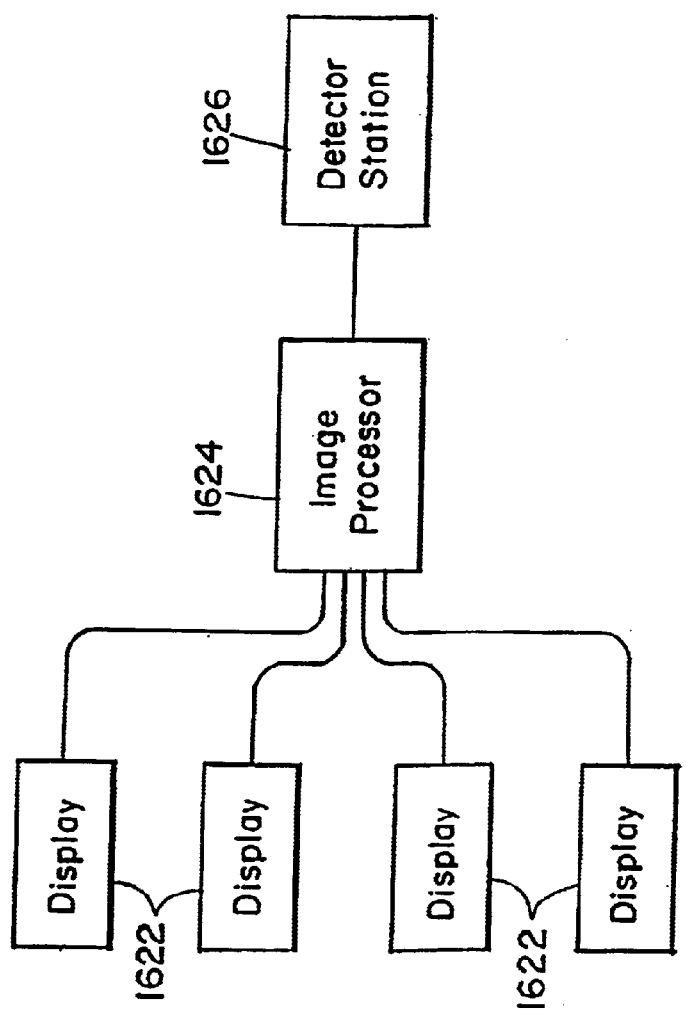
FIG. 42 schematically illustrates a network consisting of a plurality of displays connected to an image processor and a detector station.

In an embodiment of a larger system incorporating an optical storage element, electronic images from a central image processor can be networked to displays in a plurality of locations and stored in a central memory storage device. As illustrated in FIG. 42, a plurality of displays 1622 are electronically coupled with image processor 1624. Each display 1622 can be located at a patient station to display images obtained from an x-ray source at each station. After x-ray imaging is performed, the optical storage device is brought to detector station 1626, where it is processed and stored. A single CCD system within detector station 1626 converts a light pattern representative of an image into an electronic signal which is processed at image processor 1624 and which represents spatial position and x-ray intensity. This digital image is then transmitted to memory storage device at detector station 1626, where it is retained for subsequent retrieval. This embodiment permits a plurality of displays, at locations remote from one another, to be linked to a single detector system described herein, a single image processor, and a single memory storage device.

Another preferred embodiment of an optical readout system 1800 for imaging a stored x-ray image is illustrated in connection with FIG. 43. In this reverse illumination system, the optical storage element 1804 is illuminated by radiation 1810 from an infrared source 1802. The radiation 1810 passes through the area detector array 1806 that is transmissive or substantially transparent to infrared radiation. The detector can be an amorphous silicon sensor where the pixels have a thickness of less than 10 microns, preferably in the range of 1–2 microns. These detectors are highly transmissive at wavelengths beyond 800 nanometers while being highly sensitive to light in the range of 300–600 nanometers, including ultraviolet, blue, green and red bands.

The system 1800 can include a mechanical or optoelectronic shutter 1814, an infrared handpass filter 1816, a beam homogenizer and optional beam expander 1818. The detector 1806 can be positioned on an infrared transparent substrate 1808, an optional light reflector 1812, and an optional thin glass or fiberoptic plate with a thickness between 1 and 50 microns can be used between the detector 1806 and phosphor 1804.

Figures 43, 44:
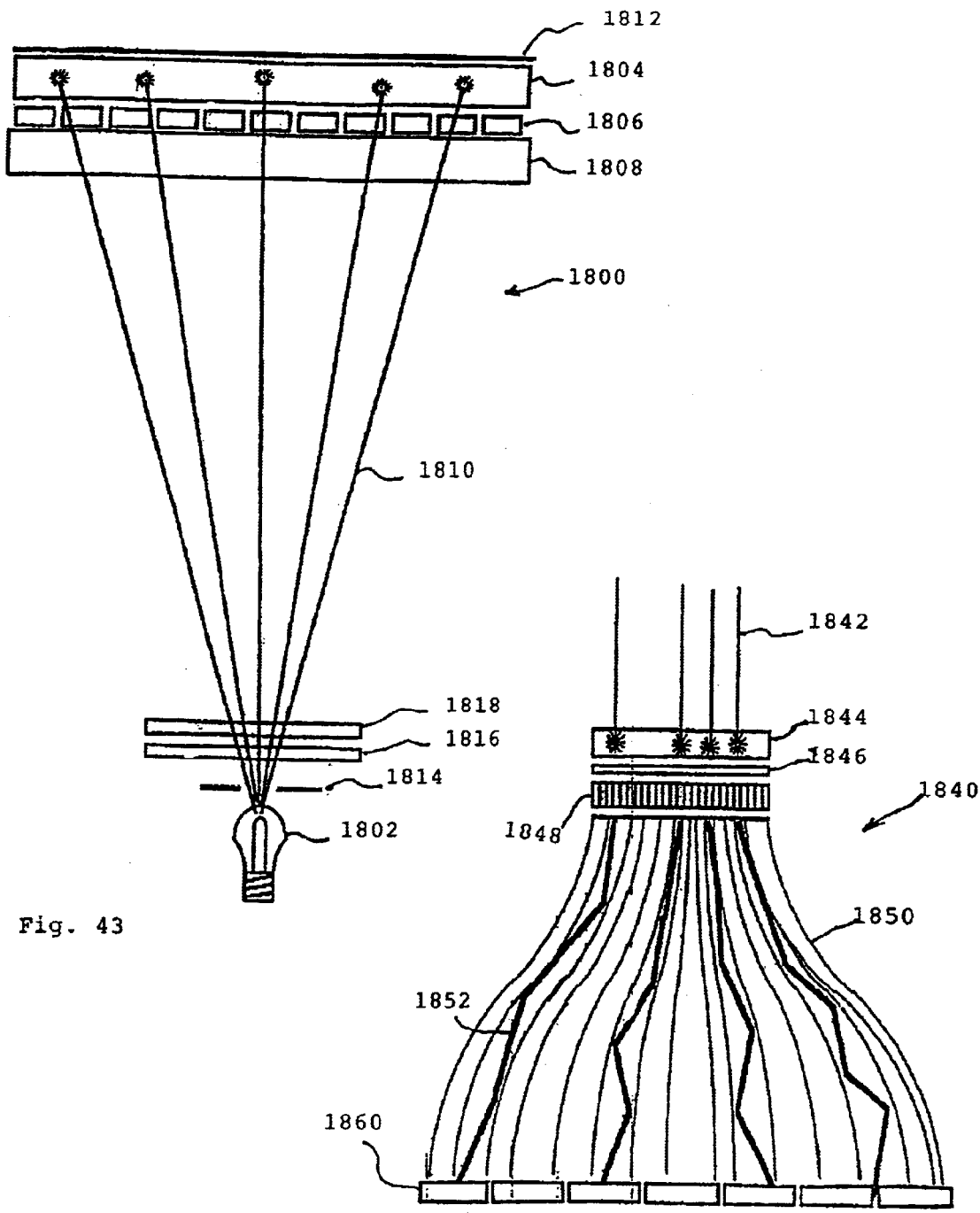
FIG. 43 illustrates the use of an infrared transparent detector for imaging a stored x-ray image.
FIG. 44 illustrates the use of an optical system to enlarge a stored x-ray image.

Illustrated in FIG. 44 is a preferred embodiment 1840 using a beam expander 1850 to enlarge the light image emitted by the storage element 1844 to provide a high resolution image at detector 1860. In this embodiment, light 1842 generates an optical image emitted by element 1844 which is directed through filter 1846 that removes light 1842. An optional image intensifier 1848 with or without time gating couples light into the fiber optic expander 1850, where light 1852 is delivered through individual fibers or waveguides to the detector array.

While the invention has been particularly shown and described with reference to a preferred embodiment thereof, it will be understood by those skilled in the art that various changes in form and details can be made therein without departing from the spirit and scope of the invention as defined by the appended claims.

What is claimed is:

1. An apparatus for examining a region of a patient comprising:
    an x-ray radiation source that directs radiation through the region:
    an optical storage element that receives radiation transmitted through the region at a storage region of the optical storage element, the storage region having a two dimensional surface area;
    a light source that simultaneously illuminates the entire two dimensional surface area of the storage region of the optical storage element to induce a fluorescence emission of an image of the region from the storage region;
    a two dimensional detector array optically coupled to the optical storage element such that the array receives the fluorescence emission at a plurality of pixels and generates an electronic representation of the tissue; and
    a two dimensional optical coupling system that couples the image of the region onto the two dimensional detector array.

2. The apparatus of claim 1 wherein the optical storage element comprises a photostimulable phosphor.

3. The apparatus of claim 1 wherein the light source further comprises a laser.

4. The apparatus of claim 1 wherein the light source further comprises a broadband light source.

5. The apparatus of claim 1 further comprising a cassette that contains the optical storage element.

6. The apparatus of claim 1 wherein the two dimensional optical coupling system comprises a thin film filter.

7. The apparatus of claim 1 wherein the light source is stationary relative to the optical storage element during illumination.

8. The apparatus of claim 1 wherein the optical coupling system comprises a fiberoptic device.

9. The apparatus of claim 1 wherein the optical coupling system comprises an image intensifier.

10. The apparatus of claim 1 wherein the optical coupling system comprises a lens.

11. The apparatus of claim 1 further comprising a spatial light modulator between the light source and the optical storage element.

12. The apparatus of claim 1 wherein the detector comprises a charge coupled device.

13. A method for examining tissue of a patient comprising the steps of:
    directing x-ray radiation through the tissue of the patient to produce a radiation pattern that is transmitted onto a two dimensional surface of an optical storage element, such that the optical storage element receives a two dimensional radiation pattern representative of the spatial distribution and intensity of the radiation pattern;
    directing light simultaneously onto the entire two dimensional surface of the optical storage element to produce an optical signal representative of the spatial distribution and intensity of the radiation pattern; and
    receiving the optical signal on a two dimensional detector array comprising a plurality of pixels and generating an electronic representation of the tissue.

14. The method of claim 13 wherein the optical storage element comprises a photostimulable phosphor.

15. The method of claim 13 wherein the pulse of light is produced by a light source comprising a broadband light source.

16. The method of claim 13 wherein the optical storage element is contained in a cassette.

17. The method of claim 13 further comprising optically coupling the optical signal to the detector array with an optical element.

18. The method of claim 17 further comprising filtering the optical signal with the optical element.

19. The method of claim 17 further comprising intensifying the optical signal with an image intensifier.

20. An apparatus for examining a patient's spine comprising:
    an x-ray radiation source emitting radiation which is directed through the spine;
    an optical storage element having a surface area that receives the radiation transmitted through the spine;
    a detector into which the optical storage element can be mounted comprising a detector array; and
    a light source that can be optically coupled to the surface area of the optical storage element to simultaneously illuminate the entire surface area of the optical storage element to produce an optical signal that is transmitted onto the detector array.

21. The apparatus of claim 1 wherein the x-ray radiation source comprises an x-ray tube.

22. The apparatus of claim 1 wherein the coupling system comprises an expander.

23. The apparatus of claim 22 wherein the expander comprises a fiber optic device.

24. The apparatus of claim 22 further comprising a filter positioned between the storage element and the expander.

25. The apparatus of claim 1 wherein the light source emits light having a wavelength longer than 800 nanometers.

26. The apparatus of claim 1 wherein the detector array is an amorphous silicon sensor.

* * * * *